(12) United States Patent
Sakaguchi

(10) Patent No.: US 6,762,321 B2
(45) Date of Patent: Jul. 13, 2004

(54) AMIDE COMPOUNDS AND USE THEREOF

(75) Inventor: Hiroshi Sakaguchi, Toyonaka (JP)

(73) Assignee: Sumitomo Chemical Company, Limited, Osaka (JP)

(*) Notice: Subject to any disclaimer, the term of this patent is extended or adjusted under 35 U.S.C. 154(b) by 16 days.

(21) Appl. No.: 10/311,013

(22) PCT Filed: Jun. 13, 2001

(86) PCT No.: PCT/JP01/05037
§ 371 (c)(1),
(2), (4) Date: Dec. 12, 2002

(87) PCT Pub. No.: WO02/00607
PCT Pub. Date: Jan. 3, 2002

(65) Prior Publication Data
US 2003/0195354 A1 Oct. 16, 2003

(30) Foreign Application Priority Data

| Jun. 29, 2000 | (JP) | 2000-195649 |
| Dec. 13, 2000 | (JP) | 2000-378666 |
| Mar. 29, 2001 | (JP) | 2001-096096 |

(51) Int. Cl.[7] .................. C07C 233/05; A01N 37/18
(52) U.S. Cl. ................... 564/180; 564/170; 564/182; 514/617
(58) Field of Search ................ 564/170, 180, 564/182; 514/617

(56) References Cited

U.S. PATENT DOCUMENTS

| 3,574,748 A | 4/1971 | Mayer et al. |
| 5,023,275 A | 6/1991 | Amick |
| 6,225,334 B1 | 5/2001 | Seitz et al. |
| 6,313,173 B1 | 11/2001 | Seitz et al. |

FOREIGN PATENT DOCUMENTS

| EP | 410726 A1 | 1/1991 |
| FR | 2004697 A1 | 11/1969 |
| WO | WO 96/17825 A1 | 6/1996 |
| WO | WO 96/16500 A1 | 4/1998 |
| WO | WO 01/95721 A2 | 12/2001 |

*Primary Examiner*—Shailendra Kumar
(74) *Attorney, Agent, or Firm*—Birch, Stewart, Kolasch & Birch, LLP

(57) ABSTRACT

An amide compound given by formula [I]:

$$R^1-X-\underset{Y}{\overset{H}{\underset{\|}{C}}}=\underset{}{\overset{Ar}{C}}-\underset{}{\overset{R^2}{C}}-N-A-\underset{}{\overset{Z^1}{\underset{Z^2}{\bigcirc}}}$$

wherein $R^1$ represents a C1–C10 haloalkyl and so on, R2 represents a hydrogen and so on, X represents an oxygen or sulfur, Y represents an oxygen or sulfur, Ar represents an aromatic group, A represents an ethylene and so on, and $Z^1$ and $Z^2$ represent alkyl, alkoxy and so on, and a fungicide containing it as an active ingredient.

14 Claims, No Drawings

AMIDE COMPOUNDS AND USE THEREOF

This application is a 371 of PCT/JP01/05037, filed Jun. 13, 2001.

1. Technical Field

The present invention relates to amide compounds and their use for fungicide.

2. Background Arts

The present invention provides an amide compound which can be more excellent fungicidal active ingredient, though various fungicides for controlling plant diseases have been known hitherto.

DISCLOSURE OF THE INVENTION

The present invention provides an amide compound given by formula [I]:

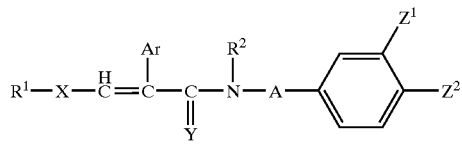

wherein $R^1$ represents a C1–C10 haloalkyl group, C2–C10 haloalkenyl group, C3–C10 haloalkynyl group, C3–C8 halocycloalkyl group or C3–C10 alkynyl group; $R^2$ represents a hydrogen atom or C1–C3 alkyl group (namely, methy, ethyl, propyl and isopropyl); X represents an oxygen atom or sulfur atom; Y represents an oxygen atom or sulfur atom; Ar represents an aromatic group; A represents an ethylene group or trimethylene group, said ethylene group and trimethylene group may be substituted by one or more selected from halogen atom, amino group, hydroxy group, cyano group, nitro group, C1–C6 alkyl group, C3–C6 cycloalkyl group, C3–C6 cycloalkenyl group, C1–C6 alkoxy group, C1–C6 haloalkoxy group, C1–C6 alkylthio group, C1–C6 haloalkylthio group, C2–C6 (alkoxycarbonyl) group and tri(C1–C6 alkyl)silyl group; $Z^1$ and $Z^2$ are the same or different and represents a halogen atom (chlorine, bromine, fluorine, iodine), C1–C6 alkyl group, C1–C6 haloalkyl group, C2–C6 alkenyl group, C2–C6 alkynyl group, C3–C6 cycloalkyl group, C1–C6 alkoxy group, C1–C6 haloalkoxy group, C2–C6 (alkoxyalkoxy) group, C4–C6 (cycloalkylalkoxy) group, C3–C6 alkenyloxy group, C3–C6 haloalkenyloxy group, C3–C6 alkynyloxy group, C3–C6 haloalkynyloxy group, C3–C6 cycloalkoxy group, C3–C6 cycloalkenyloxy group, cyano C1–C5 alkoxy group, C1–C6 alkylthio group, C1–C6 haloalkylthio group (C1–C5 alkoxy)carbonyl group, phenoxy group, benzyloxy group, hydroxy group or cyano group, the benzene ring of said phenyl group and benzyloxy group may be substituted by one or more selected from halogen atom (chlorine, bromine, fluorine, iodine) C1–C6 alkyl group, C1–C6 alkoxy group, trifluoromethyl group, amino group and nitro group; and $Z^1$ and $Z^2$ may represents C2–C6 alkylenedioxy group together, (hereinafter, referred to as the present compound) and fungicide comprising it as an active ingredient.

In the present invention, examples of the C1–C10 haloalkyl group for $R^1$ include fluoromethyl, difluoromethyl, trifluoromethyl, chlorodifluoromethyl, chlorofluoromethyl, bromodifluoromethyl, trichloromethyl, dichlorobromomethyl, 1,1,2,2,2-pentafluoroethyl, 2,2,2-trifluoroethyl, 2,2-difluoroethyl and 2-fluoroethyl; examples of the C2–C10 haloalkenyl group include 2-fluorovinyl, 2,2-difluorovinul, trifluorovinyl, 3-chloropropenyl, 3,3-dichloropropenyl, 3-fluoropropenyl, 3,3-difluoropropenyl, 2,3,3-trifluoropropenyl and 10-fluoro-2-decenyl; examples of the C3–C10 haloalkynyl group include 3-fluoro-2-propynyl, 3-chloro-2-propynyl, 3-bromo-2-propynyl, 3-iodo-2-propynyl, 4-fluoro-2-butynyl, 4,4-difluoro-2-butynyl, 4,4,4-trifluoro-2-butynyl and 4-chloro-2-butynyl; examples of the C3–C8 halocycloalkyl group include 2,2-difluorocyclopropyl, 2,3,4-trifluorocyclobutyl, 2,5-dichlorocyclopentyl, 4,4-difluorocyclohexy and 2-chlorocycloheptyl; and examples of the C3–C10 alkynyl group include 2-propynyl, 2-butynyl, 3-butynyl, 1-methyl-2-propynyl, 5-pentynyl and 7-octynyl. Among them, C1–C3 haloalkyl group, C2–C3 haloalkenyl group, C3–C5-haloalkynyl group, C3–C6 halocycloalkyl group and C3–C8 alkynyl group are preferable, and especialy fluoromethyl, difluoromethyl, trifluoromethyl and 2-propynyl are more preferable for $R^1$.

In the present invention, examples of the aromatic group for Ar include aromatic hydrocarbyl groups such as phenyl, naphthyl (1-naphthyl, 2-naphthyl) and so on; and aromatic heterocyclic groups such as thienyl (2-thienyl, 3-thienyl), furyl (2-furyl, 3-furyl), pyrrolyl (1-pyrrolyl, 2-pyrrolyl, 3-pyrrolyl), pyrazolyl (1-pyrazolyl, 3-pyrazolyl, 4-pyrazolyl), imidazolyl (1-imidazolyl, 2-imidazolyl, 4-imidazolyl), triazolyl (1-triazolyl, 4-triazolyl), tetrazolyl (1-tetrazolyl, 5-tetrazolyl), thiazolyl (2-thiazolyl, 4-thiazolyl, 5-thiazolyl), isothiazolyl (3-isothiazolyl, 4-isothiazolyl, 5-isothiazolyl), oxazolyl (2-oxazolyl, 4-oxazolyl, 5-oxazolyl), isoxazolyl (3-isoxazolyl, 4-isoxazolyl, 5-isoxazolyl), thiadiazolyl (e.g. 1,2,5-thiadiazol-4-yl, 1,3,4-thiadiazol-2-yl, 1,2,3-thiadiazol-5-yl), pyridyl (2-pyridyl, 3-pyridyl, 4-pyridyl), pyrimidinyl (2-pyrimidinyl, 4-pyrimidinyl, 5-pyrimidinyl), pyrazinyl, pyridazinyl (3-pyridazinyl, 4-pyridazinyl), benzofuryl (2-benzofuryl, 3-benzofuryl, 4-benzofuryl, 5-benzofuryl, 6-benzofuryl, 7-benzofuryl), benzothienyl (2-benzothienyl, 3-benzothienyl, 4-benzothienyl, 5-benzothienyl, 6-benzothienyl, 7-benzothienyl), indolyl (1-indolyl, 2-indolyl, 3-indolyl, 4-indolyl, 5-indolyl, 6-indolyl, 7-indolyl), benzothiazolyl (2-benzothiazolyl, 4-benzothiazolyl, 5-benzothiazolyl, 6-benzothiazolyl, 7-benzothiazolyl), benzimidazolyl (1-benzimidazolyl, 2-benzimidazolyl, 4-benzimidazolyl, 5-benzimidazolyl, 6-benzimidazolyl, 7-benzimidazolyl), benzopyrazolyl (1-benzopyrazolyl, 2-benzopyrazolyl, 3-benzopyrazolyl, 4-benzopyrazolyl, 5-benzopyrazolyl, 6-benzopyrazolyl, 7-benzopyrazolyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), pyrazolopyrimidinyl, imidazopyrimidinyl, thiophenopyrimidinyl, thiazolopyrimidinyl, pyrazolopyridyl, imidazopyridyl, thiophenopyridyl, thiazolopyridyl and so on; and said aromatic hydrocarbyl group and aromatic heterocyclic group may be substituted. Typical examples of the substituents include halogen (chlorine, bromine, fluorine, iodine), amino, hydroxy, cyano, nitro, C1–C10 alkyl (e.g. methyl, ethyl, propyl, isopropyl, butyl, isobutyl, 1-methylpropyl, pentyl, 1-methylbutyl, 1-ethylbutyl, 2-methylbutyl, 3-methylbutyl, 2,2-dimethylpropyl, 1,2-dimethylbutyl, 1,1-dimethylpropyl, hexyl, 1-methylpentyl, 1-ethylpentyl, 3,3-dimethylbutyl, heptyl, 3,7-dimethyloctyl), C1–C10 haloalkyl (e.g. trifluoromethyl, 2,2,2-trifluoroethyl, 1,1,2,2- tetrafluoroethyl), cyano C1–C9 alkyl (e.g. cyanomethyl, 1-cyanoethyl, 2-cyanoethyl, 3-cyanopropyl, 5-cyanohexyl), C2–C10 alkenyl (e.g. vinyl, 1-propenyl, 2-propenyl, 1-methyl-1-propenyl, 1-butenyl, 2-butenyl, 3-butenyl, 3,3-dimethyl-1-butenyl, 4-pentenyl, 5-hexenyl), C2–C10 haloalkenyl (e.g. 2-fluorovinyl, 3-chloro-2-propenyl, 3,3-dichloro-2-propenyl, 2-fluoro-1-propenyl, 3,3,3-trifluoro-1-propenyl, 4-chloro-3-butenyl, 2-chloro-3-methyl-1-butenyl, 2-fluoro-5-hexenyl), C2–C10 alkynyl (e.g. ethynyl, 1-propynyl, 2-propynyl, 1-methyl-2-propynyl, 1-ethyl-2-propynyl, 1-butynyl, 3,3-dimethyl-1-butynyl, 3-butynyl, 4-pentynyl, 5-hexynyl), C2–C10 haloalkynyl (e.g. 2-fluoroethynyl, 2-chloroethynyl, 3-chloro-2-propynyl, 4-fluoro-3-butynyl, 5-chloro-4-pentynyl, 6-bromo-5-hexynyl), C3–C6 cycloalkyl (e.g. cyclopropyl, cyclobutyl, cyclopentyl, cyclohexyl), C3–C6 cycloalkenyl (e.g. 2-cyclopentenyl, 2-cyclohexenyl), C1–C10 alkoxy (e.g. methoxy, ethoxy, propoxy, isopropoxy, butoxy, sec-butoxy, isobutoxy, pentyloxy), C1–C10 haloalkoxy (e.g. trifluoromethoxy, difluoromethoxy, bromodifluoromethoxy, chlorodifluoromethoxy, fluoromethoxy, 2,2,2-trifluoroethoxy, 1,1,2,2-tetrafluoroethoxy), C3–C10 alkenyloxy (e.g. 2-propenyloxy, 1-methyl-2-propenyloxy, 1-ethyl-2-propenyloxy, 2-butenyloxy, 3-butenyloxy, 2,2-dimethyl-3-butenyloxy, 4-pentenyloxy, 5-hexenyloxy), C3–C10 haloalkenyloxy (e.g. 3-chloro-2-propenyloxy, 3,3-dichloro-2-propenyloxy, 2-fluoro-1-propenyloxy, 3,3,3-trifluoro-1-propenyloxy, 4-chloro-3-butenyloxy, 2-chloro-3-methyl-1-butenyloxy, 2-fluoro-5-hexenyloxy), C3–C10 alkynyloxy (e.g. 2-propynyloxy, 1-methyl-2-propynyloxy, 1-ethyl-2-propynyloxy, 2-butynyloxy, 3-butynyloxy, 4-pentynyloxy, 5-hexynyloxy), C3–C10 haloalkynyloxy (e.g. 3-chloro-2-propynyloxy, 3-fluoro-2-propynyloxy, 4-fluoro-3-butynyloxy, 5-chloro-4-pentynyloxy, 6-bromo-5-hexynyloxy), C3–C10 cycloalkoxy (e.g. cyclopropoxy, cyclobutoxy, cyclopentyloxy, cyclohexyloxy, cyclooctyloxy), cyano C1–C9 alkoxy (e.g. cyanomethoxy, 1-cyanoethoxy, 2-cyanoethoxy, 3-cyanopropoxy, 5-cyanohexyloxy), C1–C10 alkylthio (e.g. methylthio, ethylthio, propylthio, butylthio, isobutylthio, sec-butylthio, pentylthio, hexylthio), C1–C10 haloalkylthio (e.g. trifluoromethylthio, difluoromethylthio, bromodifluoromethylthio, chlorodifluoromethylthio, fluoromethylthio, 2,2,2-trifluoroethylthio, 1,1,2,2-tetrafluoroethylthio), C2–C10 (alkoxycarbonyl) (e.g. methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, hexyloxycarbonyl), tri(C1–C6 alkyl)silyl (e.g. trimethylsilyl, triethylsilyl), C3–C5 alkylene (e.g. trimethylene, tetramethylene, pentamethylene) and methylenedioxy. Among them, preferred Ar's are 4-methylphenyl group, 4-ethylphenyl group, 4-methoxyphenyl group, 4-chlorophenyl group, 4-trifluoromethylphenyl group, 3,4-tetramethylenephenyl group (5,6,7,8-tetrahydronaphthalen-2-yl group), 3,4-trimethylenephenyl group (indan-5-yl group) and 2-naphthyl group.

In the present invention, the ethylene group (—$CH_2CH_2$—) and trimethylene group for A may be substituted by at least one selected from halogen (chlorine, bromine, fluorine, iodine), amino, hydroxy, cyano, nitro, C1–C6 alkyl (e.g. methyl, ethyl, propyl, isopropyl, butyl, sec-butyl, isobutyl, t-butyl), C3–C6 cycloalkyl (e.g. cyclopropyl, cyclopentyl, cyclohexyl), C3–C6 cycloalkenyl, C1–C6 alkoxy (e.g. methoxy, ethoxy, propoxy, isopropoxy, butoxy, sec-butoxy, isobutoxy, pentyloxy), C1–C6 haloalkoxy (e.g. trifluoromethoxy, difluoromethoxy, bromodifluoromethoxy, chlorodifluoromethoxy, fluoromethoxy, 2,2,2-trifluoroethoxy, 1,1,2,2-tetrafluoroethoxy), C1–C6 alkylthio (e.g. methylthio, ethylthio, propylthio, butylthio, isobutylthio, sec-butylthio, pentylthio, hexylthio), C1–C6 haloalkylthio (e.g. trifluoromethylthio, difluoromethylthio, bromodifluoromethylthio, chlorodifluoromethylthio, fluoromethylthio, 2,2,2-trifluoroethylthio, 1,1,2,2-tetrafluoroethylthio), C2–C6 (alkoxycarbonyl) (e.g. methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, hexyloxycarbonyl) and (C1–C6 alkyl)silyl (e.g. trimethylsilyl, triethylsilyl). Among them, ethylene (—$CH_2CH_2$—) is preferable for A.

In the present invention, examples of the C1–C6 alkyl group for $Z^1$ and $Z^2$ include methyl, ethyl, propyl, isopropyl, butyl, isobutyl, sec-butyl, pentyl, 1-methylbutyl, 1-ethylbutyl, 2-methylbutyl, 3-methylbutyl, 2,2-dimethylpropyl, 1,2-dimethylpropyl, 1,1-dimethylpropyl, hexyl, 1-methylpentyl and 3,3-dimethylbutyl; examples of the C1–C6 haloalkyl group include trifluoromethyl, 2,2,2-trifluoroethyl and 1,1,2,2-tetrafluoroethyl; examples of the C2–C6 alkenyl group include vinyl, 2-propenyl, 1-methyl-2-propenyl, 2-methyl-2-propenyl, 2-butenyl, 3-butenyl, 3-methyl-2-butenyl, 4-methyl-3-butenyl, 4-pentenyl and 5-hexenyl; C2–C6 alkynyl group include ethynyl, 2-propynyl, 1-methyl-2-propynyl, 1-ethyl-2-propynyl, 2-butynyl, 3-butynyl, 1-methyl-2-butynyl, 2-pentynyl and 4,4-dimethyl-2-pentynyl; examples of the C3–C6 cycloalkyl group include cyclopropyl, cyclopentyl and cyclohexyl; examples of the C1–C6 alkoxy group include methoxy, ethoxy, propoxy, isopropoxy, butoxy, sec-butoxy, isobutoxy and pentyloxy; examples of the C1–C6 haloalkoxy group include trifluoromethoxy, difluoromethoxy, bromodifluoromethoxy, chlorodifluoromethoxy, fluoromethoxy, 2,2,2-trifluoroethoxy and 1,1,2,2-tetrafluoroethoxy; examples of the C2–C6 (alkoxyalkoxy) group include methoxymethoxy, 2-methoxyethoxy, ethoxymethoxy and isopropoxymethoxy; examples of the C4–C6 (cycloalkylalkoxy) group include cyclopropylmethyl; examples of the C3–C6 alkenyloxy group include 2-propenyloxy, 1-methyl-2-propenyloxy, 2-methyl-2-propenyloxy, 2-butenyloxy, 3-butenyloxy, 3-methyl-2-butenyloxy, 4-methyl-3-butenyloxy, 4-pentenyloxy and 5-hexenyloxy; examples of the C3–C6 haloalkenyloxy group include 2-chloro-2-propenyloxy, 3-fluoro-2-propenyloxy, 3-chloro-2-propenyloxy, 3-bromo-2-propenyloxy, 3,3-dichloro-2-propenyloxy, 2,3,3-trifluoro-2-propenyloxy, 4-chloro-2-butenyloxy, 4-chloro-3-butenyloxy and 3-chloro-3-butenyloxy; examples of the C3–C6 alkynyloxy group include 2-propynyloxy, 1-methyl-2-propynyloxy, 1-ethyl-2-propynyloxy, 2-butynyloxy, 3-butynyloxy, 1-methyl-2-butynyloxy, 2-pentynyloxy, 4-pentynyloxy and 4,4-dimethyl-2-pentynyloxy; examples of the C3–C6 haloalkynyloxy group include 3-fluoro-2-propynyloxy, 3-chloro-2-propynyloxy, 3-bromo-2-propynyloxy, 3-chloro-1-methyl-2-propynyloxy, 4,4,4-trifluoro-2-butynyloxy, 4-chloro-3-butynyloxy and 5-chloro-4-pentynyloxy; examples of the C3–C6 cycloalkoxy group include cyclopropoxy, cyclopentyloxy and cyclohexyloxy; examples of the C3–C6 cycloalkenyloxy group include cyclopentenyloxy and cyclohexenyloxy; examples of the cyano C1–C5 alkoxy group include cyanomethoxy, 1-cyanoethoxy and 2-cyanoethoxy; examples of the C1–C6 alkylthio group include methylthio, ethylthio, propylthio, butylthio, isobutylthio, sec-butylthio, pentylthio and hexylthio; examples of the C1–C6 haloalkylthio group include trifluoromethylthio, difluoromethylthio, bromodifluoromethylthio, chlorodifluoromethylthio, fluoromethylthio, 2,2,2-trifluoroethylthio and 1,1,2,2-tetrafluoroethylthio; examples of the (C1–C5 alkoxy) carbonyl group include methoxycarbonyl, ethoxycarbonyl, propoxycarbonyl, isopropoxycarbonyl, butoxycarbonyl, isobutoxycarbonyl, sec-butoxycarbonyl and pentyloxycarbonyl; examples of the optionally substituted phenoxy group include phenoxy, 4-chlorophenoxy, 4-methylphenoxy, 4-methoxyphenoxy and 4-trifluoromethylphenoxy; examples of the optionally substituted benzyloxy group include benzyloxy, 4-chlorobenzyloxy, 4-methylbenzyloxy, 4-methoxybenzyloxy and 4-trifluoromethylbenzyloxy; and examples of the C2–C6 alkylenedioxy group include ethylenedioxy, propylenedioxy and trimethylenedioxy. Among them, preferable are methoxy for $Z^1$ and methoxy and 2-propynyloxy for $Z^2$.

In the present compounds, there exist (E) and (Z) isomers based on C=C double bond bonded with Ar and X, and the present invention include each isomer and mixtures thereof.

In the present compounds, the compounds having excellent efficacy for controlling plant diseases are exemplified by N-[2-(3,4-dimethoxyphenyl)ethyl]-3-difluoromethoxy-2-(4-methylphenyl)acrylamide, N-[2-(3,4-dimethoxyphenyl)ethyl]-3-difluoromethoxy-2-[2-(5,6,7,8-tetrahydronaphthalen-2-yl)acrylamide, N-[2-{3-methoxy-4-(2-propynyloxy)phenyl}ethyl]-3-difluoromethoxy-2-(5,6,7,8-tetrahydronaphthalen-2-yl)acrylamide, N-[2-{3-methoxy-4-(2-propynyloxy) phenyl}ethyl]-3-difluoromethoxy-2-(4-methylphenyl)acrylamide, N-[2-(3,4-dimethoxyphenyl)ethyl]-3-difluoromethoxy-2-(4-chlorophenyl)acrylamide and N-[2-{3-methoxy-4-(2-propynyloxy)phenyl}ethyl]-3-difluoromethoxy-2-(4-chlorophenyl)acrylamide.

The present compounds can be produced, for example, by the following [Production method A], [Production method B] or [Production method C]. In these production methods, a protective group may be utilized for protecting a functional group from chemical reaction, if necessary.

Production Method A

Production method of making the compound given by formula [II] to react with the compound given by formula [III]

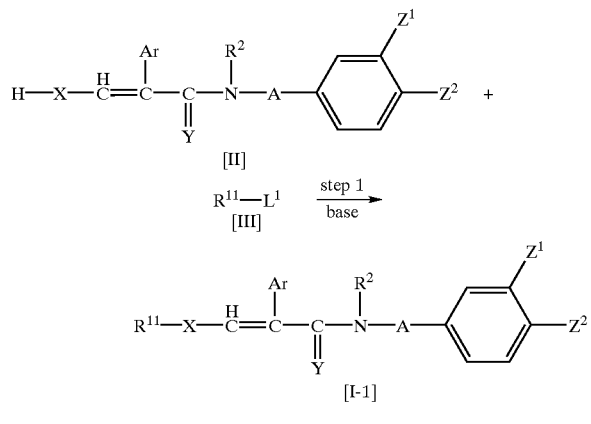

In the above scheme, $L^1$ represents a leaving group such as chlorine, bromine, iodine, p-toluenesulfonyloxy, methanesulfonyloxy and trifluoromethanesulfonyl; $R^{11}$ represents C1–C10 haloalkyl group such as fluoromethyl, difluoromethyl, bromodifluoromethyl and fluoroethoxy, C3–C10 haloalkenyl group such as 3,3-dichloroally or C3–C10 haloalkynyl group such as 2-propynyl; and $R^2$, X, Y, Ar, A, $Z^1$ and $Z^2$ have the same meanings as defined above.

Step 1 (process 1) in the above scheme is a process for producing the present compound given by formula [I-1] by making the compound given by formula [II] react with the compound given by formula [III] optionally in the presence of a base. The reaction temperature is usually in the range of 0–100° C. and the reaction period is usually in the range of 1–24 hours. The amount of the compound given by formula [III] utilized for the reaction is usually 0.5–10 mols, preferably 1–3 mols based on 1 mol of the compound given by formula [II].

When the base is utilized for the reaction, the amount of the base is usually 1–10 mols moles based on 1 mol of the compound given by formula [II]. Examples of the base include inorganic bases such as sodium hydroxide, potassium hydroxide, sodium carbonate, potassium carbonate, sodium hydride and the like; organic bases such as pyridine, triethylamine, ethyldiisopropylamine and the like; and mixtures thereof.

The reaction is usually carried out in a solvent. Examples of the solvent include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; organic bases such as pyridine, triethylamine and N,N-dimethylaniline; esters such as butyl acetate and ethyl acetate; nitrites such as acetonitrile; N,N-dimethylformamide; dimethyl sulfoxide; water; and mixtures thereof.

The reaction solution after the reaction is subjected to usual work-up such as extraction with organic solvent, concentration and so on to provide the isolated objective product. The objective product can be purified by recrystallization, distillation, chromatography and so on.

The compound given by formula [I] wherein $R^1$ is trifluoromethyl can be prepared according to the methods described in Tetrahydron Lett., 1973, 2253 and J. Org. Chem., 1979, 44, 3872. At that time, Production Example 15 given below can be comferred.

The compound given by formula [II] wherein X is oxygen and Y is also oxygen (the compound given by formula [II-1] in the scheme below) can be prepared according to the methods described in Chem. Ber., 1971, 104, 2709, J. Org. Chem., 1966, 61, 3358 and Adv. Heterocycl. Chem., 1981, 31, 207. It can be concretely produced according to the following scheme.

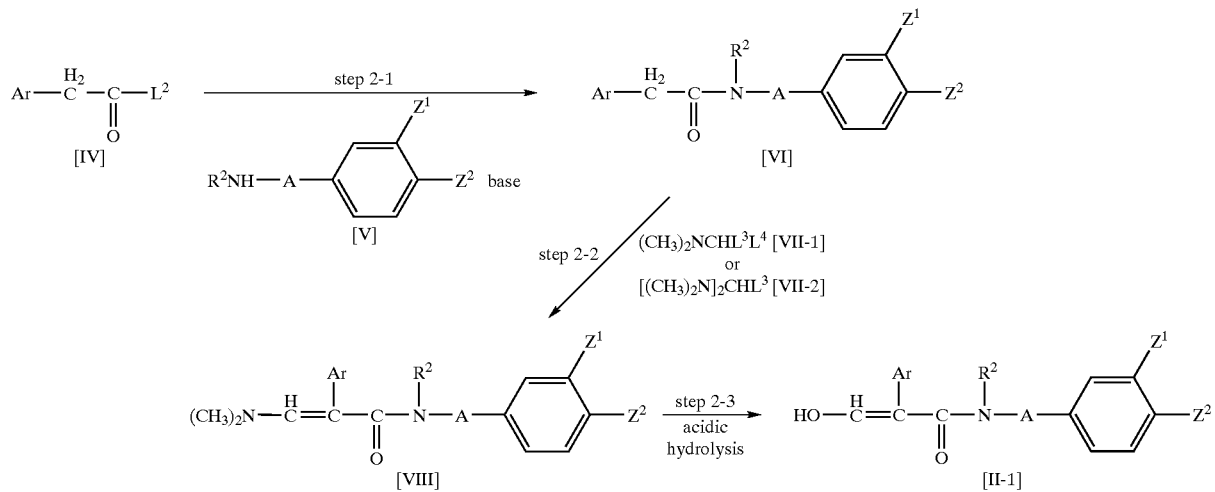

In the above scheme, $L^3$ and $L^4$ are the same or different and represent alkoxy group such as t-butoxy group; $L^2$ represents chlorine or bromine atom; and $R^2$, Ar A, $Z^1$ and $Z^2$ have the same meanings as defined above.

The step 2-1 is a step of making the compound given by formula [IV] react with the compound given by formula [V] in the presence of a base to provide the compound given by formula [VI]. The reaction temperature is usually in the range of 0 to 100° C. and the amount of the compound given by formula [V] is usually 1 to 5 mols based on 1 mol of the compound given by formula [IV].

The amount of the base used for the reaction is usually 1 to 10 mols based on 1 mol of the compound given by formula [IV]. Examples of the base include inorganic bases such as sodium hydroxide, potassium hydroxide, sodium carbonate, potassium carbonate and sodium hydride; organic bases such as pyridine, triethylamine and ethyldiisopropylamine; and mixtures thereof.

The reaction is usually carried out in a solvent and examples of the solvent include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; organic bases such as pyridine, triethylamine and N,N-dimethylaniline; esters such as butyl acetate and ethyl acetate; nitrites such as acetonitrile; N,N-dimethylformamide; dimethyl sulfoxide; water; and mixtures thereof.

The reaction solution after the reaction is subjected to usual work-up such as extraction with organic solvent, concentration and so on to provide the isolated objective product. The objective product can be purified by recrystallization, distillation, chromatography and so on.

The step 2-2 is a step of making the compound given by formula [VI] react with the compound given by formula [VII-1] or formula [VII-2] to provide the compound given by formula [VIII]. The reaction temperature is usually in the range of 50 to 150° C., the reaction period is usually in the range of 1 to 24 hours and the amount of the compound given by formula [VII-1] or formula [VII-2] is usually 1 to 10 mols based on 1 mol of the compound given by formula [VI].

The reaction is usually carried out in a solvent and examples of the solvent include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; organic bases such as pyridine, triethylamine and N,N-dimethylaniline; nitrites such as acetonitrile; N,N-dimethylformamide; dimethyl sulfoxide; and mixtures thereof.

The reaction solution after the reaction is subjected to usual work-up such as extraction with organic solvent, concentration and so on to provide the isolated objective product. The objective product can be purified by recrystallization, distillation, chromatography and so on.

The step 2-3 is a step of making the compound given by formula [VIII] react with excess water in the presence of an acid to provide the compound given by formula [II-1]. The reaction temperature is usually in the range of 0 to 100° C. and examples of the acid include hydrochloric acid, sulfuric acid and p-toluenesulfonic acid. The amount of the acid is usually 0.1 to 100 mols based on 1 mol of the compound given by formula [VIII].

The reaction can be carried out in a solvent and examples of the solvent include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; nitriles such as acetonitrile; N,N-dimethylformamide; dimethyl sulfoxide; and mixtures thereof.

The reaction solution after the reaction is subjected to usual work-up such as extraction with organic solvent, concentration and so on to provide the isolated objective product. The objective product can be purified by recrystallization, distillation, chromatography and so on.

Production Method B

Production method of making the compound given by formula [I-1] to react with 2,4-bis(4-methoxyphenyl)-1,3-dithia-2,4-diphosphetane-2,4-disulfide (hereinafter, referred to as Lawesson's Reagent)

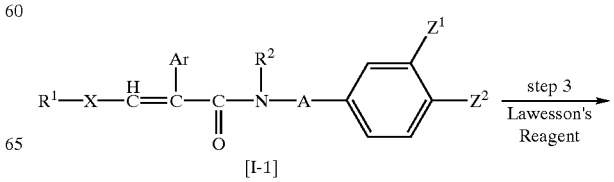

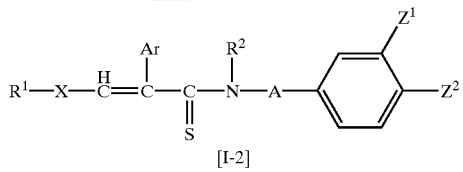

[I-2]

In the above scheme, $R^1$, $R^2$, X, Ar, A, $Z^1$ and $Z^2$ have the same meanings as defined above.

The step 3 is a step of making the compound given by formula [I-1] react with Lawesson's Reagent in a solvent to provide the compound given by formula [I-2]. The reaction temperature is usually in the range of 50 to 150° C. and the amount of the Lawesson's Reagent is usually 1 to 10 mols based on 1 mol of the compound given by formula [I-1].

Examples of the solvent used for the reaction include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; organic bases such as pyridine, triethylamine and N,N-dimethylaniline; nitriles such as acetonitrile; N,N-dimethylformamide; dimethyl sulfoxide; and mixtures thereof.

The reaction solution after the reaction is subjected to usual work-up such as extraction with organic solvent, concentration and so on to provide the isolated objective product. The objective product can be purified by recrystallization, distillation, chromatography and so on.

Production Method C

Production method of making the compound given by formula [IX] to react with the compound given by formula [X]

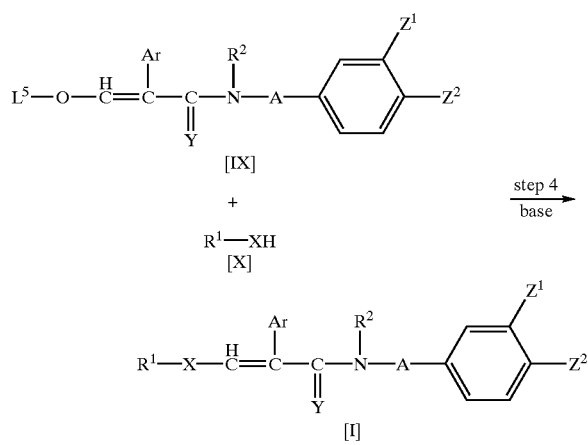

In the above scheme, $L^5$ represents p-toluenesulfonyl, methanesulfonyl or trifluoromethanesulfonyl, and $R^1$, $R^2$, Y, Ar, A, $Z^1$ and $Z^2$ have the same meanings as defined above.

The step 4 is a step of making the compound given by formula [IX] react with the compound given by formula [X]optionally in the presence of a base to provide the present compound given by formula [I]. The reaction temperature is usually in the range of 0 to 100° C., the reaction period is usually in the range of 1 to 24 hours and the amount of the compound given by formula [X] is usually 0.5 to 10 mols, preferably 1 to 3 mols based on 1 mol of the compound given by formula [IX].

When the base is utilized in the above reaction, the amount of the base is usually 1 to 10 mols based on 1 mol of the compound given by formula [X]. Examples of the base include inorganic bases such as sodium hydroxide, potassium hydroxide, sodium carbonate, potassium carbonate and sodium hydride; organic bases such as pyridine, triethylamine and ethyldiisopropylamine; and mixtures thereof.

The reaction is usually carried out in a solent and examples of the solvent include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; organic bases such as pyridine, triethylamine and N,N-dimethylaniline; esters such as butyl acetate and ethyl acetate; nitriles such as acetonitrile; N,N-dimethylformamide; dimethyl sulfoxide; water; and mixtures thereof.

The reaction solution after the reaction is subjected to usual work-up such as extraction with organic solvent, concentration and so on to provide the isolated objective product. The objective product can be purified by recrystallization, distillation, chromatography and so on.

The compound given by formula [IX] can be, for example, produced according to the following scheme.

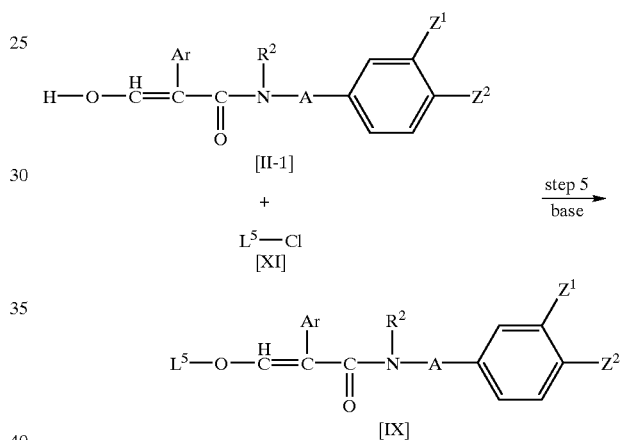

In the above scheme, $L^5$, $R^2$, Ar, A, $Z^1$ and $Z^2$ have the same meanings as defined above.

The step 5 is a step of making the compound given by formula [II-1] react with the compound given by formula [X]optionally in the presence of a base to provide the present compound given by formula [IX]. The reaction temperature is usually in the range of −20 to 100° C., the reaction period is usually in the range of 1 to 24 hours and the amount of the compound given by formula [XI] is usually 0.5 to 10 mols, preferably 1 to 3 mols based on 1 mol of the compound given by formula [IX].

When the base is utilized in the above reaction, the amount of the base is usually 1 to 10 mols based on 1 mol of the compound given by formula [II-1]. Examples of the base include inorganic bases such as sodium hydroxide, potassium hydroxide, sodium carbonate, potassium carbonate and sodium hydride; organic bases such as pyridine, triethylamine and ethyldiisopropylamine; and mixtures thereof.

The reaction is usually carried out in a solent and examples of the solvent include ethers such as 1,4-dioxane, tetrahydrofuran, ethylene glycol dimethyl ether and t-butyl methyl ether; aliphatic hydrocarbons such as hexane and heptane; aromatic hydrocarbons such as toluene; halogenated hydrocarbons such as chlorobenzene; organic bases such as pyridine, triethylamine and N,N-dimethylaniline;

esters such as butyl acetate and ethyl acetate; nitriles such as acetonitrile; N,N-dimethylformamide; dimethyl sulfoxide; water; and mixtures thereof.

The reaction solution after the reaction is subjected to usual work-up such as extraction with organic solvent, concentration and so on to provide the isolated objective product. The objective product can be purified by recrystallization, distillation, chromatography and so on.

The compound given by formula [IV] can be, for example, produced according to the following scheme.

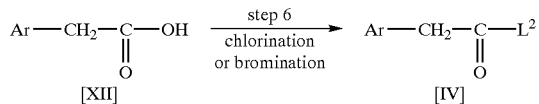

wherein L² and Ar mean as described above.

The compound given by formula [XII] can be produced according to the description in Syn. Commun., 1982, 21, 415, JP sho58-41862A, Tetrahedron Lett., 1980,21,2547, Syn. Commun., 1976, 6, 349 and J. Am. Chem. Soc., 1977, 99, 4833.

The compound given by formula [V] can be produced according to the description in Bull. Chem. Soc, Jpn., 1990, 63, 1252, J. Am. Chem. Soc., 1955, 77, 2544, Synthesis, 1975, 590 and Chem. Lett., 1984, 1733.

When the present compound is used as an active ingredient of fungicide, it can be used as it is without any other ingredient, but it is usually formulated to emulsifiable concentrates, wettable powders, water dispersible granules, emulsion formulations, flowables, dusts, granules and so on by mixing with solid carrier, liquid carrier, surfactant or the other auxiliaries and used. These formulations usually contain 0.1 to 90% by weight of the present compound.

Examples of the solid carrier utilized for the formulation include fine powders or granules of minerals such as kaolin clay, attapulgite clay, bentonite, montmorillonite, terra alba, pyrophilite, talc, diatomaceous earth and calcite; natural organic substances such as corncob and walnut shell; synthetic organic substances such as urea; salts such as calcium carbonate and ammonium sulfate; and synthetic inorganic substances such as synthetic hydrous silicon oxide. Examples of the liquid carrier include aromatic hydrocarbons such as xylene, alkylbenzene and methylnaphthalene; alcohols such as isopropanol, ethylene glycol, propylene glycol and cellosolve; ketones such as acetone, cyclohexanone and isophorone; vegetable oils such as soybean oil and cottonseed oil; paraffin type aliphatic hydrocarbons; esters; dimethyl sulfoxide; acetonitrile and water.

Examples of the surfactant include anionic surfactants such as alkylsulfate ester salts, alkylarylsulfonate salts, dialkyl sulfosaccinate salts, polyoxyethylenealkylary ether phosphate salts, ligninsulfonate salts and naphthalenesulfonate formaldehyde condensate; nonionic surfactants such as polyoxyethylenealkylary ether, polyoxyethylenealkylpolyoxypropylene block copolymers and sorbitan fatty acid esters.

Examples of the auxiliaries for formulation include water soluble polymers such as polyvinyl alcohol and polyvinylpyrrolidone; polysaccharides such as gum arabic, algin acid and its salts, CMC(carboxymethylcellulose) and xanthan gum; inorganic substances such as alminium magnesium silicate and almina sol; preservatives; coloring agent; PAP (isopropyl acid phosphate) and stabilizers such as BHT.

The application methods of the present compounds are typically foliar application and soil treatment.

When the present compound is used for controlling plant diseases, the dosage is usually 1 to 5000 g, preferably 5 to 1000 g per 1 hectare though it is variable depending on the type of plants (e.g. crops) to be treated, type of diseases to be controlled, degree of affection by the diseases, formulation type, application method, time of application, weather conditions and so on.

In case emulsifiable concentrates, wettable powders, flowables and the like are used as aqueous dilution, the concentration of the active ingredient is 0.0001 to 3% by weight, preferably 0.0005 to 1% by weight. Dusts, granules and the like are applied as they are without dilution. The present compound is also used for the other known application methods such as seed treatment. When it is used for seed treatment, seeds are usually soaked in 1 to 1000 ppm dilution of the present compound, or said dilution is sprayed to or daubed on the seeds. Further, dusts containing 0.1 to 10% by weight of the present compound may be applied by powder treatment.

The present compound can be used as agricultural/horticultural fungicide for controlling plant diseases in the plowed fields, paddy fields, orchards, tea plantations, pastures, lawns and the like. Also, an increased fungicidal effect can be expected by using the compounds in admixture with other fungicides. Examples of such admixable other fungicide include azole type fungicidal compounds such as propiconazole, triadimenol, prochloraz, penconazole, tebuconazole, flusilazole, diniconazole, bromconazole, epoxyconazole, diphenoconazole, ciproconazole, metoconazole, triflumizole, tetraconazole, microbutanil, fenbuconazole, hexaconazole, fluquinconazole, triticonazole, bitertanol, imazalil and flutriafol; cyclic amine type fungicidal compounds such as fenpropimorph, tridemorph and fenpropidin; benzimidazole type fungicidal compounds such as carbendazim, benomyl, thiabendazole and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanide; folpet; kresoxim-methyl; azoxystrobin; trifloxystrobin; picoxystrobin; pyraclostrobin; N-methyl-α-ethoxyimino-2-[(2,5-dimethylphenoxy)methyl]phenylactamide, spiroxamine; quinoxyfen; phenhexamid; famoxadone; fenamidon (RP-407213) and iprovalicarb.

The present compound can be used in combination with other agricultural/horticultural insecticides, acaricides, nematocides, herbicides, plant growth regulators and fertilizers. In the combination, they can be mixed in advance.

Examples of the insecticide, acaricide and nematocide include organophosphorus compounds such as fenitrothion [O,O-dimethyl O-(3-methyl-4-nitrophenyl) phosphorothioate], fenthion [O,O-dimethyl O-(3-methyl-4-(methythio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramidothioate], methidathion [S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phosphorodithioate], DDVP [2,2-dichlorovinyl dimethyl phosphate], sulprofos [O-ethyl O-4-(methylthio)phenyl S-propyl phosphorodithioate], cyanophos [O-4-cyanophenyl O,O-dimethyl phosphorothioate], dioxabenzofos [2-methoxy-4H-1,3,2-benzodioxaphosphorin 2-sulfide], dimethoate [O,O-dimethyl S-(N-methylcarbamoylmethyl) dithiophosphate], phenthoate [ethyl 2-dimethoxyphosphinothioylthio(phenyl) acetate], malathion [diethyl (dimethoxyphosphinothioylthio) succinate], trichlorfon

[dimethyl 2,2,2-trichloro-1-hydroxyethylphosphonate], azinphos-methyl [S-3,4-dihydro-4-oxo-1,2,3-benzotriazin-3-ylmethyl O,O-dimethyl phosphorodithioate], monocrotophos [dimethyl (E)-1-methyl-2-(methylcarbamoyl) vinyl phosphate], ethion [O,O,O',O'-tetraethyl S,S'-methylene bis (phosphorodithioate)] and fosthiazate [N-(O-methyl-S-sec-butyl) phosphorylthiazolidin-2-one]; carbamate compounds such as BPMC [2-sec-butylphenyl methylcarbamate], benfracarb [ethyl N-[2,3-dihydro-2,2-dimethylbenzofuran-7-yloxycarbonyl(methyl)aminothio]-N-isopropyl-β-alaninate], propoxur [2-isopropoxyphenyl N-methylcarbamate], carbosulfan [2,3-dihydro-2,2-dimethyl-7-benzo [b]furanyl N-dibuthylaminothio-N-methylcarbamate], carbaryl [1-naphthyl N-methylcarbamate], methomyl [S-methyl N-[(methylcarbamoyl)oxy]thioacetimidate], ethiofencarb [2-(ethylthiomethyl) phenyl methylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide] and fenothiocarb [S-4-phenoxybuthyl N,N-dimethylthiocarbamate]; pyrethroid compounds such as etofenprox [2-(4-ethoxyphenyl)-2-methylpropyl 3-phenoxybenzyl ether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS, 3RS)-3-(2,2-dichlorovinyl)-2,2-dimethyl-cyclopropanecarboxylate], permethrin [3-phenoxybenzyl (1RS,3RS)-3-(2,2-dichlorovinyl)-2,2-dimethylcyclopropanecarboxylate], cyhalothrin [(RS)-α-cyano-3-phenoxybenzyl (Z)-(1RS, 3RS)-3-(2-chloro-3,3,3-trifluoropropenyl)-2,2-dimethylcyclopropanecarboxylate], deltamethrin [(S)-α-cyano-m-phenoxybenzyl (1R,3R)-3-(2,2-dibromovinyl)-2,2-dimethyl-cyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate [α-cyano-3-phenoxybenzyl N-(2-chloro-α,α,α-trifluoro-p-tolyl)-D-valinate], bifenthrin [2-methylbiphenyl-3-ylmethyl (Z)-(1RS)-cis-3-(2-chloro-3,3,3-trifluoroprop-1-enyl)-2,2-dimethyl-cyclopropanecarboxylate]acrinathrin [cyano(3-phenoxyphenyl)methyl (1R-{1α(S*), 3α(Z)})-2,2-dimethyl-3-[3-oxo-3-(2,2,2-trifluoro-1-(trifluoromethyl)ethoxy-1-propenyl)cyclopropanecarboxylate], 2-methyl-2-(4-bromodifluoromethoxyphenyl) propyl 3-phenoxybenzyl ether, tralomethrin [(S)-α-cyano-3-phenoxybenzyl (1R-cis) 3-(1,2,2,2-tetrabromoethyl)-2,2-dimethylcyclopropanecarboxylate], silafluofen [(4-ethoxyphenyl)(3-(4-fluoro-3-phenoxyphenyl)propyl) dimethylsilane]; thiadiazine derivatives such as buprofezin (2-t-butylimino-3-isopropyl-5-phenyl-1,3,5-thiadiazin-4-one); nitroimidazolidine derivatives; nereistoxin derivatives such as cartap (S,S'-(2-dimethylaminotrimethylene)bis (thiocarbamate), thiocyclam [N,N'-dimethyl-1,2,3-trithian-5-ylamine] and bensultap [S,S'-2-dimethylaminotrimethylene di(benzenethiosulfonate)]; N-cyanoamidine derivatives such as N-cyano-N'-methyl-N'-(6-chloro-3-pyridylmethyl)acetamidine; chlorinated hydrocarbons such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane] and 1,1-bis(chlorophenyl)-2,2,2-trichloroethanol; benzoylphenylurea compounds such as chlorfluazuron [1-(3,5-dichloro-4-(3-chloro-5-trifluoromethylpyridyn-2-yloxy)phenyl)-3-(2,6-difluorobenzoyl)urea], teflubenzuron [1-(3,5-dichloro-2,4-difluorophenyl)-3-(2,6-difluorobenzoyl)urea] and flufenoxuron [1-(4-(2-chloro-4-trifluoromethylphenoxy)-2-fluorophenyl)-3-(2,6-difluorobenzoyl)urea]; formamidine derivatives such as amitraz [N,N'-[(methylimino) dimethylidine]di-2,4-xylidine] and chlordimeform [N'-(4-chloro-2-methylphenyl)-N,N-dimethylmethanimidamide]; thiourea derivatives such as diafenthiuron [N-(2,6-diisopropyl-4-phenoxyphenyl)-N'-t-butylcarbodiimide]; phenylpyrazole compounds; tebufenozide [N-t-butyl-N'-(4-ethylbenzoyl)-3,5-dimethylbenzhydrazide]; 4-bromo-2-(4-chlorophenyl)-1-ethoxymethyl-5-trifluoromethylpyrrole-3-carbonitrile; bromopropylate [isopropyl 4,4'-dibromobenzilate]; tetradifon [4-chlorophenyl 2,4,5-trichlorophenyl sulfone]; quinomethionate [S,S-6-methylquinoxalin-2,3-diyl dithiocarbonate]; propargite [2-(4-t-butylphenoxy)cyclohexyl prop-2-yl sulfite]; fenbutatin oxide [bis[tris (2-methyl-2-phenylpropyl)tin]oxide]; hexythiazox [(4RS, 5RS)-5-(4-chlorophenyl)-N-chlorohexyl-4-methyl-2-oxo-1,3-thiazolidin-3-carboxamide]; clofentezine [3,6-bis(2-chlorophenyl)-1,2,4,5-tetrazine]; pyridathioben [2-t-butyl-5-(4-t-butylbenzylthio)-4-chloropyridazin-3(2H)-one]; fenpyroximate [t-butyl (E)-4-[(1,3-dimethyl-5-phenoxypyrazol-4-yl)methyleneaminooxymethyl] benzoate]; tebufenpyrad [N-(4-t-butylbenzyl)-4-chloro-3-ethyl-1-methyl-5-pyrazolecarboxamide]; polynactins complex [tetranactin, dinactin and trinactin]; milbemectin; abamectin; ivermectin; azadirachtin [AZAD]; pyrimidifen [5-chloro-N-[2-{4-(2-ethoxyethyl)-2,3-dimethylphenoxy}ethyl]-6-ethylpyrimidin-4-amine] and pymetrozine [2,3,4,5-tetrahydro-3-oxo-4-[(pyridin-3-yl) methyleneamino]-6-methyl-1,2,4-triazine.

Examples of the plant diseases to be controlled by the present compound include *Pyricularia oryzae* and *Cochlioholus miyaheanus* and *Rhizoctonia solani* of rice; *Erysiphe graminis, Gibberella zeae, Puccinia striiformis, P. graminis, P. recondita, P. hordei*, Typhula sp., *Micronectriella nivalis, Ustilago tritici, U. nuda, Tilletia caries, Pseudocercosporella herpotrichoides, Rhynchosporium secalis, Septoria tritici* and *Leptosphaeria nodorum*, of wheat and barley; *Diaporthe citri, Elsinoe fawcetti, Penicillium digitatum* and *P. italicum* of citrus; *Sclerotinia mali, Valsa mali, Podosphaera leucotricha, Alternaria mali* and *Venturia inaequalis* of apple; *Venturia nashicola, V. pirina, Alternaria kikuchiana* and *Gymnosporangium haraeanum* of pear; *Sclerotinia cinerea, Cladosporium carpophilum* and *Phomopsis* sp. of peach; *Elsinoe ampelina, Glomerella cingulata, Uncinula necator, Phakopsora ampelopsidis, Guignardia bidwellii* and *Plasmopara viticola*, of grape; *Gloeosporium kaki, Cercospora kaki* and *Mycosphaerella nawae* of Japanese persimmon; *Colletotrichum lagenarium, Sphaerotheca fuliginea, Mycosphaerella melonis, Fusarium oxysporum, Pseudoperonospora cubensis* and Phytophthora sp. of gourd; *Alternaria solani, Cladosporium fulvum, Phytophthora infestans* and Pythium sp. of tomato; *Phomopsis vexans* and *Erysiphe cichoracearum*, of eggplant; *Alternaria japonica* and *Cercosporella brassicae* of Cruciferae vegetables; *Puccinia allii* of leek; *Cercospora kikuchii, Elsinoe glycines* and *Diaporthe phaseolorum var. sojae* of soybean; *Colletotrichum lindemthianum* of kidney bean; *Cercospora personata* and *Cercospora arachidicola* of peanut; *Erysiphe pisi* of pea; *Alternaria solani* and *Phytophthora infestans* of potato; *Sphaerotheca humuli* of strawberry; *Exobasidium reticulatum* and *Elsinoe leucospila* of tea; *Alternaria longipes, Erysiphe cichoracearum, Colletotrichum tabacum, Peronospora tabacina* and *Phytophthora nicoti-* anae of tobacco; *Cercospora beticola* of sugar beet; *Diplocarpon rosae* and *Sphaerotheca pannosa* of rose; *Septoria chrysanthemi-indici* and *Puccinia horiana* of chrysanthemum; and *Botrytis cinerea* and *Sclerotinia sclerotiorum* of various crops.

EXAMPLES

The present invention is explained by production examples, formulation examples and test examples below and it is not restricted by the following examples.

At first, the production examples of the present compounds and reference production examples of the intermediates of the present compounds. The numbers of the present compounds are the compound numbers described in the table below.

Production Example 1

Two hundred milligrams (200 mg) of N-[2-(3,4-dimethoxyphenyl)ethyl]-3-hydroxy-2-(4-methylphenyl) acrylamide (0.586 mmol), 28 mg (0.70 mmol) of 60% sodium hydride, 2 ml of anhydrous N,N-dimethylformamide and 1 ml of anhydrous diethyl ether were mixed and 0.5 ml of bromofluoromethane was added thereto at −5° C. The mixture was stirred at −5° C. for 30 minutes and then stirred at 0° C. for 1 hour. The reaction mixture was added to water and extracted with ethyl acetate. The organic layer was washed with 5% hydrochloric acid, saturated aqueous sodium bicarbonate solution and saturated brine subsequently, dried over anhydrous magnesium sulfate and concentrated under reduced pressure. The residue was subjected to silica gel preparative thin layer chromatography (eluent, hexane:ethyl acetate=2:1) to give 205 mg of N-[2-(3,4-dimethoxyphenyl)ethyl]-3-fluoromethoxy-2-(4-methylphenyl)acrylamide (the present compound 1-4).

$^1$H-NMR(CDCl$_3$, TMS) δ(ppm): 7.1–7.2(5H,m), 6.7–6.8 (3H,m), 6.5(1H,s), 5.43(2H,d,J=53 Hz), 3.87(3H,s), 3.85 (3H,s), 3.62(2H,m), 2.84(2H,t), 2.34(3H,s).

By using N-[2-(3,4-dimethoxyphenyl)ethyl]-3-hydroxy-2-(3-methylphenyl) acrylamide in place of N-[2-(3,4-dimethoxyphenyl)ethyl]-3-hydroxy-2-(4-methylphenyl) acrylamide, N-[2-(3,4-dimethoxyphenyl)ethyl]-3-fluoromethoxy-2-(3-methylphenyl)acrylamide (the present compound 1034) was obtained according to production example 1.

$^1$H-NMR(CDCl$_3$, TMS) δ(ppm): 7.0–7.3(4H,m), 6.6–6.8 (4H,m), 6.46(1H,br), 5.44(2H,d,J=53.4 Hz), 3.86(3H,s), 3.85(3H,s), 3.6–3.7(2H,m), 2.84(2H,t,J=6.9 Hz), 2.33(3H,s)

Production Example 2

Five hundred milligrams (500 mg) of N-[2-(3,4-dimethoxyphenyl)ethyl]-3-hydroxy-2-(4-methylphenyl) acrylamide (1.46 mmol), 0.31 g (1.7 mmol) of 30% aqueous potassium hydroxide solution, 0.1 g (0.3 mmol) of tetrabutylammonium bromide and 10 ml of ethylene glycol dimethyl ether were mixed and chlorodifluoromethane gas was blown thereto at room temperature. After a small amount of 30% aqueous potassium hydroxide solution was further added, a sample was taken out from the reaction mixture and the disappearance of the starting material was confirmed by thin layer chromatograph analysis. Then, 5% hydrochrolic acid was added to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was washed with hexane to give 474 mg of N-[2-(3,4-dimethoxyphenyl) ethyl]-3-difluoromethoxy-2-(4-methylphenyl)acrylamide (the present compound 1005).

$^1$H-NMR(CDCl$_3$, TMS) δ(ppm): 7.11–7.19(4H,m), 6.85 (1H,s), 6.72–6.78 (3H,m), 6.36(1H,t,J=71.8 Hz), 3.86(3H,s), 3.83(3H,s), 3.49(2H,m), 2.83(2H,t), 2.34(3H,s)

Production Example 3

One gram (1.00 g) of N-[2-(3,4-dimethoxyphenyl)ethyl]-3-hydroxy-2-(4-chlorophenyl) acrylamide (2.66 mmol), 130 mg (3.25 mmol) of 60% sodium hydride and 10 ml of anhydrous N,N-dimethylformamide were mixed and 0.46 g of bromofluoromethane was added thereto at −15° C. The mixture was stirred at −15° C. for 30 minutes and then stirred at 0° C. for 1 hour. The reaction mixture was added to water and extracted with ethyl acetate. The organic layer was washed with 5% hydrochloric acid and saturated brine subsequently, dried over anhydrous magnesium sulfate and concentrated under reduced pressure. The residue was subjected to silica gel preparative thin layer chromatography (eluent, hexane:ethyl acetate=1:1) to give 100 mg of N-[2-(3,4-dimethoxyphenyl)ethyl]-3-fluoromethoxy-2-(4-chlorophenyl)acrylamide (the present compound 1016).

$^1$H-NMR(CDCl$_3$, TMS) δ(ppm): 7.0–7.3(4H,m), 6.5–6.8 (5H,m), 5.41(2H,d, J=53.4 Hz), 3.84(3H,s), 3.83(3H,s), 3.5–3.7(2H,m), 2.82(2H,t,J=6.9 Hz)

Production Example 4

Five hundred milligrams (500 mg) of N-[2-(3,4-dimethoxyphenyl)ethyl]-3-hydroxy-2-(4-chlorophenyl) acrylamide (1.33 mmol), 2.00 g (3.56 mmol) of 10% aqueous potassium hydroxide solution, 87 mg (0.266 mmol) of tetrabutylammonium bromide and 10 ml of ethylene glycol dimethyl ether were mixed and chlorodifluoromethane gas was blown thereto at room temperature. After a sample was taken out from the reaction mixture and the disappearance of the starting material was confirmed by thin layer chromatograph analysis, 5% hydrochloric acid was added to the reaction mixture. The reaction mixture was extracted with ethyl acetate, washed with 5% hydrochloric acid, saturated aqueous sodium bicarbonate solution and saturated brine subsequently, dried over anhydrous magnesium sulfate and concentrated under reduced pressure. The residue was subjected to silica gel chromatography (eluent, hexane:ethyl acetate=2:1) and the obtained residue was washed with hexane to give 360 mg of N-[2-(3,4-dimethoxyphenyl) ethyl]-3-difluoromethoxy-2-(4-chlorophenyl)acrylamide.

$^1$H-NMR(CDCl$_3$, TMS) δ(ppm): 7.2–7.4(4H,m), 6.7–6.9 (4H,m), 6.35(1H,t, J=71.4 Hz), 6.13(1H,br), 3.86(3H,s), 3.83(3H,s), 3.6–3.7(2H,m), 2.84(2H,t, J=6.8 Hz).

Production Example 5

Five hundred miligrams (500 mg) of N-[2-(3,4-dimethoxyphenyl)ethyl]-3-hydroxy-2-(4-methylphenyl) acrylamide (1.47 mmol), 0.11 g (1.47 mmol) of 3-chloropropyne and 5 ml of anhydrous N,N-dimethylformamide were mixed and 64 mg (1.61 mmol) of 60% sodium hydride was added thereto at 0–5° C. The mixture was stirred at 0–10° C. for 30 minutes and then stirred at room temperature. Water was added to the reaction mixture, followed by extracted with ethyl acetate, washed with 5% hydrochrolic acid and saturated brine subsequently, dried over anhydrous magnesium sulfate and concentrated under reduced pressure. The residue was subjected to silica gel chromatography (eluent, hexane:ethyl acetate=1:1) to give 180 mg of N-[2-(3,4-dimethoxyphenyl)ethyl]-3-(2-propynyloxy)-2-(4-methylphenyl)acrylamide (the present compound 1182).

$^1$H-NMR(CDCl$_3$, TMS) δ(ppm): 7.0–7.3(4H,m), 6.7–6.9 (4H,m), 6.70(1H,s), 4.51(2H,d,J=2.4 Hz), 3.86(6H,s), 3.5–3.7(2H,m), 2.83(2H,t,J=6.9 Hz), 2.59(1H,t, J=2.4 Hz), 2.32(3H,s).

By using N-[2-(3,4-dimethoxyphenyl)ethyl]-3-hydroxy-2-(4-chlorophenyl) acrylamide in place of N-[2-(3,4-dimethoxyphenyl)ethyl]-3-hydroxy-2-(4-methylphenyl) acrylamide, N-[2-(3,4-dimethoxyphenyl)ethyl]-3-(2-propynyloxy)-2-(4-chlorophenyl)acrylamide (the present compound 1185) was obtained according to production example 5.

$^1$H-NMR(CDCl$_3$, TMS) δ(ppm): 7.60(1H,s), 7.2–7.4(4H, m), 7.0–7.1(2H,m), 6.73(1H,d,J=7.9 Hz), 6.62(1H,d,J=1.9 Hz), 6.56(1H,dd,J=8.0,1.9 Hz), 5.28(1H,br), 4.52(2H,d,J=2.3 Hz), 3.87(3H,s), 3.83(3H,s), 3.4–3.6(2H,m), 2.71(2H,t, J=6.9 Hz)

Production Example 6

0.76 g (2.0 mmol) of N-[2-(3,4-dimethoxyphenyl)ethyl]-3-hydroxy-2-(5,6,7,8-tetrahydronaphthalen-2-yl)acrylamide and 8ml of anhydrous N,N-dimethylformamide were mixed and 0.5 ml of bromofluoromethane was added thereto at −15° C. 88 mg (2.2 mmol) of 60% sodium hydride was added and stirred at −15° C. for 30 minutes and then stirred at approximately 0° C. for 1.5 hours. Water was added to the reaction mixture, followed by extracted with ethyl acetate, washed with 5% hydrochrolic acid and saturated brine subsequently, dried over anhydrous magnesium sulfate and concentrated under reduced pressure. The residue was subjected to silica gel preparative thin layer chromatography (eluent, hexane:ethyl acetate=1:1) to give 0.68 g of N-[2-(3,4-dimethoxyphenyl)ethyl]-3-fluoromethoxy-2-(5,6,7,8-tetrahydronaphthalen-2-yl)acrylamide(the present compound 1103).

$^1$H-NMR(CDCl$_3$, TMS) δ(ppm): 7.00(3H,s), 6.7–6.9(4H, m), 6.42(1H,br), 5.43(2H,d,J=53.7 Hz), 3.85(3H,s), 3.84 (3H,s), 3.6–3.7(2H,m), 2.83(2H,t,J=6.9 Hz), 2.7–2.8(4H,m), 1.7–1.9(4H,m).

Production Example 7

A mixture of 380 mg (0.920 mmol) of N-[2-(3,4-dimethoxyphenyl)ethyl]-3-fluoromethoxy-2-(5,6,7,8-tetrahydronaphthalen-2-yl)acrylamide, 420 mg (1.01 mmol) of Lawesson's Reagent and 5 ml of anhydrous tetrahydrofuran was refluxed by heating for 3 hours. Water and ethyl acetate were added to the reaction mixture, and the ethyl acetate layer was washed with aqueous sodium hydroxide solution, aqueous ammonium chloride solution and saturated brine subsequently, dried over anhydrous magnesium sulfate and concentrated under reduced pressure. The residue was subjected to silica gel chromatography (eluent, hexane:ethyl acetate=3:1) to give 222 mg of N-[2-(3,4-dimethoxyphenyl)ethyl]-3-fluoromethoxy-2-(5,6,7,8-tetrahydronaphthalen-2-yl)acrylthioamide (the present compound 1160).

$^1$H-NMR(CDCl$_3$, TMS) δ(ppm): 8.11(1H,s), 7.0–7.1(2H, m), 6.77(2H,d, J=6.0 Hz), 6.70(1H,d,J=8.2 Hz), 6.60(1H,d, J=1.7 Hz), 6.55(1H,dd,J=7.9,1.9 Hz), 5.48(2H,d,J=53.5 Hz), 3.9–4.0(2H,m), 3.85(3H,s), 3.81(3H,s), 2.83(2H,t,J=6.7 Hz), 2.6–2.8(4H,m), 1.7–1.9(4H,m).

By using 3-difluoromethoxy-N-[2-{3-methoxy-4-(2-propynyloxy)phenyl}ethyl]-2-(4-methylphenyl)acrylamide in place of N-[2-(3,4-dimethoxyphenyl)ethyl]-3-fluoromethoxy-2-(5,6,7,8-tetrahydronaphthalen-2-yl) acrylamide, 3-difluoromethoxy-N-[2-{3-methoxy-4-(2-propynyloxy)phenyl}ethyl]-2-(4-methylphenyl) acrylthioamide (the present compound 1445) was obtained according to production example 7.

$^1$H-NMR(CDCl$_3$, TMS) δ(ppm): 8.20(1H,s), 7.1–7.2(2H, m), 6.8–7.0(4H,m), 6.38(1H,t, J=71.0 Hz), 6.5–6.6(1H,m), 4.74(2H,s), 3.9–4.0(2H,m), 3.79(3H,s), 2.83(2H,t,J=6.8 Hz), 2.52(1H,t,J=2.1 Hz), 2.39(3H,s).

Production Example 8

Five hundred milligrams (500 mg) of N-[2-(3,4-dimethoxyphenyl)ethyl]-3-hydroxy-2-(5,6,7,8-tetrahydronaphthalen-2-yl)acrylamide (1.31 mmol), 1.80 g (3.28 mmol) of 10% aqueous potassium hydroxide solution, 87 mg (0.262 mmol) of tetrabutylammonium bromide and 10 ml of ethylene glycol dimethyl ether were mixed and chlorodifluoromethane gas was blown thereto at room temperature. A sample was taken out from the reaction mixture and the disappearance of the starting material was confirmed by thin layer chromatograph analysis. Then, 5% hydrochrolic acid was added to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was subjected to silica gel chromatography (eluent, hexane:ethyl acetate=2:1) and the obtained residue was washed with hexane to give 350 mg of 3-difluoromethoxy-N-[2-(3,4-dimethoxyphenyl)ethyl]-2-(5,6,7,8-tetrahydronaphthalen-2-yl)acrylamide (the present compound 1104).

$^1$H-NMR(CDCl$_3$, TMS) δ(ppm): 6.9–7.1(3H,m), 6.7–6.9 (4H,m), 6.36(1H,t, J=71.8 Hz), 6.01(1H,br), 3.86(3H,s), 3.83(3H,s), 3.6–3.7(2H,m), 2.83(2H,t, J=6.9 Hz), 2.6–2.8 (4H,m), 1.7–1.9(4H,m).

By using N-[2-(3,4-dimethoxyphenyl)ethyl]-3-hydroxy-2-(4-methoxyphenyl)acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(4-methoxyphenyl) acrylamide (the present compound 1023) was obtained according to production example 8.

$^1$H-NMR(CDCl$_3$, TMS) δ(ppm): 7.1–7.3(2H,m), 6.7–6.9 (6H,m), 6.35(1H,t, J=71.7 Hz), 6.04(1H,br), 3.86(3H,s), 3.82(3H,s), 3.80(3H,s), 3.6–3.7(2H,m), 2.83 (2H,t,J=6.8 Hz).

By using N-[2-(3,4-dimethoxyphenyl)ethyl]-3-hydroxy-2-(naphthalen-2-yl)acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(naphthalen-2-yl) acrylamide (the present compound 2077) was obtained according to production example 8.

$^1$H-NMR(CDCl$_3$, TMS) δ(ppm): 7.7–7.9(4H,m), 7.4–7.6 (3H,m), 7.01(1H,s), 6.7–6.8(3H,m), 6.41(1H,t,J=71.6 Hz), 6.08(1H,br), 3.84(3H,s), 3.79(3H,s), 3.6–3.7(2H,m), 2.86 (2H,t,J=6.9 Hz).

By using N-[2-(3,4-dimethoxyphenyl)ethyl]-3-hydroxy-2-(4-bromophenyl) acrylamide in place of N-[2-(3,4-dimethoxyphenyl)ethyl]-3-hydroxy-2-(5,6,7,8-tetrahydronaphthalen-2-yl)acrylamide, 2-(4-bromophenyl)-3-difluoromethoxy-N-[2-(3,4-dimethoxyphenyl)ethyl] acrylamide (the present compound 1020) was obtained according to production example 8.

$^1$H-NMR(CDCl$_3$, TMS) δ(ppm): 7.4–7.5(2H,m), 7.1–7.2 (2H,m), 6.89(1H,s), 6.7–6.9(3H,m), 6.35(1H,t,J=71.4 Hz), 6.14(1H,br), 3.86(3H,s), 3.83(3H,s), 3.6–3.7(2H,m), 2.84 (2H,t,J=6.9 Hz).

By using N-[2-(3,4-dimethoxyphenyl)ethyl]-3-hydroxy-2-(4-trifluoromethylphenyl)acrylamide in place of N-[2-(3, 4-dimethoxyphenyl) ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(4-trifluoromethylphenyl) acrylamide (the present compound 1029) was obtained according to production example 8.

$^1$H-NMR(CDCl$_3$, TMS) δ(ppm): 7.4–7.6(4H,m), 6.95 (1H,s), 6.7–6.9(3H,m), 6.37(1H,t,J=71.5 Hz), 6.21(1H,br), 3.85(3H,s), 3.83(3H,s), 3.6–3.7(2H,m), 2.85(2H,t,J=6.9 Hz).

By using N-[2-(3,4-dimethoxyphenyl)ethyl]-3-hydroxy-2-(indan-5-yl) acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(indan-5-yl) acrylamide (the present compound 1122) was obtained according to production example 8.

$^1$H-NMR(CDCl$_3$, TMS) δ(ppm): 7.0–7.2(3H,m), 6.6–6.9 (4H,m), 6.35(1H,t, 71.7 Hz), 6.02(1H,br), 3.85(3H,s), 3.83 (3H,s), 3.6–3.7(2H,m), 2.8–3.0(6H,m), 2.0–2.1(2H,m).

By using N-[2-(3,4-dimethoxyphenyl)ethyl]-3-hydroxy-2-(4-nitrophenyl) acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(4-nitrophenyl) acrylamide (the present compound 1247) was obtained according to production example 8.

$^1$H-NMR(CDCl$_3$, TMS) δ(ppm): 8.1–8.2(2H,m), 7.4–7.5 (2H,m), 7.03(1H,s), 6.6–6.9(3H,m), 6.37(1H,t,J=70.8 Hz), 6.28(1H,br), 3.8–3.9(6H,m), 3.6–3.7(2H,m), 2.86(2H,t,J= 6.7 Hz).

By using N-[2-(3,4-dimethoxyphenyl)ethyl]-3-hydroxy-2-(4-methylthiophenyl)acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(4-methylthiophenyl) acrylamide (the present compound 1026) was obtained according to production example 8.

$^1$H-NMR(CDCl$_3$, TMS) δ(ppm): 7.20(4H,s), 6.7–6.9(4H, m), 6.36(1H,t, J=71.5 Hz), 6.07(1H,br), 3.86(3H,s), 3.82 (3H,s), 3.6–3.7(2H,m), 2.84(2H,t, J=6.9 Hz), 2.49(3H,s).

By using N-[2-(3,4-dimethoxyphenyl)ethyl]-3-hydroxy-2-(3,4-dichlorophenyl)acrylamide in place of N-[2-(3,4-dimethoxyphenyl)ethyl]-3-hydroxy-2-(5,6,7,8-tetrahydronaphthalen-2-yl)acrylamide, 2-(3,4-dichlorophenyl)-3-difluoromethoxy-N-[2-(3,4-dimethoxyphenyl)ethyl]acrylamide (the present compound 1065) was obtained according to production example 8.

$^1$H-NMR(CDCl$_3$, TMS) δ(ppm): 7.3–7.5(2H,m), 7.14 (1H,dd,J=8.5,2.1 Hz), 6.90(1H,s), 6.7–6.9(3H,m), 6.35(1H, t,J=71.4 Hz), 6.21(1H,br), 3.87(3H,s), 3.86(3H,s), 3.6–3.7 (2H,m), 2.85(2H,t,J=6.8 Hz).

By using N-[2-(3,4-dimethoxyphenyl)ethyl]-3-hydroxy-2-(4-isopropylphenyl)acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[2-(3,4-dimethoxyphenyl)ethyl]-2-(4-isopropylphenyl) acrylamide (the present compound 1251) was obtained according to production example 8.

$^1$H-NMR(CDCl$_3$, TMS) δ(ppm): 7.0–7.2(4H,m), 6.7–6.9 (4H,m), 6.38(1H,t, J=71.7 Hz), 6.05(1H,br), 3.86(3H,s), 3.83(3H,s), 3.5–3.7(2H,m), 2.8–3.0(3H,m), 1.23(6H,d, J=6.8 Hz).

By using N-[3-(3,4-dimethoxyphenyl)propyl]-3-hydroxy-2-(4-methylphenyl)acrylamide in place of N-[2-(3,4-dimethoxyphenyl)ethyl]-3-hydroxy-2-(5,6,7,8-tetrahydronaphthalen-2-yl)acrylamide, 3-difluoromethoxy-N-[3-(3,4-dimethoxyphenyl)propyl]-2-(4-methylphenyl) acrylamide (the present compound 1476) was obtained according to production example 8.

$^1$H-NMR(CDCl$_3$, TMS) δ(ppm): 7.1–7.3(4H,m), 6.87 (1H,s), 6.7–6.8(3H,m), 6.46(1H,t,J=72.1 Hz), 5.98(1H,br), 3.86(3H,s), 3.85(3H,s), 3.4–3.5(2H,m), 2.63(2H,t, J=7.43 Hz), 2.34(3H,s), 1.8–2.0(2H,m).

Production Example 9

Five hundred milligrams (500 mg) of 3-difluoromethoxy-N-[2-(3,4-dimethoxyphenyl)ethyl]-2-(5,6,7,8-tetrahydronaphthalen-2-yl)acrylamide (1.16 mmol) and 5 ml of anhydrous N,N-dimethylformamide were mixed and cooled, and then 49 mg (1.22 mmol) of 60% sodium hydride was added thereto and stirred at 0° C. for 30 minutes. To the mixture, 164 mg (1.16 mmol) of methyl iodide was added and stirred at 0° C. for 30 minutes and then at room temperature for 2 hours. Water was added to the reaction mixture, which which was followed by extracted with ethyl acetate, washed with 5% hydrochrolic acid and saturated brine subsequently, dried over anhydrous magnesium sulfate and concentrated under reduced pressure. The residue was subjected to silica gel preparative thin layer chromatography (eluent, hexane:ethyl acetate=3:1) to give 460 mg of 3-difluoromethoxy-N-[2-(3,4-dimethoxyphenyl)ethyl]-N-methyl-2-(5,6,7,8-tetrahydronaphthalen-2-yl)acrylamide (the present compound 1125).

$^1$H-NMR(CDCl$_3$, TMS) δ(ppm): 6.5–7.1(7H,m), 6.38 (1H,t,J=72.4 Hz), 3.85 (3H,s), 3.82(3H,s), 3.7–3.8(2H,m), 2.8–3.0(5H,m), 2.6–2.8(4H,m), 1.7–1.9(4H,m).

Production Example 10

Six hundred milligrams (600 mg) of N-[2-(3,4-dimethoxyphenyl)ethyl]-3-hydroxy-2-(5,6,7,8-tetrahydronaphthalen-2-yl)acrylamide (1.57 mmol), 0.14 g (1.89 mmol) of 3-chloropropyne, 280 mg (2.05 mmol) of potassium carbonate and 10 ml of anhydrous N,N-dimethylformamide were mixed and stirred at room temperature. Water was added to the reaction mixture, which was followed by extracted with ethyl acetate, washed with 5% hydrochrolic acid and saturated brine subsequently, dried over anhydrous magnesium sulfate and concentrated under reduced pressure. The residue was subjected to silica gel chromatography (eluent, hexane:ethyl acetate=1:1) to give 415 mg of N-[2-(3,4-dimethoxyphenyl)ethyl]-3-(2-propynyloxy)-2-(5,6,7,8-tetrahydronaphthalen-2-yl) acrylamide (the present compound 1196).

$^1$H-NMR(CDCl$_3$, TMS) δ(ppm): 7.00(3H,s), 6.7–6.9(4H, m), 6.69(1H,s), 4.50(2H,d,J=2.4 Hz), 3.86(6H,s), 3.5–3.7 (2H,m), 2.7–2.9(6H,m), 2.61(1H,t, J=2.4 Hz), 1.7–1.9(4H, m).

By using 1,1,3-trichloropropene in place of 3-chloropropyne, 3-(3,3-dichloroallyloxy)-N-[2-(3,4-dimethoxyphenyl)ethyl]-2-(5,6,7,8-tetrahydronaphthalen-2-yl)acrylamide (the present compound 1232) was obtained according to production example 10.

$^1$H-NMR(CDCl$_3$, TMS) δ(ppm): 6.9–7.0(3H,m), 6.7–6.9 (4H,m), 6.53(1H,s), 5.98(1H,d,J=6.4 Hz), 4.51(2H,d,J=6.5 Hz), 3.86(3H,s), 3.85(3H,s), 3.6–3.7(2H,m), 2.7–2.9(6H,m), 1.7–1.9(4H,m).

By using 1-chloro-2-fluoroethane in place of 3-chloropropyne, N-[2-(3,4-dimethoxyphenyl)ethyl]-3-(2- fluoroethoxy)-2-(5,6,7,8-tetrahydronaphthalen-2-yl) acrylamide (the present compound 1241) was obtained according to production example 10.

$^1$H-NMR(CDCl$_3$, TMS) δ(ppm): 6.99(3H,s), 6.93(1H,br), 6.7–6.9(3H,m), 6.60(1H,s), 4.4–4.7(2H,m), 4.0–4.2(2H,m), 3.86(6H,s), 3.6–3.7(2H,m), 2.7–2.9(6H,m), 1.7–1.9(4H,m).

Production Example 11

Three hundred milligrams (300 mg) of N-[2-(3,4-dimethoxyphenyl)ethyl]-3-(2-propynyloxy)-2-(5,6,7,8-tetrahydronaphthalen-2-yl)acrylamide (0.716 mmol), 20 mg (0.0766 mmol) of tetrabutylammonium fluoride, 100 mg (0.716 mmol) of potassium carbonate and 2 ml of carbon tetrachloride were mixed and stirred at room temperature. Water was added to the reaction mixture, which was followed by extracted with ethyl acetate, washed with 5% hydrochrolic acid and saturated brine subsequently, dried over anhydrous magnesium sulfate and concentrated under reduced pressure. The residue was subjected to silica gel chromatography (eluent, hexane:ethyl acetate=1:1) to give 140 mg of 3-(3-chloro-2-propynyloxy)-N-[2-(3,4-dimethoxyphenyl)ethyl]-2-(5,6,7,8-tetrahydronaphthalen-2-yl)acrylamide (the present compound 1223).

$^1$H-NMR(CDCl$_3$, TMS) δ(ppm): 7.00(3H,s), 6.7–6.9(4H, m), 6.65(1H,s), 4.50(2H,d,J=2.6 Hz), 3.86(6H,s), 3.5–3.7 (2H,m), 2.7–2.9(6H,m), 1.7–1.9(4H,m).

Production Example 12

239 mg of 3-difluoromethoxy-N-[2-(4-hydroxy-3-methoxyphenyl)ethyl]-2-(5,6,7,8-tetrahydronaphthalen-2-yl)acrylamide (0.572 mmol), 128 mg (1.72 mmol) of 3-chloropropyne, 3 ml of anhydrous N,N-dimethylformamide and 20 mg (0.50 mmol) of 60% sodium hydride were mixed and stirred at room temperature for 4 hours. Water was added to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was subjected to silica gel column chromatography to give 225 mg of 3-difluoromethoxy-N-[2-{3-methoxy-4-(2-propynyloxy)phenyl}ethyl]-2-(5,6,7,8-tetrahydronaphthalen-2-yl)acrylamide (the present compound 1268).

$^1$H-NMR(CDCl$_3$, TMS) δ(ppm): 7.00(3H,s), 6.7–6.9(4H, m), 6.69(1H,s), 4.50(2H,d, J=2.4 Hz), 3.86(6H,s), 3.5–3.7 (2H,m), 2.7–2.9(6H,m), 2.61(1H,t, J=2.4 Hz), 1.7–1.9(4H, m).

By using bromoethane in place of 3-chloropropyne, 3-difluoromethoxy-N-[2-(4-ethoxy-3-methoxyphenyl) ethyl]-2-(5,6,7,8-tetrahydronaphthalen-2-yl) acrylamide (the present compound 1143) was obtained according to production example 12.

$^1$H-NMR(CDCl$_3$, TMS) δ(ppm): 6.99(3H,s), 6.7–6.9(4H, m), 6.37(1H,t,J=71.8 Hz), 6.12(1H,br), 4.06(2H,q,J=8.1 Hz), 3.80(3H,s), 3.5–3.7(2H,m), 2.6–2.9(6H,m), 1.7–1.9 (4H,m), 1.44(3H,t,J=7.0 Hz).

By using chloropropane in place of 3-chloropropyne, 3-difluoromethoxy-N-[2-(3-methoxy-4-propoxyphenyl) ethyl]-2-(5,6,7,8-tetrahydronaphthalen-2-yl) acrylamide (the present compound 1258) was obtained according to production example 12.

$^1$H-NMR(CDCl$_3$, TMS) δ(ppm): 6.9–7.1(3H,m), 6.4–6.9 (4H,m), 6.36(1H,t, J=71.9 Hz), 6.05(1H,br), 3.97(2H,t,J=6.8 Hz), 3.82(3H,s), 3.5–3.7(2H,m), 2.6–2.9(6H,m), 1.7–1.9 (6H,m), 1.03(3H,t,J=7.4 Hz).

By using chloroacetonitrile in place of 3-chloropropyne, N-[2-(4-cyanomethoxy-3-methoxyphenyl)ethyl]-3-difluoromethoxy-2-(5,6,7,8-tetrahydronaphthalen-2-yl) acrylamide (the present compound 1274) was obtained according to production example 12.

$^1$H-NMR(CDCl$_3$, TMS) δ(ppm): 6.9–7.1(4H,m), 6.7–6.9 (3H,m), 6.39(1H,t, J=71.8 Hz), 6.10(1H,br), 4.79(2H,s), 3.83(3H,s), 3.6–3.7(2H,m), 2.6–2.9(6H,m), 1.7–1.9(4H,m).

By using allyl chloride in place of 3-chloropropyne, N-[2-(4-allyloxy-3-methoxyphenyl)ethyl]-3-difluoromethoxy-2-(5,6,7,8-tetrahydronaphthalen-2-yl) acrylamide (the present compound 1266) was obtained according to production example 12.

$^1$H-NMR(CDCl$_3$, TMS) δ(ppm): 7.00(3H,s), 6.6–6.9(4H, m), 6.35(1H,t, J=71.9 Hz), 5.9–6.2(2H,m), 5.2–5.5(2H,m), 4.58(2H,dd,J=3.9,1.3 Hz), 3.83(3H,s), 3.5–3.7(2H,m), 2.6–2.9(6H,m), 1.7–1.9(4H,m).

By using 1-chloro-2-butyne in place of 3-chloropropyne, N-[2-{4-(2-butynyloxy)-3-methoxyphenyl}ethyl]-3-difluoromethoxy-2-(5,6,7,8-tetrahydronaphthalen-2-yl) acrylamide (the present compound 1269) was obtained according to production example 12.

$^1$H-NMR(CDCl$_3$, TMS) δ(ppm): 7.00(3H,s), 6.9–7.0(1H, m), 6.84(1H,s), 6.7–6.8(2H,m), 6.34(1H,t,J=71.7 Hz), 6.03 (1H,br), 4.69(2H,q,J=2.3 Hz), 3.82(3H,s), 3.6–3.7(2H,m), 2.83(2H,t,J=6.9 Hz), 2.7–2.8(4H,m), 1.83(3H,t,J=2.2 Hz), 1.7–1.8(4H,m).

By using methoxymethyl chloride in place of 3-chloropropyne, 3-difluoromethoxy-N-[2-(3-methoxy-4-methoxymethoxyphenyl)ethyl]-2-(5,6,7,8-tetrahydronaphthalen-2-yl)acrylamide (the present compound 1284) was obtained according to production example 12.

$^1$H-NMR(CDCl$_3$, TMS) δ(ppm): 7.0–7.1(4H,m), 6.85 (1H,s), 6.7–6.8(2H,m), 6.34(1H,t,J=71.6 Hz), 6.02(1H,br), 5.20(2H,s), 3.83(3H,s), 3.6–3.7(2H,m), 3.51(3H,s), 2.7–2.9 (6H,m), 1.7–1.9(4H,m)

By using isopropyl chloride in place of 3-chloropropyne, 3-difluoromethoxy-N-[2-(4-isopropoxy-3-methoxyphenyl) ethyl]-2-(5,6,7,8-tetrahydronaphthalen-2-yl) acrylamide (the present compound 1259) was obtained according to production example 12.

$^1$H-NMR(CDCl$_3$, TMS) δ(ppm): 7.00(3H,s), 6.6–6.9(4H, m), 6.35(1H,t, J=71.7 Hz), 6.02(1H,br), 4.4–4.6(1H,m), 3.80(3H,s), 3.6–3.7(2H,m), 2.7–2.9(6H,m), 1.7–1.9(4H,m), 1.35(6H,d,J=6.1 Hz).

Production Example 13

Eighty milligrams (80 mg) of acetyl chloride (1.00 mmol) were added to a mixture of 420 mg (1.00 mmol), of 3-difluoromethoxy-N-[2-(4-hydroxy-3-methoxyphenyl) ethyl]-2-(5,6,7,8-tetrahydronaphthalen-2-yl) acrylamide, 120 mg (1.20 mmol) of triethylamine and 5 ml of tetrahydrofuran at 0° C. and stirred at 0° C. for 30 minutes and then at room temperature for 2 hours. Water and ethyl acetate were added to the reaction mixture. The organic layer was washed with 5% hydrochrolic acid and saturated brine subsequently, dried over anhydrous magnesium sulfate and concentrated under reduced pressure. The residue was subjected to silica gel chromatography (eluent, hexane:ethyl acetate=3:1) to give 260 mg of 3-difluoromethoxy-N-[2-(3-methoxy-4-acetyloxyphenyl)ethyl]-2-(5,6,7,8-tetrahydronaphthalen-2-yl)acrylamide (the present compound 1282).

$^1$H-NMR(CDCl$_3$, TMS) δ(ppm): 7.01(3H,s), 6.7–7.0(4H, m), 6.34(1H,t, J=71.2 Hz), 6.18(1H,br), 3.77(3H,s), 3.6–3.7

(2H,m), 2.83(2H,t,J=6.7 Hz), 2.7–2.8 (4H,m), 2.30(3H,s), 1.7–1.8(4H,m).

Production Example 14

One and a half grams (1.5 g) of N-[2-(3,4-dimethoxyphenyl)ethyl]-3-hydroxy-2-(4-methylphenyl)acrylamide (4.39 mmol), 193 mg (4.83 mmol) of 60% sodium hydride, 10 ml of anhydrous dimethoxyethane and 10 ml of anhydrous diethyl ether were mixed, 0.8 ml of dibromodifluoromethane was added thereto at 0° C. and stirred at 0° C. for 3 hours. Water was added to the reaction mixture, which was followed by extracted with ethyl acetate, washed with water, dried over anhydrous magnesium sulfate and concentrated under reduced pressure. The residue was subjected to silica gel column chromatography (eluent, hexane:ethyl acetate=2:1) to give 1.0 g of N-[2-(3,4-dimethoxyphenyl)ethyl]-3-bromodifluoromethoxy-2-(4-methylphenyl)acrylamide (the present compound 1197).

$^1$H-NMR(CDCl$_3$, TMS) δ(ppm): 7.1–7.2(4H,m), 6.7–6.8 (4H,m), 6.4(1H,s), 3.86(3H,s), 3.83(3H,s), 3.66(2H,m), 2.84 (2H,t), 2.35(3H,s).

Production Example 15

Five hundred hundred milligrams (500 mg) of N-[2-(3,4-dimethoxyphenyl) ethyl]-3-bromodifluoromethoxy-2-(4-methylphenyl)acrylamide (1.06 mmol), 0.5 ml of hydrogen fluoride-pyridine complex, 340 mg (1.57 mmol) of mercury oxide and 1 ml of isopropyl ether were mixed and stirred at room temperature for 2 hours. Aqueous sodium bicarbonate solution and celite were added to the reaction mixture and filtered. Water was added to the filtrate, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was recrystallized from t-butyl methyl ether and hexane to give 0.35 g of N-[2-(3,4-dimethoxyphenyl)ethyl]-3-trifluoromethoxy-2-(4-methylphenyl) acrylamide (the present compound 1006).

$^1$H-NMR(CDCl$_3$, TMS) δ(ppm): 7.1–7.2(4H,m), 6.7–6.8 (3H,m), 6.71(1H,s), 6.1(1H,s), 3.84(3H,s), 3.82(3H,s), 3.62 (2H,m), 2.89(2H,t), 2.32(3H,s).

Production Example 16

4.20 g (9.19 mmol) of N-[2-(4-benzyloxy-3-methoxyphenyl)ethyl]-3-hydroxy-2-(5,6,7,8-tetrahydronaphthalen-2-yl)acrylamide, 14.3 g (23.0 mmol) of 10% aqueous potassium hydroxide solution, 0.60 g (1.84 mmol) of tetrabutylammonium bromide and 40 ml of ethylene glycol dimethyl ether were mixed and chlorodifluoromethane gas was blown thereto at room temperature. After a sample was taken out from the reaction mixture and the disappearance of the starting material was confirmed by thin layer chromatography, 5% hydrochloric acid was added to the reaction mixture. The reaction mixture was extracted with ethyl acetate, washed with 5% hydrochloric acid, saturated aqueous sodium bicarbonate solution and saturated brine subsequently, dried over anhydrous magnesium sulfate and concentrated under reduced pressure. The residue was subjected to silica gel chromatography (eluent, hexane:ethyl acetate=2:1) and the obtained product was washed with hexane to give 2.4 g of N-[2-(4-benzyloxy-3-methoxyphenyl)ethyl]-3-difluoromethoxy-2-(5,6,7,8-tetrahydronaphthalen-2-yl)acrylamide (the present compound 1281).

$^1$H-NMR(CDCl$_3$, TMS) δ(ppm): 7.2–7.5(5H,m), 6.9–7.1 (3H,m), 6.6–6.9(4H,m), 6.26(1H,t,J=71.6 Hz), 6.02(1H,br), 5.13(2H,s), 3.84(3H,s), 3.5–3.7(2H,m), 2.7–2.9(6H,m), 1.7–1.9(4H,m).

By using N-[2-(2,3-dihydrobenzo[1,4]dioxin-6-yl)ethyl]-3-hydroxy-2-(5,6,7,8-tetrahydronaphthalen-2-yl)acrylamide in place of N-[2-(4-benzyloxy-3-methoxyphenyl)ethyl]-3-hydroxy-2-(5,6,7,8-tetrahydronaphthalen-2-yl) acrylamide, 3-difluoromethoxy-N-[2-(2,3-dihydrobenzo[1,4]dioxin-6-yl)ethyl]-2-(5,6,7,8-tetrahydronaphthalen-2-yl)acrylamide (the present compound 1450) was obtained according to production example 16.

$^1$H-NMR(CDCl$_3$, TMS) δ(ppm): 7.01(3H,s), 6.85(1H,s), 6.6–6.8(3H,m), 6.41(1t,J=71.6 Hz), 6.02(1H,br), 4.24(4H, s), 3.5–3.7(2H,m), 2.7–2.8(6H,m), 1.7–1.9(4H,m).

By using N-[2-(3-chloro-4-methoxyphenyl)ethyl]-3-hydroxy-2-(5,6,7,8-tetrahydronaphthalen-2-yl)acrylamide in place of N-[2-(4-benzyloxy-3-methoxyphenyl)ethyl]-3-hydroxy-2-(5,6,7,8-tetrahydronaphthalen-2-yl) acrylamide, N-[2-(3-chloro-4-methoxyphenyl)ethyl]-3-difluoromethoxy-2-(5,6,7,8-tetrahydronaphthalen-2-yl) acrylamide (the present compound 1447) was obtained according to production example 16.

$^1$H-NMR(CDCl$_3$, TMS) δ(ppm): 6.9–7.2(4H,m), 6.8–6.9 (3H,m), 6.40(1H,t, J=71.6 Hz), 6.00(1H,br), 3.88(3H,s), 3.5–3.6(2H,m), 2.7–2.9(6H,m), 1.7–1.9(4H,m).

By using N-[2-(4-methoxy-3-methylphenyl)ethyl]-3-hydroxy-2-(5,6,7,8-tetrahydronaphthalen-2-yl)acrylamide in place of N-[2-(4-benzyloxy-3-methoxyphenyl)ethyl]-3-hydroxy-2-(5,6,7,8-tetrahydronaphthalen-2-yl) acrylamide, 3-difluoromethoxy-N-[2-(4-methoxy-3-methylphenyl) ethyl]-2-(5,6,7,8-tetrahydronaphthalen-2-yl)acrylamide (the present compound 1448) was obtained according to production example 16.

$^1$H-NMR(CDCl$_3$, TMS) δ(ppm): 6.9–7.0(4H,m), 6.7–6.9 (3H,m), 6.34(1H,t, J=71.7 Hz), 6.00(1H,br), 3.81(3H,s), 3.5–3.7(2H,m), 2.7–2.8(6H,m), 2.17(3H,s), 1.7–1.9(4H,m).

Production Example 17

2.40 g (4.73 mmol) of N-[2-(4-benzyloxy-3-methoxyphenyl)ethyl]-3-difluoromethoxy-2-(5,6,7,8-tetrahydronaphthalen-2-yl)acrylamide, 1.20 g (7.09 mmol) of 48% hydrobromic acid and 30 ml of acetic acid were mixed and stirred at 80° C. for 2 hours. Water was added to to the reaction mixture, which was followed by extracted with ethyl acetate, washed with 5% hydrochrolic acid and saturated brine subsequently, dried over anhydrous magnesium sulfate and concentrated under reduced pressure. The residue was subjected to silica gel column chromatography (eluent, hexane:ethyl acetate=1:1) to give 1.81 g of 3-difluoromethoxy-N-[2-(4-hydroxy-3-methoxyphenyl) ethyl]-2-(5,6,7,8-tetrahydronaphthalen-2-yl)acrylamide (the present compound 1371).

$^1$H-NMR(CDCl$_3$, TMS) δ(ppm): 7.0–7.1(3H,m), 6.84 (1H,d,J=3.3 Hz), 6.80(1H,s), 6.6–6.7(2H,m), 6.36(1H,t,J= 71.8 Hz), 6.12(1H,br), 5.78(1H,s), 3.82(3H,s), 3.5–3.7(2H, m), 2.4–2.8(6H,m), 1.7–1.9(4H,m).

Production Example 18

417 mg (1.00 mmol) of 3-difluoromethoxy-N-[2-(3-hydroxy-4-methoxyphenyl)ethyl]-2-(5,6,7,8-tetrahydronaphthalen-2-yl)acrylamide, 5 ml of anhydrous N,N-dimethylformamide, 74 mg (1.00 mmol) of 3-chloropropyne and 50 mg (1.25 mmol) of 60% sodium hydride were mixed and stirred at room temperature for 3 hours. Water was added to to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was subjected to silica gel column chromatography to give 162 mg of 3-difluoromethoxy-N-[2-{4-methoxy-3-(2-propynyloxy)phenyl}ethyl]-2-(5,6,7,8-tetrahydronaphthalen-2-yl)acrylamide (the present compound 1299).

$^1$H-NMR(CDCl$_3$, TMS) δ(ppm): 7.00(3H,s), 6.8–6.9(4H,m), 6.37(1H,t, J=71.7 Hz), 6.03(1H,br), 4.71(2H,d,J=2.4 Hz), 3.85(3H,s), 3.6–3.7(2H,m), 2.83(2H, t,J=6.8 Hz), 2.7–2.8(4H,m), 2.47(1H,t,J=2.4 Hz), 1.7–1.9(4H,m).

By using bromoethane in place of 3-chloropropyne, 3-difluoromethoxy-N-[2-(3-ethoxy-4-methoxyphenyl)ethyl]-2-(5,6,7,8-tetrahydronaphthalen-2-yl)acrylamide (the present compound 1320) was obtained according to production example 18.

$^1$H-NMR(CDCl$_3$, TMS) δ(ppm): 7.00(3H,s), 6.7–6.9(4H,m), 6.36(1H,t, J=71.7 Hz), 6.02(1H,br), 4.04(2H,q,J=7.0 Hz), 3.84(3H,s), 3.5–3.7(2H,m), 2.7–2.9 (6H,m), 1.7–1.9 (4H,m), 1.44(3H,t,J=7.0 Hz).

By using chloroacetonitrile in place of 3-chloropropyne, N-[2-(3-cyanomethoxy-4-methoxyphenyl)ethyl]-3-difluoromethoxy-2-(5,6,7,8-tetrahydronaphthalen-2-yl)acrylamide (the present compound 1305) was obtained according to production example 18.

$^1$H-NMR(CDCl$_3$, TMS) δ(ppm): 6.8–7.1(7H,m), 6.40 (1H,t,J=72.1 Hz), 6.05(1H,br), 4.77(2H,s), 3.86(3H,s), 3.5–3.7(2H,m), 2.84(2H,t,J=6.9 Hz), 2.7–2.8(4H,m), 1.7–1.9(4H,m).

Production Example 19

Five hundred milligrams (500 mg) of 3-difluoromethoxy-N-[2-(4-hydroxy-3-methoxyphenyl)ethyl]-2-(4-methylphenyl)acrylamide (1.33 mmol), 5 ml of anhydrous N,N-dimethylformamide, 196 mg (2.65 mmol) of 3-chloropropyne and 60 mg (1.46 mmol) of 60% sodium hydride were stirred at room temperature for 2 hours. Water was added to to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was subjected to silica gel column chromatography (eluent, hexane:ethyl acetate=2:1) to give 242 mg of 3-difluoromethoxy-N-[2-{3-methoxy-4-(2-propynyloxy)phenyl}ethyl]-2-(4-methylphenyl)acrylamide (the present compound 1353).

$^1$H-NMR(CDCl$_3$, TMS) δ(ppm): 7.1–7.2(4H,m), 6.95 (1H,d,J=8.25 Hz), 6.85(1H,s), 6.7–6.8(2H,m), 6.35(1H,t,J=71.7 Hz), 6.11(1H,br), 4.73(2H,d,J=2.3 Hz), 3.81(3H,s), 3.6–3.7(2H,m), 2.83(2H,t,J=6.9 Hz), 2.49(1H,d,J=2.4 Hz), 2.32(3H,s).

By using 3-difluoromethoxy-N-[2-(4-hydroxy-3-methoxyphenyl)ethyl]-2-(indan-5-yl)acrylamide in place of 3-difluoromethoxy-N-[2-(4-hydroxy-3-methoxyphenyl)ethyl]-2-(4-methylphenyl)acrylamide, 3-difluoromethoxy-2-(indan-5-yl)-N-[2-{3-methoxy-4-(2-propynyloxy)phenyl}ethyl]acrylamide (the present compound 1360) was obtained according to production example 19.

$^1$H-NMR(CDCl$_3$, TMS) δ(ppm): 7.1–7.0(2H,m), 6.9–7.1 (2H,m), 6.85(1H,s), 6.7–6.8(2H,m), 6.35(1H,t,J=71.6 Hz), 6.06(1H,br), 4.74(2H,d,J=2.4 Hz), 3.83(3H,s), 3.6–3.7(2H,m), 2.8–2.9(6H,m), 2.49(1H,t,J=2.4 Hz), 2.0–2.2(2H,m).

By using 3-difluoromethoxy-N-[2-(4-hydroxy-3-methoxyphenyl)ethyl]-2-(4-methoxyphenyl)acrylamide in place of 3-difluoromethoxy-N-[2-(4-hydroxy-3-methoxyphenyl)ethyl]-2-(4-methylphenyl)acrylamide, 3-difluoromethoxy-2-(4-methoxyphenyl)-N-[2-{3-methoxy-4-(2-propynyloxy)phenyl}ethyl]acrylamide (the present compound 1358) was obtained according to production example 19.

$^1$H-NMR(CDCl$_3$, TMS) δ(ppm): 7.2–7.3(2H,m), 6.7–7.0 (6H,m), 6.34(1H,t,J=71.6 Hz), 6.05(1H,br), 4.74(2H,d,J=2.5 Hz), 3.83(3H,s), 3.81(3H,s), 3.6–3.7(2H,m), 2.84(2H,t,J=6.8 Hz), 2.49(1H,t,J=2.5 Hz).

By using 3-difluoromethoxy-N-[2-(4-hydroxy-3-methoxyphenyl)ethyl]-2-phenylacrylamide in place of 3-difluoromethoxy-N-[2-(4-hydroxy-3-methoxyphenyl)ethyl]-2-(4-methylphenyl)acrylamide, 3-difluoromethoxy-N-[2-{3-methoxy-4-(2-propynyloxy)phenyl}ethyl]-2-phenylacrylamide (the present compound 1388) was obtained according to production example 19.

$^1$H-NMR(CDCl$_3$, TMS) δ(ppm): 7.3–7.4(5H,m), 6.96 (1H,d,J=8.7 Hz), 6.90(1H,s), 6.7–6.8(2H,m), 6.36(1H,t,J=71.5 Hz), 6.07(1H,br), 4.75(2H,d,J=2.4 Hz), 3.83(3H,s), 3.6–3.7(2H,m), 2.85(2H,t,J=6.8 Hz), 2.50(1H,t,J=2.4 Hz).

By using 3-difluoromethoxy-N-[2-(4-hydroxy-3-methoxyphenyl)ethyl]-2-(4-trifluoromethylphenyl)acrylamide in place of 3-difluoromethoxy-N-[2-(4-hydroxy-3-methoxyphenyl)ethyl]-2-(4-methylphenyl)acrylamide, 3-difluoromethoxy-N-[2-{3-methoxy-4-(2-propynyloxy)phenyl}ethyl]-2-(4-trifluoromethylphenyl)acrylamide (the present compound 1357) was obtained according to production example 19.

$^1$H-NMR(CDCl$_3$, TMS) δ(ppm): 7.59(2H,d,J=8.2 Hz), 7.43(2H,d,J=8.0 Hz), 6.9–7.0(2H,m), 6.7–6.8(2H,m), 6.35 (1H,t,J=71.0 Hz), 6.21(1H,br), 4.75(2H,d, J=2.2 Hz), 3.84 (3H,s), 3.6–3.7(2H,m), 2.87(2H,t,J=6.8 Hz), 2.49(1H,t,J=2.2 Hz).

By using 3-difluoromethoxy-N-[2-(4-hydroxy-3-methoxyphenyl)ethyl]-2-(4-ethylphenyl)acrylamide in place of 3-difluoromethoxy-N-[2-(4-hydroxy-3-methoxyphenyl)ethyl]-2-(4-methylphenyl)acrylamide, 3-difluoromethoxy-2-(4-ethylphenyl)-N-[2-{3-methoxy-4-(2-propynyloxy)phenyl}ethyl]acrylamide (the present compound 1354) was obtained according to production example 19.

$^1$H-NMR(CDCl$_3$, TMS) δ(ppm): 7.1–7.3(4H,m), 6.96 (1H,d,J=8.7 Hz), 6.87 (1H,s), 6.7–6.8(2H,m), 6.35(1H,t,J=71.6 Hz), 6.06(1H,br), 4.75(2H,d,J=2.4 Hz), 3.83(3H,s), 3.6–3.7(2H,m), 2.85(2H,t,J=6.8 Hz), 2.64(2H,q,J=6.8 Hz), 2.50(1H,t, J=2.4 Hz).

By using 3-difluoromethoxy-N-[2-(4-hydroxy-3-methoxyphenyl)ethyl]-2-(4-fluorophenyl)acrylamide in place of 3-difluoromethoxy-N-[2-(4-hydroxy-3-methoxyphenyl)ethyl]-2-(4-methylphenyl)acrylamide, 3-difluoromethoxy-2-(4-fluorophenyl)-N-[2-{3-methoxy-4-(2-propynyloxy)phenyl}ethyl]acrylamide (the present compound 1392) was obtained according to production example 19.

$^1$H-NMR(CDCl$_3$, TMS) δ(ppm): 7.2–7.3(2H,m), 6.9–7.1 (3H,m), 6.87(1H,s), 6.7–6.8(2H,m), 6.34(1H,t,J=71.3 Hz), 6.17(1H,br), 4.76(2H,d,J=2.4 Hz), 3.85(3H,s), 3.6–3.7(2H,m), 2.85(2H,t,J=6.8 Hz), 2.64(2H,q,J=6.8 Hz), 2.50(1H,t,J=2.4 Hz).

By using 3-difluoromethoxy-N-[2-(4-hydroxy-3-methoxyphenyl)ethyl]-2-(naphthalen-2-yl)acrylamide in place of 3-difluoromethoxy-N-[2-(4-hydroxy-3-methoxyphenyl)ethyl]-2-(4-methylphenyl)acrylamide, 3-difluoromethoxy-N-[2-{3-methoxy-4-(2-propynyloxy)phenyl}ethyl]-2-(naphthalen-2-yl)acrylamide (the present compound 2202) was obtained according to production example 19.

¹H-NMR(CDCl₃, TMS) δ(ppm): 7.7–7.9(4H,m), 7.4–7.5 (3H,m), 7.02(1H,s), 6.93(1H,d,J=8.6 Hz), 6.7–6.8(2H,m), 6.39(1H,t,J=71.5 Hz), 6.11(1H,br), 4.72(2H,d, J=2.2 Hz), 3.78(3H,s), 3.6–3.7(2H,m), 2.87(2H,t,J=6.8 Hz), 2.48(1H,t, J=2.5 Hz).

By using 3-difluoromethoxy-N-[2-(4-hydroxy-3-methoxyphenyl)ethyl]-2-(5-methylthiophen-2-yl) acrylamide in place of 3-difluoromethoxy-N-[2-(4-hydroxy-3-methoxyphenyl)ethyl]-2-(4-methylphenyl)acrylamide, 3-difluoromethoxy-2-(5-methylthiophen-2-yl)-N-[2-{3-methoxy-4-(2-propynyloxy) phenyl}ethyl]acrylamide (the present compound 2133) was obtained according to production example 19.

¹H-NMR(CDCl₃, TMS) δppm): 7.62(1H,s), 6.95(1H,d,J= 8.6 Hz), 6.15–6.72 (3H,m), 6.4(1H,br), 4.74(2H,d,J=2.4 Hz), 3.83(3H,s), 3.6(2H,m), 2.79(2H,t, J=6.9 Hz), 2.50(1H, t,J=2.4 Hz), 2.47(3H,s).

By using 3-difluoromethoxy-N-[2-(4-hydroxy-3-methoxyphenyl)ethyl]-2-(3,4-dichlorophenyl)acrylamide in place of 3-difluoromethoxy-N-[2-(4-hydroxy-3-methoxyphenyl)ethyl]-2-(4-methylphenyl)acrylamide, 3-difluoromethoxy-2-(3,4-dichlorophenyl)-N-[2-{3-methoxy-4-(2-propynyloxy)phenyl}ethyl]acrylamide (the present compound 1429) was obtained according to production example 19.

¹H-NMR(CDCl₃, TMS) δppm): 7.4–7.5(2H,m), 7.13(1H, dd,J=2.14, 8.2 Hz), 6.97(1H,d,J=7.1 Hz), 6.92(1H,s), 6.7–6.8 (2H,m), 6.0–6.7(2H,m), 4.75(2H,d,J=2.4 Hz), 3.84 (3H,s), 3.6(2H,m), 2.85(2H,t, J=6.5 Hz), 2.51(1H,t,J=2.4 Hz).

By using 3-difluoromethoxy-N-[2-(4-hydroxy-3-methoxyphenyl)-1-methylethyl]-2-(4-methylphenyl) acrylamide in place of 3-difluoromethoxy-N-[2-(4-hydroxy-3-methoxyphenyl)ethyl]-2-(4-methylphenyl)acrylamide, 3-difluoromethoxy-N-[2-(3-methoxy-4-(2-propynyloxy) phenyl)-1-methylethyl]-2-(4-methylphenyl)acrylamide (the present compound 1465) was obtained according to production example 19.

¹H-NMR(CDCl₃, TMS) δppm): 7.1–7.2(4H,m), 6.95(1H, d,J=7.9 Hz), 6.85(1H,s), 6.7–6.8(2H,m), 6.36(1H,t,J=71.7 Hz), 5.78(1H,d,J=7.8 Hz), 4.75(2H,d,J=2.2 Hz), 4.3–4.5 (1H,m), 3.82(3H,s), 2.7–2.9(2H,m), 2.49(1H,t, J=2.1 Hz), 2.34(3H,s), 1.20(3H,d,J=6.7 Hz).

By using bromomethylcyclopropane in place of 3-chloropropyne, N-[2-(4-cyclopropylmethoxy-3-methoxyphenyl)ethyl]-3-difluoromethoxy-2-(4-methylphenyl)acrylamide (the present compound 1271) was obtained according to production example 19.

¹H-NMR(CDCl₃, TMS) δ(ppm): 7.1–7.2(4H,m), 6.7–6.9 (4H,m), 6.35(1H,t, J=71.7 Hz), 6.01(1H,br), 3.8–3.9(5H,m), 3.6–3.7(2H,m), 2.82(2H,t, J=6.8 Hz), 2.33(3H,s), 1.2–1.4 (1H,m), 0.6–0.7(2H,m), 0.3–0.4(2H,m).

Production Example 20

477 mg (1.20 mmol) of 3-difluoromethoxy-N-[2-(4-hydroxy-3-methoxyphenyl)ethyl]-2-(4-chlorophenyl) acrylamide, 5 ml of anhydrous N,N-dimethylformamide, 180 mg (2.40 mmol) of 3-chloropropyne and 72 mg (1.80 mmol) of 60% sodium hydride were stirred at room temperature for 2 hours. Water was added to to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was subjected to silica gel column chromatography (eluent, hexane-:ethyl acetate=2:1) to give 70 mg of 3-difluoromethoxy-N-[2-{3-methoxy-4-(2-propynyloxy)phenyl}ethyl]-2-(4-chlorophenyl)acrylamide (the present compound 1355).

¹H-NMR(CDCl₃, TMS) δ(ppm): 7.1–7.4(4H,m), 6.97 (1H,d,J=8.7 Hz), 6.89 (1H,s), 6.7–6.8(2H,m), 6.34(1H,t,J= 71.3 Hz), 6.17(1H,br), 4.75(2H,d,J=2.4 Hz), 3.84(3H,s), 3.6–3.7(2H,m), 2.85(2H,t,J=7.0 Hz), 2.50(1H,d,J=2.4 Hz).

Production Example 21

Two hundred milligrams (200 mg) of 3-hydroxy-N-[2-(4-hydroxy-3-methoxyphenyl)ethyl]-2-(4-methylphenyl) acrylamide (0.611 mmol), 2 ml of anhydrous N,N-dimethylformamide, 144 mg (1.22 mmol) of 3-bromopropyne and 173 mg (1.25 mmol) of potassium carbonate were stirred at room temperature for 2 hours and then at 50° C. for 4 hours. Water was added to to the reaction mixture, which was followed by extracted with ethyl acetate, washed with 5% hydrochrolic acid, saturated aqueous sodium bicarbonate and saturated brine subsequently, dried over anhydrous magnesium sulfate and concentrated under reduced pressure. The residue was subjected to silica gel column chromatography (eluent, hexane:ethyl acetate=1:1) to give 100 mg of N-[2-{3-methoxy-4-(2-propynyloxy) phenyl}ethyl]-3-(2-propynyloxy)-2-(4-methylphenyl) acrylamide (the present compound 1364).

¹H-NMR(CDCl₃, TMS) δ(ppm): 7.1–7.2(4H,m), 6.98 (1H,d,J=8.6 Hz), 6.6–6.9(4H,m), 4.74(2H,d,J=2.5 Hz), 4.49 (2H,d,J=2.5 Hz), 3.85(3H,s), 3.6–3.7 (2H,m), 2.83(2H,t,J= 6.9 Hz), 2.59(1H,d,J=2.3 Hz), 2.50(1H,d,J=2.2 Hz), 2.32 (3H,s).

Production Example 22

Three hundred milligrams (300 mg) of 3-hydroxy-N-[2-(4-hydroxy-3-methoxyphenyl)ethyl]-2-(4-chlorophenyl) acrylamide (0.863 mmol) and 3 ml of anhydrous N,N-dimethylformamide were mixed and 320 mg (4.32 mmol) of 3-chloropropyne was added thereto at 0–5° C., and then 100 mg (2.59 mmol) of 60% sodium hydride was added at 0–5° C. The mixture was stirred for 1 hour at 0–5° C. and further at room temperature. Water was added to to the reaction mixture, which was followed by extracted with ethyl acetate, washed with 5% hydrochrolic acid and saturated brine subsequently, dried over anhydrous magnesium sulfate and concentrated under reduced pressure. The residue was subjected to silica gel chromatography (eluent, hexane:ethyl acetate=2:1) to give 160 mg of 2-(4-chlorophenyl)-N-[2-{3-methoxy-4-(2-propynyloxy)phenyl}ethyl]-3-(2-propynyloxy) acrylamide (the present compound 1367).

¹H-NMR(CDCl₃, TMS) δ(ppm): 7.2–7.3(4H,m), 6.9–7.0 (2H,m), 6.7–6.8 (3H,m), 4.75(2H,d,J=2.4 Hz), 4.52(2H,d, J=2.4 Hz), 3.86(3H,s), 3.6–3.7(2H,m), 2.84(2H,t,J=6.9 Hz), 2.63(1H,d,J=2.4 Hz), 2.51(1H,d,J=2.42 Hz).

Production Example 23

4.17 g (10.00 mmol) of N-[2-(4-benzyloxy-3-methoxyphenyl)ethyl]-3-hydroxy-2-(4-methylphenyl) acrylamide, 22.4 g (40.0 mmol) of 10% aqueous potassium hydroxide solution, 1.62 g (5.00 mmol) of tetrabutylammonium bromide and 50 ml of ethylene glycol dimethyl ether were mixed and chlorodifluoromethane gas was blown thereto at room temperature. After a sample was taken out from the reaction mixture and the disappearance of the starting material was confirmed by thin layer chromatography, 5% hydrochloric acid was added to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was washed with diethyl ether to give 3.46 g of N-[2-(4-benzyloxy-3-methoxyphenyl)ethyl]-3-difluoromethoxy-2-(4-methylphenyl)acrylamide (the present compound 1451).

$^1$H-NMR(CDCl$_3$, TMS) δ(ppm): 7.2–7.5(5H,m), 7.1–7.2 (4H,m), 6.84(1H,s), 6.80(1H,d,J=8.2 Hz), 6.74(1H,d,J=1.6 Hz), 6.65(1H,dd,J=8.0,1.8 Hz), 6.26(1H,t, J=71.6 Hz), 6.02 (1H,br), 5.13(2H,s), 3.84(3H,s), 3.6–3.7(2H,m), 2.81(2H,t, J=6.8 Hz), 2.33(3H,s).

Production Example 24

9.40 g of N-[2-(4-benzyloxy-3-methoxyphenyl)ethyl]-3-difluoromethoxy-2-(4-methylphenyl)acrylamide (20.1 mmol), 3.72 g (22.1 mmol) of 48% hydrobromic acid and 95 ml of acetic acid were mixed and stirred at 80° C. for 1.5 hours. The solvent was distilled off from the reaction mixture under reduced pressure and the residue was subjected to silica gel column chromatography (eluent, hexane:ethyl acetate=2:1) to give 4.55 g of 3-difluoromethoxy-N-[2-(4-hydroxy-3-methoxyphenyl)ethyl]-2-(4-methylphenyl) acrylamide (the present compound 1452).

$^1$H-NMR(CDCl$_3$, TMS) δ(ppm): 7.1–7.2(4H,m), 6.8–6.9 (2H,m), 6.6–6.7(2H,m,), 6.35(1H,t,J=71.7 Hz), 6.02(1H,br), 5.51(1H,s), 3.84(3H,s), 3.6–3.7(2H,m), 2.81(2H,t, J=6.9 Hz), 2.34(3H,s).

Production Example 25

1.48 g (3.38 mmol) of N-[2-(4-benzyloxy-3-methoxyphenyl)ethyl]-3-hydroxy-2-(4-chlorophenyl) acrylamide, 4.3 g (8.46 mmol) of 10% aqueous potassium hydroxide solution, 220 mg (0.677 mmol) of tetrabutylammonium bromide and 15 ml of ethylene glycol dimethyl ether were mixed and chlorodifluoromethane gas was blown thereto at room temperature. After a sample was taken out from the reaction mixture and the disappearance of the starting material was confirmed by thin layer chromatography, 5% hydrochloric acid was added to the reaction mixture, which was followed by extracted with ethyl acetate, washed with 5% hydrochrolic acid, saturated aqueous sodium bicarbonate solution and saturated brine subsequently, dried over anhydrous magnesium sulfate and concentrated under reduced pressure. The residue was washed with hexane to give 1.45 g of N-[2-(4-benzyloxy-3-methoxyphenyl)ethyl]-2-(4-chlorophenyl)-3-difluoromethoxyacrylamide (the present compound 1453).

$^1$H-NMR(CDCl$_3$, TMS) δ(ppm): 7.2–7.5(9H,m), 6.87 (1H,s), 6.80(1H,d, J=8.3 Hz), 6.75(1H,d,J=2.0Hz), 6.66(1H, dd,J=8.0,2.0Hz), 6.23(1H,t,J=71.7 Hz), 6.12(1H,br), 5.14 (2H,s), 3.85(3H,s), 3.6–3.7(2H,m), 2.82(2H,t,J=6.8 Hz)

Production Example 26

1.45 g (2.97 mmol) of N-[2-(4-benzyloxy-3-methoxyphenyl)ethyl]-2-(4-chlorophenyl)-3-difluoromethoxyacrylamide, 751 mg (4.46 mmol) of 48% hydrobromic acid and 15 ml of acetic acid were mixed and stirred at 80° C. for 1.5 hours. Water was added to to the reaction mixture, which was followed by extracted with ethyl acetate twice, washed with saturated brine twice, dried over anhydrous magnesium sulfate and concentrated under reduced pressure. The residue was subjected to silica gel column chromatography (eluent, hexane:ethyl acetate=1:1) to give 880 mg of 2-(4-chlorophenyl)-3-difluoromethoxy-N-[2-(4-hydroxy-3-methoxyphenyl)ethyl]acrylamide (the present compound 1454).

$^1$H-NMR(CDCl$_3$, TMS) δ(ppm): 7.2–7.4(4H,m), 6.88 (1H,s), 6.84(1H,d, J=7.8 Hz), 6.6–6.8(2H,m), 6.34(1H,t,J= 71.4 Hz), 6.14(1H,br), 5.53(1H,s), 3.85 (3H,s), 3.6–3.7(2H, m), 2.82(2H,t,J=6.8 Hz).

Reference Production Example 1

A mixture of 5.00 g (33.3 mmol) of (4-methylphenyl) acetic acid, 5.94 g (49.9 mmol) of thionyl chloride, 0.12 g (1.6 mmol) of N,N-dimethylformamide and 20 ml of toluene was stirred at 100° C. for 1 hour, cooled and concentrated under reduced pressure. The residue was added to a mixture of 6.34 g (35.0 mmol) 2-(3,4-dimethoxyphenyl)ethylamine, 8.6 g (67 mmol) of diisopropylethylamine and 25 ml of toluene at 0° C. and kept at 0° C. for 30 minutes and at room temperature for 6 hours. Water and ethyl acetate were added to the reaction mixture and precipitated solid was collected with filtration. The obtained solid was dried to give 5.76 g of N-[2-(3,4-dimethoxyphenyl)ethyl]-2-(4-methylphenyl) acetamide.

$^1$H-NMR(CDCl$_3$, TMS) δ(ppm): 7.0–7.2(4H,m), 6.72 (1H,d,J=8.2 Hz), 6.57–6.60(2H, m), 5.4(1H,s), 3.86(3H,s), 3.82(3H,s), 3.49(2H,s), 3.43(2H,m), 2.67(2H,t,J=6.9 Hz), 2.34(3H,s).

One gram (1.0 g) of N-[2-(3,4-dimethoxyphenyl)ethyl]-2-(4-methylphenyl) acetamide (3.2 mmol), 1.68 g (9.64 mmol) of t-butoxybis(dimethylamino)methane and 15 ml of N,N-dimethylformamide were mixed and stirred at 90° C. for 3 hours and then at 110° C. for 3 hours. Water was added to the reaction mixture, which was followed by extracted with ethyl acetate, washed with saturated brine twice, dried over anhydrous magnesium sulfate and the solvent was distilled off under reduced pressure to give 1.20 g of crude N-[2-(3,4-dimethoxyphenyl)ethyl]-3-dimethylamino-2-(4-methylphenyl)acrylamide.

One gram (1.0 g) of crude N-[2-(3,4-dimethoxyphenyl) ethyl]-3-dimethylamino-2-(4-methylphenyl)acrylamide (2.7 mmol), 12 ml of 5% hydrochloric acid and 20 ml of tetrahydrofuran were mixed and stirred at room temperature for 2 hours. Water was added to the reaction mixture, which was followed by extracted with ethyl acetate twice, washed with saturated brine twice, dried over anhydrous magnesium sulfate and the solvent was distilled off under reduced pressure. The residue was washed with hexane and dried to give 0.76 g of N-[2-(3,4-dimethoxyphenyl)ethyl]-3-hydroxy-2-(4-methylphenyl)acrylamide.

$^1$H-NMR(CDCl$_3$, TMS) δ(ppm): 7.26(1H,s), 7.0–7.1(4H, m), 6.6–6.7(3H,m), 5.5(1H,s), 3.86(3H,s), 3.82(3H,s), 3.51 (2H,m), 2.75(2H,t,J=6.9 Hz), 2.35(3H,s).

Reference Production Example 2

A mixture of 5.00 g (29.3 mmol) of (4-chlorophenyl) acetic acid, 5.23 g (43.9 mmol) of thionyl chloride and 50 ml of toluene was stirred at 50° C. for 30 minutes and then 80° C. for 2.5 hours, cooled and concentrated under reduced pressure. The residue was added to a mixture of 5.18 g (28.5 mmol) 2-(3,4-dimethoxyphenyl)ethylamine, 3.46 g (34.2 mmol) of triethylamine and 50 ml tetrahydrofuran at 0° C. and kept at 0° C. for 30 minutes and at room temperature for 3 hours. Water and ethyl acetate were added to the reaction mixture and precipitated solid was collected with filtration. The obtained solid was dried to give 5.75 g of N-[2-(3,4-dimethoxyphenyl)ethyl]-2-(4-chlorophenyl) acetamide.

¹H-NMR(CDCl₃, TMS) δ(ppm): 7.2–7.3(2H,m), 7.0–7.1 (2H,m), 6.72(1H,d, J=8.1 Hz), 6.61(1H,d,J=2.0 Hz), 6.51 (1H,dd,J=8.0,1.9 Hz), 5.31(1H,br), 3.87(3H,s), 3.83(3H,s), 3.4–3.5(4H,m), 2.68(2H,t,J=6.8 Hz).

5.75 g (17.2 mmol) of N-[2-(3,4-dimethoxyphenyl)ethyl]-2-(4-chlorophenyl) acetamide, 9.00 g (51.6 mmol) of t-butoxybis(dimethylamino)methane and 90 ml of N,N-dimethylformamide were mixed and stirred at 90° C. for 3 hours and then at 110° C. for 3 hours. Water was added to the reaction mixture, which was followed by extracted with ethyl acetate, washed with saturated brine twice, dried over anhydrous magnesium sulfate and the solvent was distilled off under reduced pressure to give 6.68 g of crude N-[2-(3,4-dimethoxyphenyl)ethyl]-3-dimethylamino-2-(4-chlorophenyl)acrylamide.

6.60 g (17.2 mmol) of crude N-[2-(3,4-dimethoxyphenyl) ethyl]-3-dimethylamino-2-(4-chlorophenyl)acrylamide, 80 ml of 5% hydrochloric acid and 100 ml of tetrahydrofuran were mixed and stirred at room temperature for 2 hours. Water was added to the reaction mixture, which was followed by extracted with ethyl acetate twice, washed with saturated brine twice, dried over anhydrous magnesium sulfate and the solvent was distilled off under reduced pressure. The residue was washed with hexane and dried to give 4.46 g of N-[2-(3,4-dimethoxyphenyl)ethyl]-3-hydroxy-2-(4-chlorophenyl)acrylamide.

¹H-NMR(CDCl₃, TMS) δ(ppm): 13.66(1H,d,J=11.34 Hz), 7.2–7.3(2H,m), 7.0–7.1(3H,m), 6.74(1H,d,J=8.1 Hz), 6.5–6.6(2H,m), 5.32(1H,br), 3.87(3H,s), 3.80(3H,s), 3.5–3.6 (2H,m), 2.75(2H,d,J=6.8 Hz).

Reference Production Example 3

According to the description of JP hei10-87602A, (5,6,7,8-tetrahydronaphthalen-2-yl)acetic acid was obtained.

A mixture of 3.60 g (18.9 mmol) of (5,6,7,8-tetrahydronaphthalen-2-yl)acetic acid, 3.38 g (28.4 mmol) of thionyl chloride and 40 ml of toluene was stirred at 50° C. for 30 minutes and then 80° C. for 2.5 hours, cooled and concentrated under reduced pressure. The residue was added to a mixture of 3.43 g (18.9 mmol) 2-(3,4-dimethoxyphenyl) ethylamine, 2.30 g (22.7 mmol) of triethylamine and 40 ml of tetrahydrofuran at 0° C. and kept at 0° C. for 30 minutes and at room temperature for 3 hours. Water and ethyl acetate were added to the reaction mixture and precipitated solid was collected with filtration. The obtained solid was dried to give 5.78 g of N-[2-(3,4-dimethoxyphenyl)ethyl]-2-(5,6,7,8-tetrahydronaphthalen-2-yl)acetamide.

¹H-NMR(CDCl₃, TMS) δ(ppm): 6.99(1H,d,J=8.1 Hz), 6.8–6.9(2H,m), 6.5–6.8(3H,m), 5.42(1H,br), 3.85(3H,s), 3.82(3H,s), 3.4–3.5(4H,m), 2.6–2.8(6H,m), 1.7–1.9(4H,m).

2.65 g (7.50 mmol) of N-[2-(3,4-dimethoxyphenyl)ethyl]-2-(5,6,7,8-tetrahydronaphthalen-2-yl)acetamide, 3.92 g (22.5 mmol) of t-butoxybis (dimethylamino)methane and 30 ml of N,N-dimethylformamide were mixed and stirred at 90° C. for 3 hours and then at 110° C. for 3 hours. Water was added to the reaction mixture, which was followed by extracted with ethyl acetate twice, washed with saturated brine twice, dried over anhydrous magnesium sulfate and the solvent was distilled off under reduced pressure to give 3.30 g of crude N-[2-(3,4-dimethoxyphenyl)ethyl]-3-dimethylamino-2-(5,6,7,8-tetrahydronaphthalen-2-yl) acrylamide.

Three grams (3.00 g) of crude N-[2-(3,4-dimethoxyphenyl)ethyl]-3-dimethylamino-2-(5,6,7,8-tetrahydronaphthalen-2-yl)acrylamide (7.35 mmol), 30 ml of 5% hydrochloric acid and 30 ml of tetrahydrofuran were mixed and stirred at room temperature for 1.5 hours. Water was added to the reaction mixture, which was followed by extracted with ethyl acetate twice, washed with saturated brine twice, dried over anhydrous magnesium sulfate and the solvent was distilled off under reduced pressure. The residue was washed with hexane and dried to give 2.20 g of N-[2-(3,4-dimethoxyphenyl)ethyl]-3-hydroxy-2-(5,6,7,8-tetrahydronaphthalen-2-yl)acrylamide.

¹H-NMR(CDCl₃, TMS) δ(ppm): 13.61(1H,d,J=11.2 Hz), 6.9–7.1(2H,m), 6.6–6.8(5H, m), 5.56(1H,br), 3.86(3H,s), 3.82(3H,s), 3.4–3.6(2H,m), 2.6–2.9(6H,m), 1.7–1.9(4H,m).

Reference Production Example 4

15.2 g (0.1 mol) of vanilline, 20.5 g (0.12 mol) of benzyl bromide, 17.9 g (0.13 mol) of potassium carbonate and 150 ml of N,N-dimethylformamide were mixed and stirred at 50° C. for 2 hours. Water was added to the reaction mixture, which was followed by extracted with ethyl acetate, washed with 5% hydrochloric acid and then saturated brine, dried over anhydrous magnesium sulfate and the solvent was distilled off under reduced pressure. The residue was washed with hexane and dried to give 23.1 g of 4-benzyloxy-3-methoxybenzaldehyde.

¹H-NMR(CDCl₃, TMS) δ(ppm): 9.83(1H,s), 7.5–7.3(7H, m), 6.98(1H,d, J=8.2 Hz), 5.24(2H,s), 3.95(3H,s).

23.1 g (95.7 mmol) of 4-benzyloxy-3-methoxybenzaldehyde, 8.76 g (143 mmol) of nitromethane and 250 ml of acetic acid were mixed and 7.07 g (96.7 mmol) of butylamine was added dropwise thereto. The mixture was refluxed for 2 hours by heating, and then cooled and poured into ice-water. The precipitated crystals were dissolved with ethyl acetate, washed with saturated brine, dried over anhydrous magnesium sulfate and the solvent was distilled off under reduced pressure. The residue was washed with hexane and dried to give 17.0 g of 1-benzyloxy-2-methoxy-4-(2-nitrovinyl)benzene.

¹H-NMR(CDCl₃, TMS) δ(ppm): 7.95(1H,d,J=13.5 Hz), 7.51(1H,d,J=14.7 Hz), 7.3–7.5(5H,m), 5.24(2H,s), 3.95(3H, s).

6.78 g (178.8 mmol) of lithium aluminum hydride and 200 ml of anhydrous tetrahydrofuran were mixed and an anhydrous tetrahydrofuran solution of 17.0 g (59.6 mmol) of 1-benzyloxy-2-methoxy-4-(2-nitrovinyl)benzene was added dropwise thereto over about 90 minutes under vigorous stirring. The mixture was refluxed for 2 hours by heating, and then cooled and aqueous sodium hydroxide solution was added to the mixture. The precipitates were filtered off with celite-precoated glass filter and the solvent was distilled off from the filtrate under reduced pressure. The residue was extracted with ethyl acetate, washed with saturated brine, dried over potassium carbonate and the solvent was distilled off under reduced pressure to give 13.67 g of crude 2-(3-methoxy-4-benzyloxyphenyl)ethylamine.

¹H-NMR(CDCl₃, TMS) δ(ppm): 7.2–7.5(5H,m), 6.6–6.9 (3H,m), 5.10(2H,s), 3.85(3H,s), 2.90(2H,t,J=6.7 Hz), 2.66 (2H,t,J=6.8 Hz), 2.0–2.4(2H,br).

8.01 g (31.2 mmol) of crude 2-(3-methoxy-4-benzyloxyphenyl)ethylamine, 3.78 g (37.4 mmol) of triethylamine and 80 ml of tetrahydrofuran were mixed and cooled to 0° C. and then (5,6,7,8-tetrahydronaphthalen-2-yl)acetyl chloride was added dropwise thereto. The mixture was stirred at 0° C. for 30 minutes and further at room temperature for 2 hours. Water was added to the reaction mixture, which was followed by extracted with ethyl acetate, washed with 5% hydrochloric acid and then saturated brine, dried over anhydrous magnesium sulfate and the solvent was distilled off under reduced pressure. The residue was subjected to silica gel column chromatography (eluent, hexane:ethyl acetate=1:1) to give 8.3 g of N-[2-(4-benzyloxy-3-methoxyphenyl)ethyl]-2-(5,6,7,8-tetrahydronaphthalen-2-yl)acetamide.

$^1$H-NMR(CDCl$_3$, TMS) δ(ppm): 7.1–7.2(4H,m), 6.72 (1H,d,J=8.2 Hz), 6.5–6.6(2H,m), 5.4(1H,s), 3.86(3H,s), 3.82 (3H,s), 3.49(2H,s), 3.3–3.4(2H,m), 2.67(2H,t,J=6.9 Hz), 2.34(3H,s).

8.8 g (13.6 mmol) of N-[2-(4-benzyloxy-3-methoxyphenyl)ethyl]-2-(5,6,7,8-tetrahydronaphthalen-2-yl)acetamide, 8.9 g (51.1 mmol) of t-butoxybis(dimethylamino)methane and 100 ml of N,N-dimethylformamide were mixed and stirred at 100° C. for 6 hours. Water was added to the reaction mixture, which was followed by extracted with ethyl acetate, washed with saturated brine twice, dried over anhydrous magnesium sulfate and the solvent was distilled off under reduced pressure. To the residue, 50 ml of 5% hydrochloric acid and 100 ml of tetrahydrofuran were added and stirred at room temperature for 2 hours. Water was added to the reaction mixture, which was followed by extracted with ethyl acetate twice, washed with saturated brine twice, dried over anhydrous magnesium sulfate and the solvent was distilled off under reduced pressure. The residue was subjected to silica gel chromatography (eluent, hexane:ethyl acetate=2:1) and dried to give 4.20 g of N-[2-(4-benzyloxy-3-methoxyphenyl)ethyl]-3-hydroxy-2-(5,6,7,8-tetrahydronaphthalen-2-yl)acrylamide.

$^1$H-NMR(CDCl$_3$, TMS) δ(ppm): 13.61(1H,d,J=11.3 Hz), 7.2–7.5(5H,m), 7.04(1H,d, J=11.0 Hz), 6.97(1H,d,J=8.2 Hz), 6.7–6.9(3H,m), 6.66(1H,d,J=2.0 Hz), 6.59(1H,dd,J=8.3, 1.9 Hz), 5.55(1H,br), 5.11(2H,s), 3.83(3H,s), 3.4–3.6 (2H,m), 2.6–2.9(6H,m), 1.7–1.9(4H,m).

Reference Production Example 5

15.26 g (59.3 mmol) of crude 2-(3-methoxy-4-benzyloxyphenyl)ethylamine, 9.09 g (89.0 mmol) of triethylamine and 100 ml of tetrahydrofuran were mixed and cooled to about 0° C. and then 5.44 g (32.28 mmol) of (4-methylphenyl)acetyl chloride was added dropwise thereto. The mixture was stirred at 0° C. for 30 minutes and further at room temperature for 3 hours. Water was added to the reaction mixture, which was followed by extracted with ethyl acetate, washed with 5% hydrochloric acid and saturated brine subsequently, dried over anhydrous magnesium sulfate and the solvent was distilled off under reduced pressure. The residue was washed with hexane and dried to give 19.48 g of N-[2-(4-benzyloxy-3-methoxyphenyl)ethyl]-2-(4-methylphenyl)acetamide.

$^1$H-NMR(CDCl$_3$, TMS) δ(ppm): 7.2–7.5(5H,m), 7.0–7.1 (4H,m), 6.73(1H,d, J=8.2 Hz), 6.62(1H,d,J=1.9 Hz), 6.46 (1H,dd,J=8.1,1.9 Hz), 5.34(1H,br), 5.12(2H,s), 3.83(3H,s), 3.4–3.5(4H,m), 2.64(2H,t,J=6.9 Hz), 2.32(3H,s).

11.68 g (30.0 mmol) of N-[2-(4-benzyloxy-3-methoxyphenyl)ethyl]-2-(4-methylphenyl)acetamide and 15.67 g (90.0 mmol) of t-butoxybis(dimethylamino) methane were mixed and stirred at 80° C. for 2 hours. The reaction mixture was cooled and tetrahydrofuran was added thereto. The reaction mixture was acidified with 5% hydrochloric acid and stirred at room temperature for 2 hours. After the solvent was distilled off under reduced pressure, water and 5% hydrochloric acid were added to the residue, which was followed by extracted with chloroform twice, washed with saturated brine twice, dried over anhydrous magnesium sulfate and the solvent was distilled off under reduced pressure. The residue was washed with hexane and dried to give 11.30 g of N-[2-(4-benzyloxy-3-methoxyphenyl)ethyl]-3-hydroxy-2-(4-methylphenyl)acrylamide.

$^1$H-NMR(CDCl$_3$, TMS) δ(ppm): 13.61(1H,d,J=11.3 Hz), 7.2–7.5(5H,m), 6.9–7.1(5H,m), 6.77(1H,d,J=8.1 Hz), 6.64 (1H,d,J=1.6 Hz), 6.56(1H,dd,J=8.1,1.6 Hz), 5.46(1H,br), 5.13(2H,s), 3.83(3H,s), 3.4–3.6(2H,m), 2.73(2H,t,J=6.8 Hz), 2.33(3H,s).

Reference Production Example 6

2.14 g (11.97 mmol) of crude 2-(3-methoxy-4-benzyloxyphenyl)ethylamine, 1.45 g (14.36 mmol) of triethylamine and 20 ml of tetrahydrofuran were mixed and cooled to about 0° C. and then 2.26 g (11.97 mmol) of (4-chlorophenyl)acetyl chloride was added dropwise thereto. The mixture was stirred at 0° C. for 30 minutes and further at room temperature for 2 hours. Water was added to the reaction mixture, which was followed by extracted with ethyl acetate, washed with 5% hydrochloric acid and saturated brine subsequently, dried over anhydrous magnesium sulfate and the solvent was distilled off under reduced pressure. The residue was washed with hexane and dried to give 3.70 g of N-[2-(4-benzyloxy-3-methoxyphenyl)ethyl]-2-(4-chlorophenyl)acetamide.

$^1$H-NMR(CDCl$_3$, TMS) δ(ppm): 7.2–7.5(7H,m), 7.0–7.1 (2H,m), 6.73(1H,d, J=8.3 Hz), 6.63(1H,d,J=2.0Hz), 6.43 (1H,dd,J=8.0,2.0Hz), 5.29(1H,br), 5.14(2H,s), 3.84(3H,s), 3.4–3.5(4H,m), 2.66(2H,t,J=6.8 Hz).

2.25 g (5.49 mmol) of N-[2-(4-benzyloxy-3-methoxyphenyl)ethyl]-2-(4-chlorophenyl)acetamide and 2.39 g (13.73 mmol) of t-butoxybis(dimethylamino) methane were mixed and stirred at 90° C. for 1.5 hours. The reaction mixture was cooled and tetrahydrofuran was added thereto. The reaction mixture was acidified with 5% hydrochloric acid and stirred at room temperature for 2 hours. After the solvent was distilled off under reduced pressure, water and 5% hydrochloric acid were added to the residue, which was followed by extracted with ethyl acetate, washed with saturated brine twice, dried over anhydrous magnesium sulfate and the solvent was distilled off under reduced pressure. The residue was subjected to silica gel column chromatography (eluent, hexane:ethyl acetate=2:1) to give 1.50 g of N-[2-(4-benzyloxy-3-methoxyphenyl)ethyl]-3-hydroxy-2-(4-chlorophenyl)acrylamide.

$^1$H-NMR(CDCl$_3$, TMS) δ(ppm): 13.67(1H,d,J=11.0 Hz), 7.2–7.5(7H,m), 6.9–7.1(3H,m), 6.76(1H,d,J=8.3 Hz), 6.65 (1H,d,J=1.8 Hz), 6.52(1H,dd,J=8.0,2.0 Hz), 5.32(1H,br), 5.15(2H,s), 3.84(3H,s), 3.4–3.6(2H,m), 2.73(2H,t,J=6.8 Hz).

Reference Production Example 7

Two grams (2.00 g) of N-[2-(4-benzyloxy-3-methoxyphenyl)ethyl]-3-hydroxy-2-(4-methylphenyl)acrylamide (4.79 mmol), 1.21 g (7.19 mmol) of 48% hydrobromic acid and 20 ml of acetic acid were mixed and stirred at 80° C. for 1.5 hours. The solvent was distilled off from the reaction mixture under reduced pressure and the residue was subjected to silica gel column chromatography (eluent, hexane:ethyl acetate=2:1) to give 630 mg of 3-hydroxy-N-[2-(4-hydroxy-3-methoxyphenyl)ethyl]-2-(4-methylphenyl)acrylamide.

$^1$H-NMR(CDCl$_3$, TMS) δ(ppm): 13.6(1H,d,J=11.3 Hz), 6.9–7.2(5H,m), 6.80(1H,d), J=7.8 Hz), 6.5–6.6(2H,m), 5.4–5.5(2H,m), 3.83(3H,s), 3.4–3.6(2H,m), 2.74(2H,t,J=6.9 Hz), 2.35(3H,s).

Reference Production Example 8

1.60 g (3.66 mmol) of N-[2-(4-benzyloxy-3-methoxyphenyl)ethyl]-3-hydroxy-2-(4-chlorophenyl)acrylamide, 925 mg (5.49 mmol) of 48% hydrobromic acid and 15 ml of acetic acid were mixed and stirred at 80° C. for 1.5 hours. Water was added to the reaction mixture, which was followed by extracted with ethyl acetate twice, washed with saturated brine twice, dried over anhydrous magnesium sulfate and the solvent was distilled off under reduced pressure. The residue was subjected to silica gel column chromatography (eluent, hexane:ethyl acetate=2:1) to give 600 mg of 2-(4-chlorophenyl)-3-hydroxy-N-[2-(4-hydroxy-3-methoxyphenyl)ethyl]acrylamide.

$^1$H-NMR(CDCl$_3$, TMS) δ(ppm): 13.6(1H,d,J=11.3 Hz), 7.2–7.4(2H,m), 7.0–7.1(3H, m), 6.82(1H,d,J=6.7,1.7 Hz), 6.5–6.6(2H,m), 5.54(1H,s), 5.32(1H,br), 3.83(3H,s), 3.4–3.6 (2H,m), 2.74(2H,t,J=6.9 Hz).

Reference Production Example 9

4.02 g (55.0 mmol) of butylamine was added dropwise to a mixture of 12.1 g (50.0 mmol) of 4-benzyloxy-3-methoxybenzaldehyde, 5.63 g (75.0 mmol) of nitroethane and 120 ml of acetic acid and refluxed for 5 hours by heating. The reaction mixture was cooled and extracted with ethyl acetate, washed with saturated brine, dried over anhydrous magnesium sulfate and the solvent was distilled off under reduced pressure. The residue was subjected to silica gel column chromatography (eluent, hexane:ethyl acetate=4:1) to give 2.70 g of 1-benzyloxy-2-methoxy-4-(2-nitropropenyl)benzene.

$^1$H-NMR(CDCl$_3$, TMS) δ(ppm): 8.04(1H,s), 7.3–7.5(5H, m), 6.9–7.1(3H,m), 5.21(2H,s), 3.92(3H,s), 2.47(3H,s).

To a mixture of 1.03 g (27.1 mmol) of lithium aluminum hydride and 20 ml of anhydrous tetrahydrofuran, an anhydrous tetrahydrofuran solution of 2.70 g (9.03 mmol) of 1-benzyloxy-2-methoxy-4-(2-nitropropenyl)benzene was added dropwise under vigorous stirring over about 90 minutes and refluxed for 2 hours by heating. The reaction mixture was cooled and aqueous sodium hydroxide solution was added thereto. After the precipitates were filtered off with celite-precoated glass filter, the solvent was distilled off from the filtrate under reduced pressure. The residue was extracted with ethyl acetate, washed with saturated brine, dried over potassium carbonate and the solvent was distilled off under reduced pressure to give 2.30 g of crude 2-(4-benzyloxy-3-methoxyphenyl)-1-methylethylamine.

$^1$H-NMR(CDCl$_3$, TMS) δ(ppm): 7.2–7.5(5H,m), 6.6–6.9 (3H,m), 5.12(2H,s), 3.87(3H,s), 3.1–3.2(1H,m), 2.4–2.8(2H, m), 1.4–2.0(2H,br), 1.11(3H,d,J=6.3 Hz).

2.30 g (8.48 mmol) of crude 2-(4-benzyloxy-3-methoxyphenyl)-1-methylethylamine, 1.03 g (10.2 mmol) of triethylamine and 25 ml of tetrahydrofuran were mixed and cooled to about 0° C. and then 1.42 g (8.48 mmol) of (4-methylphenyl)acetyl chloride was added dropwise thereto. The mixture was stirred at 0° C. for 30 minutes and further at room temperature for 2 hours. Water was added to the reaction mixture, which was followed by extracted with ethyl acetate, washed with 5% hydrochloric acid and saturated brine subsequently, dried over anhydrous magnesium sulfate and the solvent was distilled off under reduced pressure. The residue was washed with hexane and dried to give 2.40 g of N-[2-(4-benzyloxy-3-methoxyphenyl)-1-methylethyl]-2-(4-methylphenyl) acetamide.

$^1$H-NMR(CDCl$_3$, TMS) δ(ppm): 7.3–7.5(5H,m), 6.9–7.1 (4H,m), 6.72(1H,d,J=8.1 Hz), 6.62(1H,d,J=1.9 Hz), 6.42 (1H,dd,J=2.0,8.1 Hz), 5.1–5.3(2H,m), 4.1–4.3(1H,m), 3.83 (3H,s), 3.45(2H,s), 2.59(2H,d,J=6.4 Hz), 2.33(3H,s), 1.04 (3H,d,J=6.6 Hz).

2.40 g (5.95 mmol) of N-[2-(4-benzyloxy-3-methoxyphenyl)-1-methylethyl]-2-(4-methylphenyl)acetamide and 3.10 g (17.8 mmol) of t-butoxybis(dimethylamino) methane were mixed and stirred at 80° C. for 2 hours. The reaction mixture was cooled and tetrahydrofuran was added thereto. The reaction mixture was acidified with hydrochloric acid and stirred at room temperature for 2 hours. After the solvent was distilled off under reduced pressure, the residue was extracted with chloroform washed with saturated brine twice, dried over anhydrous magnesium sulfate and the solvent was distilled off under reduced pressure. The residue was subjected to silica gel chromatography (eluent, hexane:ethyl acetate=3:2) and dried to give 1.90 g of N-[2-(4-benzyloxy-3-methoxyphenyl)-1-methylethyl]-3-hydroxy-2-(4-methylphenyl)acrylamide.

$^1$H-NMR(CDCl$_3$, TMS) δ(ppm): 13.65(1H,d,J=11.2 Hz), 7.2–7.5(5H,m), 6.9–7.2(5H, m), 6.76(1H,d,J=8.2 Hz), 6.63 (1H,d,J=1.88 Hz), 6.52(1H,dd,J=8.1,1.9Hz), 5.28(2H,d, J=7.6 Hz), 5.14(2H,s), 4.2–4.4(1H,d), 3.83(3H,s), 3.6–3.8 (2H,m), 2.35(3H,s), 1.11(3H,d, J=6.5 Hz).

1.90 g (4.41 mmol) of N-[2-(4-benzyloxy-3-methoxyphenyl)-1-methylethyl]-3-hydroxy-2-(4-methylphenyl)acrylamide, 0.99 g (17.6 mmol) of 10% aqueous potassium hydroxide solution, 716 mg (2.20 mmol) of tetrabutylammonium bromide and 20 ml of ethylene glycol dimethyl ether were mixed and chlorodifluoromethane gas was blown thereto at room temperature to 50° C. After a sample was taken out from the reaction mixture and the disappearance of the starting material was confirmed by thin layer chromatograph analysis, the reaction mixture was cooled. Then, 5% hydrochrolic acid was added to the reaction mixture, which was followed by extracted with ethyl acetate, washed with 5% hydrochrolic acid, saturated brine subsequently, dried over anhydrous magnesium sulfate and concentrated under reduced pressure. The residue was washed with hexane to give 1.80 g of N-[2-(4-benzyloxy-3-methoxyphenyl)-1-methylethyl]-3-difluoromethoxy-2-(4-methylphenyl)acrylamide.

$^1$H-NMR(CDCl$_3$, TMS) δ(ppm): 7.2–7.5(5H,m), 7.0–7.2 (4H,m), 6.7–6.9(4H,m), 6.63 (1H,dd,J=8.0,1.8 Hz), 6.30 (1H,t,J=71.7 Hz), 5.79(1H,d,J=8.1 Hz), 5.13(2H,s), 4.3–4.6 (1H,m), 3.83(3H,s), 2.6–2.9(2H,m), 2.33(3H,s), 1.18(3H,d, J=6.6 Hz).

1.80 g (3.74 mmol) of N-[2-(4-benzyloxy-3-methoxyphenyl)-1-methylethyl]-3-difluoromethoxy-2-(4-methylphenyl)acrylamide, 693 mg (4.11 mmol) of 48% hydrobromic acid and 20 ml of acetic acid were mixed and stirred at 80° C. for 2 hours. The solvent was distilled off from the reaction mixture under reduced pressure and the residue was subjected to silica gel column chromatography (eluent, hexane:ethyl acetate=2:1) to give 1.10 g of 3-difluoromethoxy-N-[2-(4-hydroxy-3-methoxyphenyl)-1-methylethyl]-2-(4-methylphenyl)acrylamide.

$^1$H-NMR(CDCl$_3$, TMS) δ(ppm): 7.1–7.2(4H,m), 6.6–6.9 (4H,m), 6.37(1H,t, J=71.5 Hz), 5.79(1H,d,J=7.7 Hz), 5.58 (1H,s), 4.3–4.5(1H,m), 3.82(3H,s), 2.6–2.9(2H,m), 2.34(3H, s), 1.18(3H,d,J=6.5 Hz).

Examples of the present compounds are given with their compound numbers below.

Compound given by formula [I]:

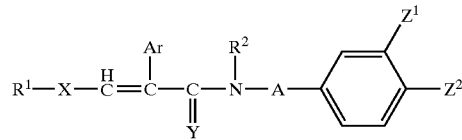

| Nos. | R¹X | Ar | Y | R² | A | Z¹ | Z² |
|---|---|---|---|---|---|---|---|
| 1001 | CH₂FO | C₆H₅ | O | H | CH₂CH₂ | CH₃O | CH₃O |
| 1002 | CHF₂O | C₆H₅ | O | H | CH₂CH₂ | CH₃O | CH₃O |
| 1003 | CF₃O | C₆H₅ | O | H | CH₂CH₂ | CH₃O | CH₃O |
| 1004 | CH₂FO | 4-CH₃C₆H₄ | O | H | CH₂CH₂ | CH₃O | CH₃O |
| 1005 | CHF₂O | 4-CH₃C₆H₄ | O | H | CH₂CH₂ | CH₃O | CH₃O |
| 1006 | CF₃O | 4-CH₃C₆H₄ | O | H | CH₂CH₂ | CH₃O | CH₃O |
| 1007 | CH₂FO | 4-C₂H₅C₆H₄ | O | H | CH₂CH₂ | CH₃O | CH₃O |
| 1008 | CHF₂O | 4-C₂H₅C₆H₄ | O | H | CH₂CH₂ | CH₃O | CH₃O |
| 1009 | CF₃O | 4-C₂H₅C₆H₄ | O | H | CH₂CH₂ | CH₃O | CH₃O |
| 1010 | CH₂FO | 4-CH₃CH₂CH₂C₆H₄ | O | H | CH₂CH₂ | CH₃O | CH₃O |
| 1011 | CHF₂O | 4-CH₃CH₂CH₂C₆H₄ | O | H | CH₂CH₂ | CH₃O | CH₃O |
| 1012 | CF₃O | 4-CH₃CH₂CH₂C₆H₄ | O | H | CH₂CH₂ | CH₃O | CH₃O |
| 1013 | CH₂FO | 4-FC₆H₄ | O | H | CH₂CH₂ | CH₃O | CH₃O |
| 1014 | CHF₂O | 4-FC₆H₄ | O | H | CH₂CH₂ | CH₃O | CH₃O |
| 1015 | CF₃O | 4-FC₆H₄ | O | H | CH₂CH₂ | CH₃O | CH₃O |
| 1016 | CH₂FO | 4-ClC₆H₄ | O | H | CH₂CH₂ | CH₃O | CH₃O |
| 1017 | CHF₂O | 4-ClC₆H₄ | O | H | CH₂CH₂ | CH₃O | CH₃O |
| 1018 | CF₃O | 4-ClC₆H₄ | O | H | CH₂CH₂ | CH₃O | CH₃O |
| 1019 | CH₂FO | 4-BrC₆H₄ | O | H | CH₂CH₂ | CH₃O | CH₃O |
| 1020 | CHF₂O | 4-BrC₆H₄ | O | H | CH₂CH₂ | CH₃O | CH₃O |
| 1021 | CF₃O | 4-BrC₆H₄ | O | H | CH₂CH₂ | CH₃O | CH₃O |
| 1022 | CH₂FO | 4-CH₃OC₆H₄ | O | H | CH₂CH₂ | CH₃O | CH₃O |
| 1023 | CHF₂O | 4-CH₃OC₆H₄ | O | H | CH₂CH₂ | CH₃O | CH₃O |
| 1024 | CF₃O | 4-CH₃OC₆H₄ | O | H | CH₂CH₂ | CH₃O | CH₃O |
| 1025 | CH₂FO | 4-CH₃SC₆H₄ | O | H | CH₂CH₂ | CH₃O | CH₃O |
| 1026 | CHF₂O | 4-CH₃SC₆H₄ | O | H | CH₂CH₂ | CH₃O | CH₃O |
| 1027 | CF₃O | 4-CH₃SC₆H₄ | O | H | CH₂CH₂ | CH₃O | CH₃O |
| 1028 | CH₂FO | 4-CF₃C₆H₄ | O | H | CH₂CH₂ | CH₃O | CH₃O |
| 1029 | CHF₂O | 4-CF₃C₆H₄ | O | H | CH₂CH₂ | CH₃O | CH₃O |
| 1030 | CF₃O | 4-CF₃C₆H₄ | O | H | CH₂CH₂ | CH₃O | CH₃O |
| 1031 | CH₂FO | 4-(CH₃)₃CC₆H₄ | O | H | CH₂CH₂ | CH₃O | CH₃O |
| 1032 | CHF₂O | 4-(CH₃)₃CC₆H₄ | O | H | CH₂CH₂ | CH₃O | CH₃O |
| 1033 | CF₃O | 4-(CH₃)₃CC₆H₄ | O | H | CH₂CH₂ | CH₃O | CH₃O |
| 1034 | CH₂FO | 3-CH₃C₆H₄ | O | H | CH₂CH₂ | CH₃O | CH₃O |
| 1035 | CHF₂O | 3-CH₃C₆H₄ | O | H | CH₂CH₂ | CH₃O | CH₃O |
| 1036 | CF₃O | 3-CH₃C₆H₄ | O | H | CH₂CH₂ | CH₃O | CH₃O |
| 1037 | CH₂FO | 3-C₂H₅C₆H₄ | O | H | CH₂CH₂ | CH₃O | CH₃O |
| 1038 | CHF₂O | 3-C₂H₅C₆H₄ | O | H | CH₂CH₂ | CH₃O | CH₃O |
| 1039 | CF₃O | 3-C₂H₅C₆H₄ | O | H | CH₂CH₂ | CH₃O | CH₃O |
| 1040 | CH₂FO | 3-CH₃CH₂CH₂C₆H₄ | O | H | CH₂CH₂ | CH₃O | CH₃O |
| 1041 | CHF₂O | 3-CH₃CH₂CH₂C₆H₄ | O | H | CH₂CH₂ | CH₃O | CH₃O |
| 1042 | CF₃O | 3-CH₃CH₂CH₂C₆H₄ | O | H | CH₂CH₂ | CH₃O | CH₃O |
| 1043 | CH₂FO | 3-FC₆H₄ | O | H | CH₂CH₂ | CH₃O | CH3Q |
| 1044 | CHF₂O | 3-FC₆H₄ | O | H | CH₂CH₂ | CH₃O | CH₃O |
| 1045 | CF₃O | 3-FC₆H₄ | O | H | CH₂CH₂ | CH3Q | CH₃O |
| 1046 | CH₂FO | 3-ClC₆H₄ | O | H | CH₂CH₂ | CH₃O | CH₃O |
| 1047 | CHF₂O | 3-ClC₆H₄ | O | H | CH₂CH₂ | CH₃O | CH₃O |
| 1048 | CF₃O | 3-ClC₆H₄ | O | H | CH₂CH₂ | CH₃O | CH₃O |
| 1049 | CH₂FO | 3-BrC₆H₄ | O | H | CH₂CH₂ | CH₃O | CH₃O |
| 1050 | CHF₂O | 3-BrC₆H₄ | O | H | CH₂CH₂ | CH₃O | CH₃O |
| 1051 | CF₃O | 3-BrC₆H₄ | O | H | CH₂CH₂ | CH₃O | CH₃O |
| 1052 | CH₂FO | 3-CH₃OC₆H₄ | O | H | CH₂CH₂ | CH₃O | CH₃O |
| 1053 | CHF₂O | 3-CH₃OC₆H₄ | O | H | CH₂CH₂ | CH₃O | CH₃O |
| 1054 | CF₃O | 3-CH₃OC₆H₄ | O | H | CH₂CH₂ | CH₃O | CH₃O |
| 1055 | CH₂FO | 3-CH₃SC₆H₄ | O | H | CH₂CH₂ | CH₃O | CH₃O |
| 1056 | CHF₂O | 3-CH₃SC₆H₄ | O | H | CH₂CH₂ | CH₃O | CH₃O |
| 1057 | CF₃O | 3-CH₃SC₆H₄ | O | H | CH₂CH₂ | CH₃O | CH₃O |
| 1058 | CH₂FO | 3-CF₃C₆H₄ | O | H | CH₂CH₂ | CH₃O | CH₃O |
| 1059 | CHF₂O | 3-CF₃C₆H₄ | O | H | CH₂CH₂ | CH₃O | CH₃O |
| 1060 | CF₃O | 3-CF₃C₆H₄ | O | H | CH₂CH₂ | CH₃O | CH₃O |
| 1061 | CH₂FO | 3,4-F₂C₆H₃ | O | H | CH₂CH₂ | CH₃O | CH₃O |
| 1062 | CHF₂O | 3,4-F₂C₆H₃ | O | H | CH₂CH₂ | CH₃O | CH₃O |
| 1063 | CF₃O | 3,4-F₂C₆H₃ | O | H | CH₂CH₂ | CH₃O | CH₃O |
| 1064 | CH₂FO | 3,4-Cl₂C₆H₃ | O | H | CH₂CH₂ | CH₃O | CH₃O |
| 1065 | CHF₂O | 3,4-Cl₂C₆H₃ | O | H | CH₂CH₂ | CH₃O | CH₃O |
| 1066 | CF₃O | 3,4-Cl₂C₆H₃ | O | H | CH₂CH₂ | CH₃O | CH₃O |
| 1067 | CH₂FO | 3,4-Br₂C₆H₃ | O | H | CH₂CH₂ | CH₃O | CH₃O |
| 1068 | CHF₂O | 3,4-Br₂C₆H₃ | O | H | CH₂CH₂ | CH₃O | CH₃O |
| 1069 | CF₃O | 3,4-Br₂C₆H₃ | O | H | CH₂CH₂ | CH₃O | CH₃O |

-continued

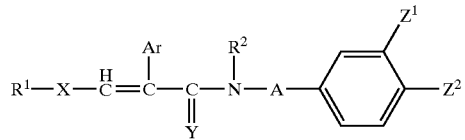

| Nos. | R¹X | Ar | Y | R² | A | Z¹ | Z² |
|---|---|---|---|---|---|---|---|
| 1070 | CH₂FO | 3,4-(CH₃)₂C₆H₃ | O | H | CH₂CH₂ | CH₃O | CH₃O |
| 1071 | CHF₂O | 3,4-(CH₃)₂C₆H₃ | O | H | CH₂CH₂ | CH₃O | CH₃O |
| 1072 | CF₃O | 3,4-(CH₃)₂C₆H₃ | O | H | CH₂CH₂ | CH₃O | CH₃O |
| 1073 | CH₂FO | 3,4-(CH₃O)₂C₆H₃ | O | H | CH₂CH₂ | CH₃O | CH₃O |
| 1074 | CHF₂O | 3,4-(CH₃O)₂C₆H₃ | O | H | CH₂CH₂ | CH₃O | CH₃O |
| 1075 | CF₃O | 3,4-(CH₃O)₂C₆H₃ | O | H | CH₂CH₂ | CH₃O | CH₃O |
| 1076 | CH₂FO | 3,4-(CF₃)₂C₆H₃ | O | H | CH₂CH₂ | CH₃O | CH₃O |
| 1077 | CHF₂O | 3,4-(CF₃)₂C₆H₃ | O | H | CH₂CH₂ | CH₃O | CH₃O |
| 1078 | CF₃O | 3,4-(CF₃)₂C₆H₃ | O | H | CH₂CH₂ | CH₃O | CH₃O |
| 1079 | CH₂FO | 4-Cl-3-CH₃C₆H₃ | O | H | CH₂CH₂ | CH₃O | CH₃O |
| 1080 | CHF₂O | 4-Cl-3-CH₃C₆H₃ | O | H | CH₂CH₂ | CH₃O | CH₃O |
| 1081 | CF₃O | 4-Cl-3-CH₃C₆H₃ | O | H | CH₂CH₂ | CH₃O | CH₃O |
| 1082 | CH₂FO | 3-Cl-4-CH₃C₆H₃ | O | H | CH₂CH₂ | CH₃O | CH₃O |
| 1083 | CHF₂O | 3-Cl-4-CH₃C₆H₃ | O | H | CH₂CH₂ | CH₃O | CH₃O |
| 1084 | CF₃O | 3-Cl-4-CH₃C₆H₃ | O | H | CH₂CH₂ | CH₃O | CH₃O |
| 1085 | CH₂FO | 4-Cl-3-CH₃OC₆H₃ | O | H | CH₂CH₂ | CH₃O | CH₃O |
| 1086 | CHF₂O | 4-Cl-3-CH₃OC₆H₃ | O | H | CH₂CH₂ | CH₃O | CH₃O |
| 1087 | CF₃O | 4-Cl-3-CH₃OC₆H₃ | O | H | CH₂CH₂ | CH₃O | CH₃O |
| 1088 | CH₂FO | 3-Cl-4-CH₃OC₆H₃ | O | H | CH₂CH₂ | CH₃O | CH₃O |
| 1089 | CHF₂O | 3-Cl-4-CH₃OC₆H₃ | O | H | CH₂CH₂ | CH₃O | CH₃O |
| 1090 | CF₃O | 3-Cl-4-CH₃OC₆H₃ | O | H | CH₂CH₂ | CH₃O | CH₃O |
| 1091 | CH₂FO | 3,4-(OCH₂O)C₆H₃ | O | H | CH₂CH₂ | CH₃O | CH₃O |
| 1092 | CHF₂O | 3,4-(OCH₂O)C₆H₃ | O | H | CH₂CH₂ | CH₃O | CH₃O |
| 1093 | CF₃O | 3,4-(OCH₂O)C₆H₃ | O | H | CH₂CH₂ | CH₃O | CH₃O |
| 1094 | CH₂FO | 3,4-(OCH₂CH₂O)C₆H₃ | O | H | CH₂CH₂ | CH₃O | CH₃O |
| 1095 | CHF₂O | 3,4-(OCH₂CH₂O)C₆H₃ | O | H | CH₂CH₂ | CH₃O | CH₃O |
| 1096 | CF₃O | 3,4-(OCH₂CH₂O)C₆H₃ | O | H | CH₂CH₂ | CH₃O | CH₃O |
| 1097 | CH₂FO | 3,4-(OCF₂O)C₆H₃ | O | H | CH₂CH₂ | CH₃O | CH₃O |
| 1098 | CHF₂O | 3,4-(OCF₂O)C₆H₃ | O | H | CH₂CH₂ | CH₃O | CH₃O |
| 1099 | CF₃O | 3,4-(OCF₂O)C₆H₃ | O | H | CH₂CH₂ | CH₃O | CH₃O |
| 1100 | CH₂FO | 3,4-(CH₂)₃C₆H₃ | O | H | CH₂CH₂ | CH₃O | CH₃O |
| 1101 | CHF₂O | 3,4-(CH₂)₃C₆H₃ | O | H | CH₂CH₂ | CH₃O | CH₃O |
| 1102 | CF₃O | 3,4-(CH₂)₃C₆H₃ | O | H | CH₂CH₂ | CH₃O | CH₃O |
| 1103 | CH₂FO | 3,4-(CH₂)₄C₆H₃ | O | H | CH₂CH₂ | CH₃O | CH₃O |
| 1104 | CHF₂O | 3,4-(CH₂)₄C₆H₃ | O | H | CH₂CH₂ | CH₃O | CH₃O |
| 1105 | CF₃O | 3,4-(CH₂)₄C₆H₃ | O | H | CH₂CH₂ | CH₃O | CH₃O |
| 1106 | CH₂FO | 3,4-(CH₂)₅C₆H₃ | O | H | CH₂CH₂ | CH₃O | CH₃O |
| 1107 | CHF₂O | 3,4-(CH₂)₅C₆H₃ | O | H | CH₂CH₂ | CH₃O | CH₃O |
| 1108 | CF₃O | 3,4-(CH₂)₅C₆H₃ | O | H | CH₂CH₂ | CH₃O | CH₃O |
| 1109 | CH₂FO | C₆H₅ | O | CH₃ | CH(CH₃)CH₂ | CH₃O | CH₃O |
| 1110 | CHF₂O | C₆H₅ | O | CH₃ | CH(CH₃)CH₂ | CH₃O | CH₃O |
| 1111 | CF₃O | C₆H₅ | O | CH₃ | CH(CH₃)CH₂ | CH₃O | CH₃O |
| 1112 | CH₂FO | 4-CH₃C₆H₄ | O | CH₃ | CH(CH₃)CH₂ | CH₃O | CH₃O |
| 1113 | CHF₂O | 4-CH₃C₆H₄ | O | CH₃ | CH(CH₃)CH₂ | CH₃O | CH₃O |
| 1114 | CF₃O | 4-CH₃C₆H₄ | O | CH₃ | CH(CH₃)CH₂ | CH₃O | CH₃O |
| 1115 | CH₂FO | 4-ClC₆H₄ | O | CH₃ | CH(CH₃)CH₂ | CH₃O | CH₃O |
| 1116 | CHF₂O | 4-ClC₆H₄ | O | CH₃ | CH(CH₃)CH₂ | CH₃O | CH₃O |
| 1117 | CF₃O | 4-ClC₆H₄ | O | CH₃ | CH(CH₃)CH₂ | CH₃O | CH₃O |
| 1118 | CH₂FO | 3,4-(OCF₂O)C₆H₃ | O | CH₃ | CH(CH₃)CH₂ | CH₃O | CH₃O |
| 1119 | CHF₂O | 3,4-(OCF₂O)C₆H₃ | O | CH₃ | CH(CH₃)CH₂ | CH₃O | CH₃O |
| 1120 | CF₃O | 3,4-(OCF₂O)C₆H₃ | O | CH₃ | CH(CH₃)CH₂ | CH₃O | CH₃O |
| 1121 | CH₂FO | 3,4-(CH₂)₃C₆H₃ | O | CH₃ | CH(CH₃)CH₂ | CH₃O | CH₃O |
| 1122 | CHF₂O | 3,4-(CH₂)₃C₆H₃ | O | CH₃ | CH(CH₃)CH₂ | CH₃O | CH₃O |
| 1123 | CF₃O | 3,4-(CH₂)₃C₆H₃ | O | CH₃ | CH(CH₃)CH₂ | CH₃O | CH₃O |
| 1124 | CH₂FO | 3,4-(CH₂)₄C₆H₃ | O | CH₃ | CH(CH₃)CH₂ | CH₃O | CH₃O |
| 1125 | CHF₂O | 3,4-(CH₂)₄C₆H₃ | O | CH₃ | CH(CH₃)CH₂ | CH₃O | CH₃O |
| 1126 | CF₃O | 3,4-(CH₂)₄C₆H₃ | O | H | CH(CH₃)CH₂ | CH₃O | CH₃O |
| 1127 | CH₂FO | C₆H₅ | O | H | CH₂CH₂ | CH₃O | C₂H₅O |
| 1128 | CHF₂O | C₆H₅ | O | H | CH₂CH₂ | CH₃O | C₂H₅O |
| 1129 | CF₃O | C₆H₅ | O | H | CH₂CH₂ | CH₃O | C₂H₅O |
| 1130 | CH₂FO | 4-CH₃C₆H₄ | O | H | CH₂CH₂ | CH₃O | C₂H₅O |
| 1131 | CHF₂O | 4-CH₃C₆H₄ | O | H | CH₂CH₂ | CH₃O | C₂H₅O |
| 1132 | CF₃O | 4-CH₃C₆H₄ | O | H | CH₂CH₂ | CH₃O | C₂H₅O |
| 1133 | CH₂FO | 4-ClC₆H₄ | O | H | CH₂CH₂ | CH₃O | C₂H₅O |
| 1134 | CHF₂O | 4-ClC₆H₄ | O | H | CH₂CH₂ | CH₃O | C₂H₅O |
| 1135 | CF₃O | 4-ClC₆H₄ | O | H | CH₂CH₂ | CH₃O | C₂H₅O |
| 1136 | CH₂FO | 3,4-(OCF₂O)C₆H₃ | O | H | CH₂CH₂ | CH₃O | C₂H₅O |
| 1137 | CHF₂O | 3,4-(OCF₂O)C₆H₃ | O | H | CH₂CH₂ | CH₃O | C₂H₅O |
| 1138 | CF₃O | 3,4-(OCF₂O)C₆H₃ | O | H | CH₂CH₂ | CH₃O | C₂H₅O |

-continued

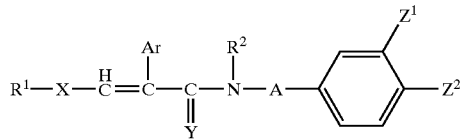

| Nos. | R¹X | Ar | Y | R² | A | Z¹ | Z² |
|---|---|---|---|---|---|---|---|
| 1139 | CH$_2$FO | 3,4-(CH$_2$)$_3$C$_6$H$_3$ | O | H | CH$_2$CH$_2$ | CH$_3$O | C$_2$H$_5$O |
| 1140 | CHF$_2$O | 3,4-(CH$_2$)$_3$C$_6$H$_3$ | O | H | CH$_2$CH$_2$ | CH$_3$O | C$_2$H$_5$O |
| 1141 | CF$_3$O | 3,4-(CH$_2$)$_3$C$_6$H$_3$ | O | H | CH$_2$CH$_2$ | CH$_3$O | C$_2$H$_5$O |
| 1142 | CH$_2$FO | 3,4-(CH$_2$)$_4$C$_6$H$_3$ | O | H | CH$_2$CH$_2$ | CH$_3$O | C$_2$H$_5$O |
| 1143 | CHF$_2$O | 3,4-(CH$_2$)$_4$C$_6$H$_3$ | O | H | CH$_2$CH$_2$ | CH$_3$O | C$_2$H$_5$O |
| 1144 | CF$_3$O | 3,4-(CH$_2$)$_4$C$_6$H$_3$ | O | H | CH$_2$CH$_2$ | CH$_3$O | C$_2$H$_5$O |
| 1145 | CH$_2$FO | C$_6$H$_5$ | S | H | CH$_2$CH$_2$ | CH$_3$O | CH$_3$O |
| 1146 | CHF$_2$O | C$_6$H$_5$ | S | H | CH$_2$CH$_2$ | CH$_3$O | CH$_3$O |
| 1147 | CF$_3$O | C$_6$H$_5$ | S | H | CH$_2$CH$_2$ | CH$_3$O | CH$_3$O |
| 1148 | CH$_2$FO | 4-CH$_3$C$_6$H$_4$ | S | H | CH$_2$CH$_2$ | CH$_3$O | CH$_3$O |
| 1149 | CHF$_2$O | 4-CH$_3$C$_6$H$_4$ | S | H | CH$_2$CH$_2$ | CH$_3$O | CH$_3$O |
| 1150 | CF$_3$O | 4-CH$_3$C$_6$H$_4$ | S | H | CH$_2$CH$_2$ | CH$_3$O | CH$_3$O |
| 1151 | CH$_2$FO | 4-ClC$_6$H$_4$ | S | H | CH$_2$CH$_2$ | CH$_3$O | CH$_3$O |
| 1152 | CHF$_2$O | 4-ClC$_6$H$_4$ | S | H | CH$_2$CH$_2$ | CH$_3$O | CH$_3$O |
| 1153 | CF$_3$O | 4-ClC$_6$H$_4$ | S | H | CH$_2$CH$_2$ | CH$_3$O | CH$_3$O |
| 1154 | CH$_2$FO | 3,4-(OCF$_2$O)C$_6$H$_3$ | S | H | CH$_2$CH$_2$ | CH$_3$O | CH$_3$O |
| 1155 | CHF$_2$O | 3,4-(OCF$_2$O)C$_6$H$_3$ | S | H | CH$_2$CH$_2$ | CH$_3$O | CH$_3$O |
| 1156 | CF$_3$O | 3,4-(OCF$_2$O)C$_6$H$_3$ | S | H | CH$_2$CH$_2$ | CH$_3$O | CH$_3$O |
| 1157 | CH$_2$FO | 3,4-(CH$_2$)$_3$C$_6$H$_3$ | S | H | CH$_2$CH$_2$ | CH$_3$O | CH$_3$O |
| 1158 | CHF$_2$O | 3,4-(CH$_2$)$_3$C$_6$H$_3$ | S | H | CH$_2$CH$_2$ | CH$_3$O | CH$_3$O |
| 1159 | CF$_3$O | 3,4-(CH$_2$)$_3$C$_6$H$_3$ | S | H | CH$_2$CH$_2$ | CH$_3$O | CH$_3$O |
| 1160 | CH$_2$FO | 3,4-(CH$_2$)$_4$C$_6$H$_3$ | S | H | CH$_2$CH$_2$ | CH$_3$O | CH$_3$O |
| 1161 | CHF$_2$O | 3,4-(CH$_2$)$_4$C$_6$H$_3$ | S | H | CH$_2$CH$_2$ | CH$_3$O | CH$_3$O |
| 1162 | CF$_3$O | 3,4-(CH$_2$)$_4$C$_6$H$_3$ | S | H | CH$_2$CH$_2$ | CH$_3$O | CH$_3$O |
| 1163 | CH$_2$FS | C$_6$H$_5$ | O | H | CH$_2$CH$_2$ | CH$_3$O | CH$_3$O |
| 1164 | CHF$_2$S | C$_6$H$_5$ | O | H | CH$_2$CH$_2$ | CH$_3$O | CH$_3$O |
| 1165 | CF$_3$S | C$_6$H$_5$ | O | H | CH$_2$CH$_2$ | CH$_3$O | CH$_3$O |
| 1166 | CH$_2$FS | 4-CH$_3$C$_6$H$_4$ | O | H | CH$_2$CH$_2$ | CH$_3$O | CH$_3$O |
| 1167 | CHF$_2$S | 4-CH$_3$C$_6$H$_4$ | O | H | CH$_2$CH$_2$ | CH$_3$O | CH$_3$O |
| 1168 | CF$_3$S | 4-CH$_3$C$_6$H$_4$ | O | H | CH$_2$CH$_2$ | CH$_3$O | CH$_3$O |
| 1169 | CH$_2$FS | 4-ClC$_6$H$_4$ | O | H | CH$_2$CH$_2$ | CH$_3$O | CH$_3$O |
| 1170 | CHF$_2$S | 4-ClC$_6$H$_4$ | O | H | CH$_2$CH$_2$ | CH$_3$O | CH$_3$O |
| 1171 | CF$_3$S | 4-ClC$_6$H$_4$ | O | H | CH$_2$CH$_2$ | CH$_3$O | CH$_3$O |
| 1172 | CH$_2$FS | 3,4-(OCF$_2$O)C$_6$H$_3$ | O | H | CH$_2$CH$_2$ | CH$_3$O | CH$_3$O |
| 1173 | CHF$_2$S | 3,4-(OCF$_2$O)C$_6$H$_3$ | O | H | CH$_2$CH$_2$ | CH$_3$O | CH$_3$O |
| 1174 | CF$_3$S | 3,4-(OCF$_2$O)C$_6$H$_3$ | O | H | CH$_2$CH$_2$ | CH$_3$O | CH$_3$O |
| 1175 | CH$_2$FS | 3,4-(CH$_2$)$_3$C$_6$H$_3$ | O | H | CH$_2$CH$_2$ | CH$_3$O | CH$_3$O |
| 1176 | CHF$_2$S | 3,4-(CH$_2$)$_3$C$_6$H$_3$ | O | H | CH$_2$CH$_2$ | CH$_3$O | CH$_3$O |
| 1177 | CF$_3$S | 3,4-(CH$_2$)$_3$C$_6$H$_3$ | O | H | CH$_2$CH$_2$ | CH$_3$O | CH$_3$O |
| 1178 | CH$_2$FS | 3,4-(CH$_2$)$_4$C$_6$H$_3$ | O | H | CH$_2$CH$_2$ | CH$_3$O | CH$_3$O |
| 1179 | CHF$_2$S | 3,4-(CH$_2$)$_4$C$_6$H$_3$ | O | H | CH$_2$CH$_2$ | CH$_3$O | CH$_3$O |
| 1180 | CF$_3$S | 3,4-(CH$_2$)$_4$C$_6$H$_3$ | O | H | CH$_2$CH$_2$ | CH$_3$O | CH$_3$O |
| 1181 | CH≡CCH$_2$O | C$_6$H$_5$ | O | H | CH$_2$CH$_2$ | CH$_3$O | CH$_3$O |
| 1182 | CH≡CCH$_2$O | 4-CH$_3$C$_6$H$_4$ | O | H | CH$_2$CH$_2$ | CH$_3$O | CH$_3$O |
| 1183 | CH≡CCH$_2$O | 4-C$_2$H$_5$C$_6$H$_4$ | O | H | CH$_2$CH$_2$ | CH$_3$O | CH$_3$O |
| 1184 | CH≡CCH$_2$O | 4-FC$_6$H$_4$ | O | H | CH$_2$CH$_2$ | CH$_3$O | CH$_3$O |
| 1185 | CH≡CCH$_2$O | 4-ClC$_6$H$_4$ | O | H | CH$_2$CH$_2$ | CH$_3$O | CH$_3$O |
| 1186 | CH≡CCH$_2$O | 4-BrC$_6$H$_4$ | O | H | CH$_2$CH$_2$ | CH$_3$O | CH$_3$O |
| 1187 | CH≡CCH$_2$O | 4-CH$_3$OC$_6$H$_4$ | O | H | CH$_2$CH$_2$ | CH$_3$O | CH$_3$O |
| 1188 | CH≡CCH$_2$O | 4-CF$_3$C$_6$H$_4$ | O | H | CH$_2$CH$_2$ | CH$_3$O | CH$_3$O |
| 1189 | CH≡CCH$_2$O | 4-(CH$_3$)$_3$CC$_6$H$_4$ | O | H | CH$_2$CH$_2$ | CH$_3$O | CH$_3$O |
| 1190 | CH≡CCH$_2$O | 3,4-Cl$_2$C$_6$H$_3$ | O | H | CH$_2$CH$_2$ | CH$_3$O | CH$_3$O |
| 1191 | CH≡CCH$_2$O | 3,4-(CH$_3$)$_2$C$_6$H$_3$ | O | H | CH$_2$CH$_2$ | CH$_3$O | CH$_3$O |
| 1192 | CH≡CCH$_2$O | 3,4-(OCH$_2$O)C$_6$H$_3$ | O | H | CH$_2$CH$_2$ | CH$_3$O | CH$_3$O |
| 1193 | CH≡CCH$_2$O | 3,4-(OCH$_2$CH$_2$O)C$_6$H$_3$ | O | H | CH$_2$CH$_2$ | CH$_3$O | CH$_3$O |
| 1194 | CH≡CCH$_2$O | 3,4-(OCF$_2$O)C$_6$H$_3$ | O | H | CH$_2$CH$_2$ | CH$_3$O | CH$_3$O |
| 1195 | CH≡CCH$_2$O | 3,4-(CH$_2$)$_3$C$_6$H$_3$ | O | H | CH$_2$CH$_2$ | CH$_3$O | CH$_3$O |
| 1196 | CH≡CCH$_2$O | 3,4-(CH$_2$)$_4$C$_6$H$_3$ | O | H | CH$_2$CH$_2$ | CH$_3$O | CH$_3$O |
| 1197 | CHBrF$_2$O | 4-CH$_3$C$_6$H$_4$ | O | H | CH$_2$CH$_2$ | CH$_3$O | CH$_3$O |
| 1198 | CHBrF$_2$O | 4-C$_2$H$_5$C$_6$H$_4$ | O | H | CH$_2$CH$_2$ | CH$_3$O | CH$_3$O |
| 1199 | CHBrF$_2$O | 4-ClC$_6$H$_4$ | O | H | CH$_2$CH$_2$ | CH$_3$O | CH$_3$O |
| 1200 | CHBrF$_2$O | 4-BrC$_6$H$_4$ | O | H | CH$_2$CH$_2$ | CH$_3$O | CH$_3$O |
| 1201 | CHBrF$_2$O | 4-CF$_3$C$_6$H$_4$ | O | H | CH$_2$CH$_2$ | CH$_3$O | CH$_3$O |
| 1202 | CHBrF$_2$O | 4-CH$_3$OC$_6$H$_4$ | O | H | CH$_2$CH$_2$ | CH$_3$O | CH$_3$O |
| 1203 | CHBrF$_2$O | 4-CF$_3$OC$_6$H$_4$ | O | H | CH$_2$CH$_2$ | CH$_3$O | CH$_3$O |
| 1204 | CHBrF$_2$O | 3,4-(CH$_2$)$_3$C$_6$H$_3$ | O | H | CH$_2$CH$_2$ | CH$_3$O | CH$_3$O |
| 1205 | CHBrF$_2$O | 3,4-(CH$_2$)$_4$C$_6$H$_3$ | O | H | CH$_2$CH$_2$ | CH$_3$O | CH$_3$O |
| 1206 | CHClF$_2$O | 4-CH$_3$C$_6$H$_4$ | O | H | CH$_2$CH$_2$ | CH$_3$O | CH$_3$O |
| 1207 | CHClF$_2$O | 4-C$_2$H$_5$C$_6$H$_4$ | O | H | CH$_2$CH$_2$ | CH$_3$O | CH$_3$O |

-continued

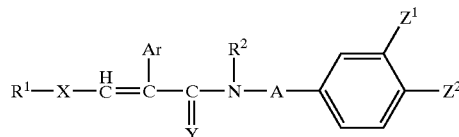

| Nos. | R¹X | Ar | Y | R² | A | Z¹ | Z² |
|---|---|---|---|---|---|---|---|
| 1208 | CHClF$_2$O | 4-ClC$_6$H$_4$ | O | H | CH$_2$CH$_2$ | CH$_3$O | CH$_3$O |
| 1209 | CHClF$_2$O | 4-BrC$_6$H$_4$ | O | H | CH$_2$CH$_2$ | CH$_3$O | CH$_3$O |
| 1210 | CHClF$_2$O | 4-CF$_3$C$_6$H$_4$ | O | H | CH$_2$CH$_2$ | CH$_3$O | CH$_3$O |
| 1211 | CHClF$_2$O | 4-CH$_3$OC$_6$H$_4$ | O | H | CH$_2$CH$_2$ | CH$_3$O | CH$_3$O |
| 1212 | CHClF$_2$O | 4-CF$_3$OC$_6$H$_4$ | O | H | CH$_2$CH$_2$ | CH$_3$O | CH$_3$O |
| 1213 | CHClF$_2$O | 3,4-(CH$_2$)$_3$C$_6$H$_3$ | O | H | CH$_2$CH$_2$ | CH$_3$O | CH$_3$O |
| 1214 | CHClF$_2$O | 3,4-(CH$_2$)$_4$C$_6$H$_3$ | O | H | CH$_2$CH$_2$ | CH$_3$O | CH$_3$O |
| 1215 | CCl≡CCH$_2$O | 4-CH$_3$C$_6$H$_4$ | O | H | CH$_2$CH$_2$ | CH$_3$O | CH$_3$O |
| 1216 | CCl≡CCH$_2$O | 4-C$_2$H$_5$C$_6$H$_4$ | O | H | CH$_2$CH$_2$ | CH$_3$O | CH$_3$O |
| 1217 | CCl≡CCH$_2$O | 4-ClC$_6$H$_4$ | O | H | CH$_2$CH$_2$ | CH$_3$O | CH$_3$O |
| 1218 | CCl≡CCH$_2$O | 4-BrC$_6$H$_4$ | O | H | CH$_2$CH$_2$ | CH$_3$O | CH$_3$O |
| 1219 | CCl≡CCH$_2$O | 4-CF$_3$C$_6$H$_4$ | O | H | CH$_2$CH$_2$ | CH$_3$O | CH$_3$O |
| 1220 | CCl≡CCH$_2$O | 4-CH$_3$OC$_6$H$_4$ | O | H | CH$_2$CH$_2$ | CH$_3$O | CH$_3$O |
| 1221 | CCl≡CCH$_2$O | 4-CF$_3$OC$_6$H$_4$ | O | H | CH$_2$CH$_2$ | CH$_3$O | CH$_3$O |
| 1222 | CCl≡CCH$_2$O | 3,4-(CH$_2$)$_3$C$_6$H$_3$ | O | H | CH$_2$CH$_2$ | CH$_3$O | CH$_3$O |
| 1223 | CCl≡CCH$_2$O | 3,4-(CH$_2$)$_4$C$_6$H$_3$ | O | H | CH$_2$CH$_2$ | CH$_3$O | CH$_3$O |
| 1224 | CCl$_2$=CHCH$_2$O | 4-CH$_3$C$_6$H$_4$ | O | H | CH$_2$CH$_2$ | CH$_3$O | CH$_3$O |
| 1225 | CCl$_2$=CHCH$_2$O | 4-C$_2$H$_5$C$_6$H$_4$ | O | H | CH$_2$CH$_2$ | CH$_3$O | CH$_3$O |
| 1226 | CCl$_2$=CHCH$_2$O | 4-ClC$_6$H$_4$ | O | H | CH$_2$CH$_2$ | CH$_3$O | CH$_3$O |
| 1227 | CCl$_2$=CHCH$_2$O | 4-BrC$_6$H$_4$ | O | H | CH$_2$CH$_2$ | CH$_3$O | CH$_3$O |
| 1228 | CCl$_2$=CHCH$_2$O | 4-CF$_3$C$_6$H$_4$ | O | H | CH$_2$CH$_2$ | CH$_3$O | CH$_3$O |
| 1229 | CCl$_2$=CHCH$_2$O | 4-CH$_3$OC$_6$H$_4$ | O | H | CH$_2$CH$_2$ | CH$_3$O | CH$_3$O |
| 1230 | CCl$_2$=CHCH$_2$O | 4-CF$_3$OC$_6$H$_4$ | O | H | CH$_2$CH$_2$ | CH$_3$O | CH$_3$O |
| 1231 | CCl$_2$=CHCH$_2$O | 3,4-(CH$_2$)$_3$C$_6$H$_3$ | O | H | CH$_2$CH$_2$ | CH$_3$O | CH$_3$O |
| 1232 | CCl$_2$=CHCH$_2$O | 3,4-(CH$_2$)$_4$C$_6$H$_3$ | O | H | CH$_2$CH$_2$ | CH$_3$O | CH$_3$O |
| 1233 | CH$_2$FCH$_2$O | 4-CH$_3$C$_6$H$_4$ | O | H | CH$_2$CH$_2$ | CH$_3$O | CH$_3$O |
| 1234 | CH$_2$FCH$_2$O | 4-C$_2$H$_5$C$_6$H$_4$ | O | H | CH$_2$CH$_2$ | CH$_3$O | CH$_3$O |
| 1235 | CH$_2$FCH$_2$O | 4-ClC$_6$H$_4$ | O | H | CH$_2$CH$_2$ | CH$_3$O | CH$_3$O |
| 1236 | CH$_2$FCH$_2$O | 4-BrC$_6$H$_4$ | O | H | CH$_2$CH$_2$ | CH$_3$O | CH$_3$O |
| 1237 | CH$_2$FCH$_2$O | 4-CF$_3$C$_6$H$_4$ | O | H | CH$_2$CH$_2$ | CH$_3$O | CH$_3$O |
| 1238 | CH$_2$FCH$_2$O | 4-CH$_3$OC$_6$H$_4$ | O | H | CH$_2$CH$_2$ | CH$_3$O | CH$_3$O |
| 1239 | CH$_2$FCH$_2$O | 4-CF$_3$OC$_6$H$_4$ | O | H | CH$_2$CH$_2$ | CH$_3$O | CH$_3$O |
| 1240 | CH$_2$FCH$_2$O | 3,4-(CH$_2$)$_3$C$_6$H$_3$ | O | H | CH$_2$CH$_2$ | CH$_3$O | CH$_3$O |
| 1241 | CH$_2$FCH$_2$O | 3,4-(CH$_2$)$_4$C$_6$H$_3$ | O | H | CH$_2$CH$_2$ | CH$_3$O | CH$_3$O |
| 1242 | CClF$_2$O | 2-naphthyl | O | H | CH$_2$CH$_2$ | CH$_3$O | CH$_3$O |
| 1243 | CBrF$_2$O | 2-naphthyl | O | H | CH$_2$CH$_2$ | CH$_3$O | CH$_3$O |
| 1244 | CH$_2$FCH$_2$O | 2-naphthyl | O | H | CH$_2$CH$_2$ | CH$_3$O | CH$_3$O |
| 1245 | CH≡CCH$_2$O | 2-naphthyl | O | H | CH$_2$CH$_2$ | CH$_3$O | CH$_3$O |
| 1246 | CH$_2$FO | 4-NO$_2$C$_6$H$_4$ | O | H | CH$_2$CH$_2$ | CH$_3$O | CH$_3$O |
| 1247 | CHF$_2$O | 4-NO$_2$C$_6$H$_4$ | O | H | CH$_2$CH$_2$ | CH$_3$O | CH$_3$O |
| 1248 | CF$_3$O | 4-NO$_2$C$_6$H$_4$ | O | H | CH$_2$CH$_2$ | CH$_3$O | CH$_3$O |
| 1249 | CH≡CCH$_2$O | 4-NO$_2$C$_6$H$_4$ | O | H | CH$_2$CH$_2$ | CH$_3$O | CH$_3$O |
| 1250 | CH$_2$FO | 4-(CH$_3$)$_2$CHC$_6$H$_4$ | O | H | CH$_2$CH$_2$ | CH$_3$O | CH$_3$O |
| 1251 | CHF$_2$O | 4-(CH$_3$)$_2$CHC$_6$H$_4$ | O | H | CH$_2$CH$_2$ | CH$_3$O | CH$_3$O |
| 1252 | CF$_3$O | 4-(CH$_3$)$_2$CHC$_6$H$_4$ | O | H | CH$_2$CH$_2$ | CH$_3$O | CH$_3$O |
| 1253 | CH≡CCH$_2$O | 4-(CH$_3$)$_2$CHC$_6$H$_4$ | O | H | CH$_2$CH$_2$ | CH$_3$O | CH$_3$O |
| 1254 | CH$_2$FO | 4-cyclopropylphenyl | O | H | CH$_2$CH$_2$ | CH$_3$O | CH$_3$O |
| 1255 | CHF$_2$O | 4-cyclopropylphenyl | O | H | CH$_2$CH$_2$ | CH$_3$O | CH$_3$O |
| 1256 | CF$_3$O | 4-cyclopropylphenyl | O | H | CH$_2$CH$_2$ | CH$_3$O | CH$_3$O |
| 1257 | CH≡CCH$_2$O | 4-cyclopropylphenyl | O | H | CH$_2$CH$_2$ | CH$_3$O | CH$_3$O |
| 1258 | CHF$_2$O | 3,4-(CH$_2$)$_4$C$_6$H$_3$ | O | H | CH$_2$CH$_2$ | CH$_3$O | CH$_3$CH$_2$CH$_2$O |
| 1259 | CHF$_2$O | 3,4-(CH$_2$)$_4$C$_6$H$_3$ | O | H | CH$_2$CH$_2$ | CH$_3$O | (CH$_3$)$_2$CHO |
| 1260 | CHF$_2$O | 3,4-(CH$_2$)$_4$C$_6$H$_3$ | O | H | CH$_2$CH$_2$ | CH$_3$O | cyclopropoxy |
| 1261 | CHF$_2$O | 3,4-(CH$_2$)$_4$C$_6$H$_3$ | O | H | CH$_2$CH$_2$ | CH$_3$O | Cyclopropyl-methoxy |
| 1262 | CHF$_2$O | 3,4-(CH$_2$)$_4$C$_6$H$_3$ | O | H | CH$_2$CH$_2$ | CH$_3$O | butoxy |
| 1263 | CHF$_2$O | 3,4-(CH$_2$)$_4$C$_6$H$_3$ | O | H | CH$_2$CH$_2$ | CH$_3$O | isobutoxy |
| 1264 | CHF$_2$O | 3,4-(CH$_2$)$_4$C$_6$H$_3$ | O | H | CH$_2$CH$_2$ | CH$_3$O | sec-butoxy |
| 1265 | CHF$_2$O | 3,4-(CH$_2$)$_4$C$_6$H$_3$ | O | H | CH$_2$CH$_2$ | CH$_3$O | t-butoxy |
| 1266 | CHF$_2$O | 3,4-(CH$_2$)$_4$C$_6$H$_3$ | O | H | CH$_2$CH$_2$ | CH$_3$O | allyloxy |
| 1267 | CHF$_2$O | 3,4-(CH$_2$)$_4$C$_6$H$_3$ | O | H | CH$_2$CH$_2$ | CH$_3$O | 2-butenyloxy |
| 1268 | CHF$_2$O | 3,4-(CH$_2$)$_4$C$_6$H$_3$ | O | H | CH$_2$CH$_2$ | CH$_3$O | CH≡CCH$_2$O |
| 1269 | CHF$_2$O | 3,4-(CH$_2$)$_4$C$_6$H$_3$ | O | H | CH$_2$CH$_2$ | CH$_3$O | 2-butynyloxy |
| 1270 | CHF$_2$O | 3,4-(CH$_2$)$_4$C$_6$H$_3$ | O | H | CH$_2$CH$_2$ | CH$_3$O | 2-pentynyl-oxy |
| 1271 | CHF$_2$O | 4-CH$_3$C$_6$H$_4$ | O | H | CH$_2$CH$_2$ | CH$_3$O | 1-methyl-2-propynyloxy |
| 1272 | CHF$_2$O | 3,4-(CH$_2$)$_4$C$_6$H$_3$ | O | H | CH$_2$CH$_2$ | CH$_3$O | 3-butynyloxy |
| 1273 | CHF$_2$O | 3,4-(CH$_2$)$_4$C$_6$H$_3$ | O | H | CH$_2$CH$_2$ | CH$_3$O | 4-pentynyl- |

-continued

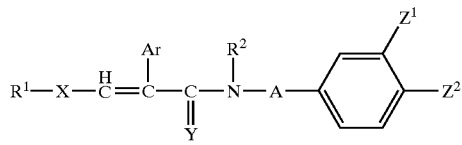

| Nos. | R¹X | Ar | Y | R² | A | Z¹ | Z² |
|---|---|---|---|---|---|---|---|
| 1274 | $CHF_2O$ | $3,4\text{-}(CH_2)_4C_6H_3$ | O | H | $CH_2CH_2$ | $CH_3O$ | oxy<br>$NCCH_2O$ |
| 1275 | $CHF_2O$ | $3,4\text{-}(CH_2)_4C_6H_3$ | O | H | $CH_2CH_2$ | $CH_3O$ | $CH_3S$ |
| 1276 | $CHF_2O$ | $3,4\text{-}(CH_2)_4C_6H_3$ | O | H | $CH_2CH_2$ | $CH_3O$ | $C_2H_5S$ |
| 1277 | $CHF_2O$ | $3,4\text{-}(CH_2)_4C_6H_3$ | O | H | $CH_2CH_2$ | $CH_3O$ | $CH_2FO$ |
| 1278 | $CHF_2O$ | $3,4\text{-}(CH_2)_4C_6H_3$ | O | H | $CH_2CH_2$ | $CH_3O$ | $CHF_2O$ |
| 1279 | $CHF_2O$ | $3,4\text{-}(CH_2)_4C_6H_3$ | O | H | $CH_2CH_2$ | $CH_3O$ | $CF_3O$ |
| 1280 | $CHF_2O$ | $3,4\text{-}(CH_2)_4C_6H_3$ | O | H | $CH_2CH_2$ | $CH_3O$ | $CF_3CH_2O$ |
| 1281 | $CHF_2O$ | $3,4\text{-}(CH_2)_4C_6H_3$ | O | H | $CH_2CH_2$ | $CH_3O$ | $C_6H_4CH_2O$ |
| 1282 | $CHF_2O$ | $3,4\text{-}(CH_2)_4C_6H_3$ | O | H | $CH_2CH_2$ | $CH_3O$ | $CH_3CO_2$ |
| 1283 | $CHF_2O$ | $3,4\text{-}(CH_2)_4C_6H_3$ | O | H | $CH_2CH_2$ | $CH_3O$ | $C_2H_5CO_2$ |
| 1284 | $CHF_2O$ | $3,4\text{-}(CH_2)_4C_6H_3$ | O | H | $CH_2CH_2$ | $CH_3O$ | $CH_3OCH_2O$ |
| 1285 | $CHF_2O$ | $3,4\text{-}(CH_2)_4C_6H_3$ | O | H | $CH_2CH_2$ | $CH_3O$ | ethoxy-<br>methoxy |
| 1286 | $CHF_2O$ | $3,4\text{-}(CH_2)_4C_6H_3$ | O | H | $CH_2CH_2$ | $CH_3O$ | $CH_3NHCO_2$ |
| 1287 | $CHF_2O$ | $3,4\text{-}(CH_2)_4C_6H_3$ | O | H | $CH_2CH_2$ | $CH_3O$ | 3,3-dichloro-<br>allyloxy |
| 1288 | $CHF_2O$ | $3,4\text{-}(CH_2)_4C_6H_3$ | O | H | $CH_2CH_2$ | $CH_3O$ | 3-chloro-2-<br>propynyl |
| 1289 | $CHF_2O$ | $3,4\text{-}(CH_2)_4C_6H_3$ | O | H | $CH_2CH_2$ | $CH_3CH_2CH_2O$ | $CH_3O$ |
| 1290 | $CHF_2O$ | $3,4\text{-}(CH_2)_4C_6H_3$ | O | H | $CH_2CH_2$ | $(CH_3)_2CHO$ | $CH_3O$ |
| 1291 | $CHF_2O$ | $3,4\text{-}(CH_2)_4C_6H_3$ | O | H | $CH_2CH_2$ | cyclopropoxy | $CH_3O$ |
| 1292 | $CHF_2O$ | $3,4\text{-}(CH_2)_4C_6H_3$ | O | H | $CH_2CH_2$ | Cyclopropyl-<br>methoxy | $CH_3O$ |
| 1293 | $CHF_2O$ | $3,4\text{-}(CH_2)_4C_6H_3$ | O | H | $CH_2CH_2$ | butoxy | $CH_3O$ |
| 1294 | $CHF_2O$ | $3,4\text{-}(CH_2)_4C_6H_3$ | O | H | $CH_2CH_2$ | isobutoxy | $CH_3O$ |
| 1295 | $CHF_2O$ | $3,4\text{-}(CH_2)_4C_6H_3$ | O | H | $CH_2CH_2$ | sec-butoxy | $CH_3O$ |
| 1296 | $CHF_2O$ | $3,4\text{-}(CH_2)_4C_6H_3$ | O | H | $CH_2CH_2$ | t-butoxy | $CH_3O$ |
| 1297 | $CHF_2O$ | $3,4\text{-}(CH_2)_4C_6H_3$ | O | H | $CH_2CH_2$ | allyloxy | $CH_3O$ |
| 1298 | $CHF_2O$ | $3,4\text{-}(CH_2)_4C_6H_3$ | O | H | $CH_2CH_2$ | 2-butenyl-<br>oxy | $CH_3O$ |
| 1299 | $CHF_2O$ | $3,4\text{-}(CH_2)_4C_6H_3$ | O | H | $CH_2CH_2$ | $CH\equiv CCH_2O$ | $CH_3O$ |
| 1300 | $CHF_2O$ | $3,4\text{-}(CH_2)_4C_6H_3$ | O | H | $CH_2CH_2$ | 2-butynyl-<br>oxy | $CH_3O$ |
| 1301 | $CHF_2O$ | $3,4\text{-}(CH_2)_4C_6H_3$ | O | H | $CH_2CH_2$ | 2-pentynyl<br>oxy | $CH_3O$ |
| 1302 | $CHF_2O$ | $3,4\text{-}(CH_2)_4C_6H_3$ | O | H | $CH_2CH_2$ | 1-methyl-2-<br>propynyloxy | $CH_3O$ |
| 1303 | $CHF_2O$ | $3,4(CH_2)_4C_6H_3$ | O | H | $CH_2CH_2$ | 3-butynyl-<br>oxy | $CH_3O$ |
| 1304 | $CHF_2O$ | $3,4(CH_2)_4C_6H_3$ | O | H | $CH_2CH_2$ | 4-pentynyl<br>oxy | $CH_3O$ |
| 1305 | $CHF_2O$ | $3,4\text{-}(CH_2)_4C_6H_3$ | O | H | $CH_2CH_2$ | $NCCH_2O$ | $CH_3O$ |
| 1306 | $CHF_2O$ | $3,4\text{-}(CH_2)_4C_6H_3$ | O | H | $CH_2CH_2$ | $CH_3S$ | $CH_3O$ |
| 1307 | $CHF_2O$ | $3,4\text{-}(CH_2)_4C_6H_3$ | O | H | $CH_2CH_2$ | $C_2H_5S$ | $CH_3O$ |
| 1308 | $CHF_2O$ | $3,4\text{-}(CH_2)_4C_6H_3$ | O | H | $CH_2CH_2$ | $CH_2FO$ | $CH_3O$ |
| 1309 | $CHF_2O$ | $3,4\text{-}(CH_2)_4C_6H_3$ | O | H | $CH_2CH_2$ | $CHF_2O$ | $CH_3O$ |
| 1310 | $CHF_2O$ | $3,4\text{-}(CH_2)_4C_6H_3$ | O | H | $CH_2CH_2$ | $CF_3O$ | $CH_3O$ |
| 1311 | $CHF_2O$ | $3,4\text{-}(CH_2)_4C_6H_3$ | O | H | $CH_2CH_2$ | $CF_3CH_2O$ | $CH_3O$ |
| 1312 | $CHF_2O$ | $3,4\text{-}(CH_2)_4C_6H_3$ | O | H | $CH_2CH_2$ | OH | $CH_3O$ |
| 1313 | $CHF_2O$ | $3,4\text{-}(CH_2)_4C_6H_3$ | O | H | $CH_2CH_2$ | $CH_3CO_2$ | $CH_3O$ |
| 1314 | $CHF_2O$ | $3,4\text{-}(CH_2)_4C_6H_3$ | O | H | $CH_2CH_2$ | $C_2H_5CO_2$ | $CH_3O$ |
| 1315 | $CHF_2O$ | $3,4\text{-}(CH_2)_4C_6H_3$ | O | H | $CH_2CH_2$ | $CH_3OCH_2O$ | $CH_3O$ |
| 1316 | $CHF_2O$ | $3,4\text{-}(CH_2)_4C_6H_3$ | O | H | $CH_2CH_2$ | ethoxy-<br>methoxy | $CH_3O$ |
| 1317 | $CHF_2O$ | $3,4\text{-}(CH_2)_4C_6H_3$ | O | H | $CH_2CH_2$ | $CH_3NHCO_2$ | $CH_3O$ |
| 1318 | $CHF_2O$ | $3,4\text{-}(CH_2)_4C_6H_3$ | O | H | $CH_2CH_2$ | 3,3-dichloro<br>allyloxy | $CH_3O$ |
| 1319 | $CHF_2O$ | $3,4\text{-}(CH_2)_4C_6H_3$ | O | H | $CH_2CH_2$ | 3-chloro-2-<br>propynyl | $CH_3O$ |
| 1320 | $CHF_2O$ | $3,4\text{-}(CH_2)_4C_6H_3$ | O | H | $CH_2CH_2$ | $C_2H_5O$ | $CH_3O$ |
| 1321 | $CHF_2O$ | $3,4\text{-}(CH_2)_4C_6H_3$ | O | H | $CH_2CH_2$ | $C_2H_5O$ | $C_2H_5O$ |
| 1322 | $CHF_2O$ | $3,4\text{-}(CH_2)_4C_6H_3$ | O | H | $CH_2CH_2$ | $C_2H_5O$ | $CH_3CH_3CH_3O$ |
| 1323 | $CHF_2O$ | $3,4\text{-}(CH_2)_4C_6H_3$ | O | H | $CH_2CH_2$ | $C_2H_5O$ | butoxy |
| 1324 | $CHF_2O$ | $3,4\text{-}(CH_2)_4C_6H_3$ | O | H | $CH_2CH_2$ | $C_2H_5O$ | allyloxy |
| 1325 | $CHF_2O$ | $3,4\text{-}(CH_2)_4C_6H_3$ | O | H | $CH_2CH_2$ | $C_2H_5O$ | $CH\equiv CCH_2O$ |
| 1326 | $CHF_2O$ | $3,4\text{-}(CH_2)_4C_6H_3$ | O | H | $CH_2CH_2$ | $C_2H_5O$ | 2-butynyl<br>oxy |
| 1327 | $CHF_2O$ | $3,4\text{-}(CH_2)_4C_6H_3$ | O | H | $CH_2CH_2$ | $C_2H_5O$ | 3-butynyl |

-continued

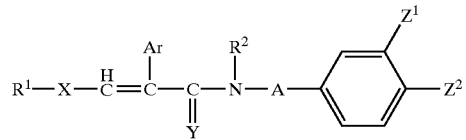

| Nos. | R¹X | Ar | Y | R² | A | Z¹ | Z² |
|---|---|---|---|---|---|---|---|
| 1328 | CHF$_2$O | 3,4-(CH$_2$)$_4$C$_6$H$_3$ | O | H | CH$_2$CH$_2$ | C$_2$H$_5$O | NCCH$_2$O |
| 1329 | CHF$_2$O | 3,4-(CH$_2$)$_4$C$_6$H$_3$ | O | H | CH$_2$CH$_2$ | C$_2$H$_5$O | CH$_3$S |
| 1330 | CHF$_2$O | 3,4-(CH$_2$)$_4$C$_6$H$_3$ | O | H | CH$_2$CH$_2$ | C$_2$H$_5$O | CF$_3$O |
| 1331 | CHF$_2$O | 3,4-(CH$_2$)$_4$C$_6$H$_3$ | O | H | CH$_2$CH$_2$ | propoxy | propoxy |
| 1332 | CHF$_2$O | 3,4-(CH$_2$)$_4$C$_6$H$_3$ | O | H | CH$_2$CH$_2$ | propoxy | (CH$_3$)$_2$CHO |
| 1333 | CHF$_2$O | 3,4-(CH$_2$)$_4$C$_6$H$_3$ | O | H | CH$_2$CH$_2$ | propoxy | cyclopropyl methoxy |
| 1334 | CHF$_2$O | 3,4-(CH$_2$)$_4$C$_6$H$_3$ | O | H | CH$_2$CH$_2$ | propoxy | butoxy |
| 1335 | CHF$_2$O | 3,4-(CH$_2$)$_4$C$_6$H$_3$ | O | H | CH$_2$CH$_2$ | propoxy | allyloxy |
| 1336 | CHF$_2$O | 3,4-(CH$_2$)$_4$C$_6$H$_3$ | O | H | CH$_2$CH$_2$ | propoxy | CH≡CCH$_2$O |
| 1337 | CHF$_2$O | 3,4-(CH$_2$)$_4$C$_6$H$_3$ | O | H | CH$_2$CH$_2$ | propoxy | 2-butynyl oxy |
| 1338 | CHF$_2$O | 3,4-(CH$_2$)$_4$C$_6$H$_3$ | O | H | CH$_2$CH$_2$ | propoxy | 3-butynyl oxy |
| 1339 | CHF$_2$O | 3,4-(CH$_2$)$_4$C$_6$H$_3$ | O | H | CH$_2$CH$_2$ | propoxy | NCCH$_2$O |
| 1340 | CHF$_2$O | 3,4-(CH$_2$)$_4$C$_6$H$_3$ | O | H | CH$_2$CH$_2$ | propoxy | CH$_3$S |
| 1341 | CHF$_2$O | 3,4-(CH$_2$)$_4$C$_6$H$_3$ | O | H | CH$_2$CH$_2$ | propoxy | CF$_3$O |
| 1342 | CHF$_2$O | 3,4-(CH$_2$)$_4$C$_6$H$_3$ | O | H | CH$_2$CH$_2$ | propoxy | CCl≡CCH$_2$O |
| 1343 | CHF$_2$O | 3,4-(CH$_2$)$_4$C$_6$H$_3$ | O | H | CH$_2$CH$_2$ | (CH$_3$)$_2$CHO | CH≡CCH$_2$O |
| 1344 | CHF$_2$O | 3,4-(CH$_2$)$_4$C$_6$H$_3$ | O | H | CH$_2$CH$_2$ | cyclopropyl-methoxy | CH≡CCH$_2$O |
| 1345 | CHF$_2$O | 3,4-(CH$_2$)$_4$C$_6$H$_3$ | O | H | CH$_2$CH$_2$ | butoxy | CH≡CCH$_2$O |
| 1346 | CHF$_2$O | 3,4-(CH$_2$)$_4$C$_6$H$_3$ | O | H | CH$_2$CH$_2$ | allyloxy | CH≡CCH$_2$O |
| 1347 | CHF$_2$O | 3,4-(CH$_2$)$_4$C$_6$H$_3$ | O | H | CH$_2$CH$_2$ | CH≡CCH$_2$O | CH≡CCH$_2$O |
| 1348 | CHF$_2$O | 3,4-(CH$_2$)$_4$C$_6$H$_3$ | O | H | CH$_2$CH$_2$ | 2-butynyl oxy | CH≡CCH$_2$O |
| 1349 | CHF$_2$O | 3,4-(CH$_2$)$_4$C$_6$H$_3$ | O | H | CH$_2$CH$_2$ | 3-butynyl oxy | CH≡CCH$_2$O |
| 1350 | CHF$_2$O | 3,4-(CH$_2$)$_4$C$_6$H$_3$ | O | H | CH$_2$CH$_2$ | NCCH$_2$O | CH≡CCH$_2$O |
| 1351 | CHF$_2$O | 3,4-(CH$_2$)$_4$C$_6$H$_3$ | O | H | CH$_2$CH$_2$ | CH$_3$S | CH≡CCH$_2$O |
| 1352 | CHF$_2$O | 3,4-(CH$_2$)$_4$C$_6$H$_3$ | O | H | CH$_2$CH$_2$ | CF$_3$O | CH≡CCH$_2$O |
| 1353 | CHF$_2$O | 4-CH$_3$C$_6$H$_4$ | O | H | CH$_2$CH$_2$ | CH$_3$O | CH≡CCH$_2$O |
| 1354 | CHF$_2$O | 4-C$_2$H$_5$C$_6$H$_4$ | O | H | CH$_2$CH$_2$ | CH$_3$O | CH≡CCH$_2$O |
| 1355 | CHF$_2$O | 4-ClC$_6$H$_4$ | O | H | CH$_2$CH$_2$ | CH$_3$O | CH≡CCH$_2$O |
| 1356 | CHF$_2$O | 4-BrC$_6$H$_4$ | O | H | CH$_2$CH$_2$ | CH$_3$O | CH≡CCH$_2$O |
| 1357 | CHF$_2$O | 4-CF$_3$C$_6$H$_4$ | O | H | CH$_2$CH$_2$ | CH$_3$O | CH≡CCH$_2$O |
| 1358 | CHF$_2$O | 4-CH$_3$OC$_6$H$_4$ | O | H | CH$_2$CH$_2$ | CH$_3$O | CH≡CCH$_2$O |
| 1359 | CHF$_2$O | 4-CF$_3$OC$_6$H$_4$ | O | H | CH$_2$CH$_2$ | CH$_3$O | CH≡CCH$_2$O |
| 1360 | CHF$_2$O | 3,4-(CH$_2$)$_3$C$_6$H$_3$ | O | H | CH$_2$CH$_2$ | CH$_3$O | CH≡CCH$_2$O |
| 1361 | CHF$_2$O | 3,4-(CH$_2$)$_4$C$_6$H$_3$ | O | H | CH$_2$CH$_2$ | CH$_3$O | CH≡CCH$_2$O |
| 1362 | CH$_2$FO | 4-CH$_3$C$_6$H$_4$ | O | H | CH$_2$CH$_2$ | CH$_3$O | CH≡CCH$_2$O |
| 1363 | CF$_3$O | 4-CH$_3$C$_6$H$_4$ | O | H | CH$_2$CH$_2$ | CH$_3$O | CH≡CCH$_2$O |
| 1364 | CH≡CCH$_2$O | 4-CH$_3$C$_6$H$_4$ | O | H | CH$_2$CH$_2$ | CH$_3$O | CH≡CCH$_2$O |
| 1365 | CH$_2$FO | 4-ClC$_6$H$_4$ | O | H | CH$_2$CH$_2$ | CH$_3$O | CH≡CCH$_2$O |
| 1366 | CF$_3$O | 4-ClC$_6$H$_4$ | O | H | CH$_2$CH$_2$ | CH$_3$O | CH≡CCH$_2$O |
| 1367 | CH≡CCH$_2$O | 4-ClC$_6$H$_4$ | O | H | CH$_2$CH$_2$ | CH$_3$O | CH≡CCH$_2$O |
| 1368 | CH$_2$FO | 3,4-(CH$_2$)$_4$C$_6$H$_3$ | O | H | CH$_2$CH$_2$ | CH$_3$O | CH≡CCH$_2$O |
| 1369 | CF$_3$O | 3,4-(CH$_2$)$_4$C$_6$H$_3$ | O | H | CH$_2$CH$_2$ | CH$_3$O | CH≡CCH$_2$O |
| 1370 | CH≡CCH$_2$O | 3,4-(CH$_2$)$_4$C$_6$H$_3$ | O | H | CH$_2$CH$_2$ | CH$_3$O | CH≡CCH$_2$O |
| 1371 | CHF$_2$O | 3,4-(CH$_2$)$_4$C$_6$H$_3$ | O | H | CH$_2$CH$_2$ | CH$_3$O | OH |
| 1372 | CH$_2$FO | 4-C$_2$H$_5$C$_6$H$_4$ | O | H | CH$_2$CH$_2$ | CH$_3$O | CH≡CCH$_2$O |
| 1373 | CF$_3$O | 4-C$_2$H$_5$C$_6$H$_4$ | O | H | CH$_2$CH$_2$ | CH$_3$O | CH≡CCH$_2$O |
| 1374 | CH≡CCH$_2$O | 4-C$_2$H$_5$C$_6$H$_4$ | O | H | CH$_2$CH$_2$ | CH$_3$O | CH≡CCH$_2$O |
| 1375 | CH$_2$FO | 4-BrC$_6$H$_4$ | O | H | CH$_2$CH$_2$ | CH$_3$O | CH≡CCH$_2$O |
| 1376 | CF$_3$O | 4-BrC$_6$H$_4$ | O | H | CH$_2$CH$_2$ | CH$_3$O | CH≡CCH$_2$O |
| 1377 | CH≡CCH$_2$O | 4-BrC$_6$H$_4$ | O | H | CH$_2$CH$_2$ | CH$_3$O | CH≡CCH$_2$O |
| 1378 | CH$_2$FO | 4-CF$_3$C$_6$H$_4$ | O | H | CH$_2$CH$_2$ | CH$_3$O | CH≡CCH$_2$O |
| 1379 | CF$_3$O | 4-CF$_3$C$_6$H$_4$ | O | H | CH$_2$CH$_2$ | CH$_3$O | CH≡CCH$_2$O |
| 1380 | CH≡CCH$_2$O | 4-CF$_3$C$_6$H$_4$ | O | H | CH$_2$CH$_2$ | CH$_3$O | CH≡CCH$_2$O |
| 1381 | CH$_2$FO | 4-CH$_3$OC$_6$H$_4$ | O | H | CH$_2$CH$_2$ | CH$_3$O | CH≡CCH$_2$O |
| 1382 | CF$_3$O | 4-CH$_3$OC$_6$H$_4$ | O | H | CH$_2$CH$_2$ | CH$_3$O | CH≡CCH$_2$O |
| 1383 | CH≡CCH$_2$O | 4-CH$_3$OC$_6$H$_4$ | O | H | CH$_2$CH$_2$ | CH$_3$O | CH≡CCH$_2$O |
| 1384 | CH$_2$FO | 4-CF$_3$OC$_6$H$_4$ | O | H | CH$_2$CH$_2$ | CH$_3$O | CH≡CCH$_2$O |
| 1385 | CF$_3$O | 4-CF$_3$OC$_6$H$_4$ | O | H | CH$_2$CH$_2$ | CH$_3$O | CH≡CCH$_2$O |
| 1386 | CH≡CCH$_2$O | 4-CF$_3$OC$_6$H$_4$ | O | H | CH$_2$CH$_2$ | CH$_3$O | CH≡CCH$_2$O |
| 1387 | CH$_2$FO | C$_6$H$_5$ | O | H | CH$_2$CH$_2$ | CH$_3$O | CH≡CCH$_2$O |
| 1388 | CHF$_2$O | C$_6$H$_5$ | O | H | CH$_2$CH$_2$ | CH$_3$O | CH≡CCH$_2$O |
| 1389 | CF$_3$O | C$_6$H$_5$ | O | H | CH$_2$CH$_2$ | CH$_3$O | CH≡CCH$_2$O |

-continued

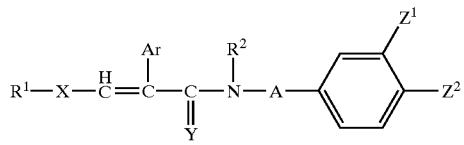

| Nos. | R¹X | Ar | Y | R² | A | Z¹ | Z² |
|---|---|---|---|---|---|---|---|
| 1390 | CH≡CCH₂O | C₆H₅ | O | H | CH₂CH₂ | CH₃O | CH≡CCH₂O |
| 1391 | CH₂FO | 4-FC₆H₄ | O | H | CH₂CH₂ | CH₃O | CH≡CCH₂O |
| 1392 | CHF₂O | 4-FC₆H₄ | O | H | CH₂CH₂ | CH₃O | CH≡CCH₂O |
| 1393 | CF₃O | 4-FC₆H₄ | O | H | CH₂CH₂ | CH₃O | CH≡CCH₂O |
| 1394 | CH≡CCH₂O | 4-FC₆H₄ | O | H | CH₂CH₂ | CH₃O | CH≡CCH₂O |
| 1395 | CH₂FO | 4-CH₃CH₂CH₂C₆H₄ | O | H | CH₂CH₂ | CH₃O | CH≡CCH₂O |
| 1396 | CHF₂O | 4-CH₃CH₂CH₂C₆H₄ | O | H | CH₂CH₂ | CH₃O | CH≡CCH₂O |
| 1397 | CF₃O | 4-CH₃CH₂CH₂C₆H₄ | O | H | CH₂CH₂ | CH₃O | CH≡CCH₂O |
| 1398 | CH≡CCH₂O | 4-CH₃CH₂CH₂C₆H₄ | O | H | CH₂CH₂ | CH₃O | CH≡CCH₂O |
| 1399 | CH₂FO | 4-(CH₃)₂CHC₆H₄ | O | H | CH₂CH₂ | CH₃O | CH≡CCH₂O |
| 1400 | CHF₂O | 4-(CH₃)₂CHC₆H₄ | O | H | CH₂CH₂ | CH₃O | CH≡CCH₂O |
| 1401 | CF₃O | 4-(CH₃)₂CHC₆H₄ | O | H | CH₂CH₂ | CH₃O | CH≡CCH₂O |
| 1402 | CH≡CCH₂O | 4-(CH₃)₂CHC₆H₄ | O | H | CH₂CH₂ | CH₃O | CH≡CCH₂O |
| 1403 | CH₂FO | 4-cyclopropylphenyl | O | H | CH₂CH₂ | CH₃O | CH≡CCH₂O |
| 1404 | CHF₂O | 4-cyclopropylphenyl | O | H | CH₂CH₂ | CH₃O | CH≡CCH₂O |
| 1405 | CF₃O | 4-cyclopropylphenyl | O | H | CH₂CH₂ | CH₃O | CH≡CCH₂O |
| 1406 | CH≡CCH₂O | 4-cyclopropylphenyl | O | H | CH₂CH₂ | CH₃O | CH≡CCH₂O |
| 1407 | CH₂FO | 4-(CH₃)₃CC₆H₄ | O | H | CH₂CH₂ | CH₃O | CH≡CCH₂O |
| 1408 | CHF₂O | 4-(CH₃)₃CC₆H₄ | O | H | CH₂CH₂ | CH₃O | CH≡CCH₂O |
| 1409 | CF₃O | 4-(CH₃)₃CC₆H₄ | O | H | CH₂CH₂ | CH₃O | CH≡CCH₂O |
| 1410 | CH≡CCH₂O | 4-(CH₃)₃CC₆H₄ | O | H | CH₂CH₂ | CH₃O | CH≡CCH₂O |
| 1411 | CH₂FO | 4-CH₃SC₆H₄ | O | H | CH₂CH₂ | CH₃O | CH≡CCH₂O |
| 1412 | CHF₂O | 4-CH₃SC₆H₄ | O | H | CH₂CH₂ | CH₃O | CH≡CCH₂O |
| 1413 | CF₃O | 4-CH₃SC₆H₄ | O | H | CH₂CH₂ | CH₃O | CH≡CCH₂O |
| 1414 | CH≡CCH₂O | 4-CH₃SC₆H₄ | O | H | CH₂CH₂ | CH₃O | CH≡CCH₂O |
| 1415 | CH₂FO | 4-CH≡CC₆H₄ | O | H | CH₂CH₂ | CH₃O | CH≡CCH₂O |
| 1416 | CHF₂O | 4-CH≡CC₆H₄ | O | H | CH₂CH₂ | CH₃O | CH≡CCH₂O |
| 1417 | CF₃O | 4-CH≡CC₆H₄ | O | H | CH₂CH₂ | CH₃O | CH≡CCH₂O |
| 1418 | CH≡CCH₂O | 4-CH≡CC₆H₄ | O | H | CH₂CH₂ | CH₃O | CH≡CCH₂O |
| 1419 | CH₂FO | 4-N≡CC₆H₄ | O | H | CH₂CH₂ | CH₃O | CH≡CCH₂O |
| 1420 | CHF₂O | 4-N≡CC₆H₄ | O | H | CH₂CH₂ | CH₃O | CH≡CCH₂O |
| 1421 | CF₃O | 4-N≡CC₆H₄ | O | H | CH₂CH₂ | CH₃O | CH≡CCH₂O |
| 1422 | CH≡CCH₂O | 4-N≡CC₆H₄ | O | H | CH₂CH₂ | CH₃O | CH≡CCH₂O |
| 1423 | CH₂FO | 4-CH₂=CHC₆H₄ | O | H | CH₂CH₂ | CH₃O | CH≡CCH₂O |
| 1424 | CHF₂O | 4-CH₂=CHC₆H₄ | O | H | CH₂CH₂ | CH₃O | CH≡CCH₂O |
| 1425 | CF₃O | 4-CH₂=CHC₆H₄ | O | H | CH₂CH₂ | CH₃O | CH≡CCH₂O |
| 1426 | CH≡CCH₂O | 4-CH₂=CHC₆H₄ | O | H | CH₂CH₂ | CH₃O | CH≡CCH₂O |
| 1427 | CHF₂O | 3,4-F₂C₆H₃ | O | H | CH₂CH₂ | CH₃O | CH≡CCH₂O |
| 1428 | CH≡CCH₂O | 3,4-F₂C₆H₃ | O | H | CH₂CH₂ | CH₃O | CH≡CCH₂O |
| 1429 | CHF₂O | 3,4-Cl₂C₆H₃ | O | H | CH₂CH₂ | CH₃O | CH≡CCH₂O |
| 1430 | CH≡CCH₂O | 3,4-Cl₂C₆H₃ | O | H | CH₂CH₂ | CH₃O | CH≡CCH₂O |
| 1431 | CHF₂O | 3,4-(CH₃)₂C₆H₃ | O | H | CH₂CH₂ | CH₃O | CH≡CCH₂O |
| 1432 | CH≡CCH₂O | 3,4-(CH₃)₂C₆H₃ | O | H | CH₂CH₂ | CH₃O | CH≡CCH₂O |
| 1433 | CHF₂O | 3-F-4-CH₃C₆H₃ | O | H | CH₂CH₂ | CH₃O | CH≡CCH₂O |
| 1434 | CH≡CCH₂O | 3-F-4-CH₃C₆H₃ | O | H | CH₂CH₂ | CH₃O | CH≡CCH₂O |
| 1435 | CHF₂O | 3-Cl-4-CH₃C₆H₃ | O | H | CH₂CH₂ | CH₃O | CH≡CCH₂O |
| 1436 | CH≡CCH₂O | 3-Cl-4-CH₃C₆H₃ | O | H | CH₂CH₂ | CH₃O | CH≡CCH₂O |
| 1437 | CHF₂O | 4-Cl-3-FC₆H₃ | O | H | CH₂CH₂ | CH₃O | CH≡CCH₂O |
| 1438 | CH≡CCH₂O | 4-Cl-3-FC₆H₃ | O | H | CH₂CH₂ | CH₃O | CH≡CCH₂O |
| 1439 | CHF₂O | 3,4-Cl₂C₆H₃ | O | H | CH₂CH₂ | CH₃O | CH≡CCH₂O |
| 1440 | CH≡CCH₂O | 3,4-Cl₂C₆H₃ | O | H | CH₂CH₂ | CH₃O | CH≡CCH₂O |
| 1441 | CHF₂O | 3-Cl-4-CH₃C₆H₃ | O | H | CH(CH₃)CH₂ | CH₃O | CH≡CCH₂O |
| 1442 | CH≡CCH₂O | 3-Cl-4-CH₃C₆H₃ | O | H | CH(CH₃)CH₂ | CH₃O | CH≡CCH₂O |
| 1443 | CHF₂O | 3,4-Cl₂C₆H₃ | O | H | CH(CH₃)CH₂ | CH₃O | CH≡CCH₂O |
| 1444 | CH≡CCH₂O | 3,4-Cl₂C₆H₃ | O | H | CH(CH₃)CH₂ | CH₃O | CH≡CCH₂O |
| 1445 | CHF₂O | 4-CH₃C₆H₄ | S | H | CH₂CH₂ | CH₃O | CH≡CCH₂O |
| 1446 | CHF₂O | 4-ClC₆H₄ | S | H | CH₂CH₂ | CH₃O | CH≡CCH₂O |
| 1447 | CHF₂O | 3,4-(CH₂)₄C₆H₃ | O | H | CH₂CH₂ | Cl | CH₃O |
| 1448 | CHF₂O | 3,4-(CH₂)₄C₆H₃ | O | H | CH₂CH₂ | CH₃ | CH₃O |
| 1449 | CHF₂O | 3,4-(CH₂)₄C₆H₃ | O | H | CH₂CH₂ | CH₃CH₂ | CH₃O |
| 1450 | CHF₂O | 3,4-(CH₂)₄C₆H₃ | O | H | CH₂CH₂ | OCH₂CH₂O | |
| 1451 | CHF₂O | 4-CH₃C₆H₄ | O | H | CH₂CH₂ | CH₃O | C₆H₅CH₂O |
| 1452 | CHF₂O | 4-CH₃C₆H₄ | O | H | CH₂CH₂ | CH₃O | OH |
| 1453 | CHF₂O | 4-ClC₆H₄ | O | H | CH₂CH₂ | CH₃O | C₆H₅CH₂O |
| 1454 | CHF₂O | 4-ClC₆H₄ | O | H | CH₂CH₂ | CH₃O | OH |
| 1455 | CH≡CCH₂O | 4-CH₃C₆H₄ | O | H | CH₂CH₂ | CH₃O | C₆H₅CH₂O |
| 1456 | CH≡CCH₂O | 4-CH₃C₆H₄ | O | H | CH₂CH₂ | CH₃O | OH |
| 1457 | CH≡CCH₂O | 4-ClC₆H₄ | O | H | CH₂CH₂ | CH₃O | C₆H₅CH₂O |
| 1458 | CH≡CCH₂O | 4-ClC₆H₄ | O | H | CH₂CH₂ | CH₃O | OH |

-continued

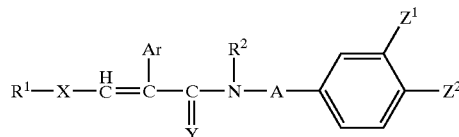

| Nos. | R¹X | Ar | Y | R² | A | Z¹ | Z² |
|---|---|---|---|---|---|---|---|
| 1459 | CHF₂O | 4-CH₃C₆H₄ | O | CH₃ | CH₂CH₂ | CH₃O | CH≡CCH₂O |
| 1460 | CHF₂O | 4-CH₃C₆H₄ | O | ethyl | CH₂CH₂ | CH₃O | CH≡CCH₂O |
| 1461 | CHF₂O | 4-CH₃C₆H₄ | O | propyl | CH₂CH₂ | CH₃O | CH≡CCH₂O |
| 1462 | CHF₂O | 4-ClC₆H₄ | O | CH₃ | CH₂CH₂ | CH₃O | CH≡CCH₂O |
| 1463 | CHF₂O | 3,4-(CH₂)₄C₆H₃ | O | CH₃ | CH₂CH₂ | CH₃O | CH≡CCH₂O |
| 1464 | CHF₂O | 3,4-(CH₂)₄C₆H₃ | O | H | CH(CH₃)CH₂ | CH₃O | CH₃O |
| 1465 | CHF₂O | 4-CH₃C₆H₄ | O | H | CH(CH₃)CH₂ | CH₃O | CH≡CCH₂O |
| 1466 | CHF₂O | 4-ClC₆H₄ | O | H | CH(CH₃)CH₂ | CH₃O | CH≡CCH₂O |
| 1467 | CHF₂O | 3,4-(CH₂)₄C₆H₃ | O | H | CH₂CH(CH₃) | CH₃O | CH₃O |
| 1468 | CHF₂O | 4-CH₃C₆H₄ | O | H | CH₂CH(CH₃) | CH₃O | CH≡CCH₂O |
| 1469 | CHF₂O | 4-ClC₆H₄ | O | H | CH₂CH(CH₃) | CH₃O | CH≡CCH₂O |
| 1470 | CHF₂O | 4-CH₃C₆H₄ | O | H | CH₂CHF | CH₃O | CH≡CCH₂O |
| 1471 | CHF₂O | 4-CH₃C₆H₄ | O | H | CH₂CHCl | CH₃O | CH≡CCH₂O |
| 1472 | CHF₂O | 4-CH₃C₆H₄ | O | H | CH₂CH(OCH₃) | CH₃O | CH≡CCH₂O |
| 1473 | CHF₂O | 4-CH₃C₆H₄ | O | H | CH₂CH(CN) | CH₃O | CH≡CCH₂O |
| 1474 | CHF₂O | 4-CH₃C₆H₄ | O | H | CH(CN)CH₂ | CH₃O | CH≡CCH₂O |
| 1475 | CHF₂O | 3,4-(CH₂)₄C₆H₃ | O | H | CH₂CH₂CH₂ | CH₃O | CH₃O |
| 1476 | CHF₂O | 4-CH₃C₆H₄ | O | H | CH₂CH₂CH₂ | CH₃O | CH₃O |
| 1477 | CHF₂O | 4-CH₃C₆H₄ | O | H | CH₂CH₂CH₂ | CH₃O | CH≡CCH₂O |
| 1478 | CHF₂O | 4-ClC₆H₄ | O | H | CH₂CH₂CH₂ | CH₃O | CH≡CCH₂O |
| 2001 | CH₂FO | 2-thienyl | O | H | CH₂CH₂ | CH₃O | CH₃O |
| 2002 | CHF₂O | 2-thienyl | O | H | CH₂CH₂ | CH₃O | CH₃O |
| 2003 | CF₃O | 2-thienyl | O | H | CH₂CH₂ | CH₃O | CH₃O |
| 2004 | CH₂FO | 3-thienyl | O | H | CH₂CH₂ | CH₃O | CH₃O |
| 2005 | CHF₂O | 3-thienyl | O | H | CH₂CH₂ | CH₃O | CH₃O |
| 2006 | CF₃O | 3-thienyl | O | H | CH₂CH₂ | CH₃O | CH₃O |
| 2007 | CH₂FO | 2-(4-methylthienyl) | O | H | CH₂CH₂ | CH₃O | CH₃O |
| 2008 | CHF₂O | 2-(4-methylthienyl) | O | H | CH₂CH₂ | CH₃O | CH₃O |
| 2009 | CF₃O | 2-(4-methylthienyl) | O | H | CH₂CH₂ | CH₃O | CH₃O |
| 2010 | CH₂FO | 2-(5-methylthienyl) | O | H | CH₂CH₂ | CH₃O | CH₃O |
| 2011 | CHF₂O | 2-(5-methylthienyl) | O | H | CH₂CH₂ | CH₃O | CH₃O |
| 2012 | CF₃O | 2-(5-methylthienyl) | O | H | CH₂CH₂ | CH₃O | CH₃O |
| 2013 | CH₂FO | 2-(4-chlorothienyl) | O | H | CH₂CH₂ | CH₃O | CH₃O |
| 2014 | CHF₂O | 2-(4-chlorothienyl) | O | H | CH₂CH₂ | CH₃O | CH₃O |
| 2015 | CF₃O | 2-(4-chlorothienyl) | O | H | CH₂CH₂ | CH₃O | CH₃O |
| 2016 | CH₂FO | 2-(5-trifluoromethyl thienyl) | O | H | CH₂CH₂ | CH₃O | CH₃O |
| 2017 | CHF₂O | 2-(5-trifluoromethyl thienyl) | O | H | CH₂CH₂ | CH₃O | CH₃O |
| 2018 | CF₃O | 2-(5-trifluoromethyl thienyl) | O | H | CH₂CH₂ | CH₃O | CH₃O |
| 2019 | CH₂FO | 2-furyl | O | H | CH₂CH₂ | CH₃O | CH₃O |
| 2020 | CHF₂O | 2-furyl | O | H | CH₂CH₂ | CH₃O | CH₃O |
| 2021 | CF₃O | 2-furyl | O | H | CH₂CH₂ | CH₃O | CH₃O |
| 2022 | CH₂FO | 3-furyl | O | H | CH₂CH₂ | CH₃O | CH₃O |
| 2023 | CHF₂O | 3-furyl | O | H | CH₂CH₂ | CH₃O | CH₃O |
| 2024 | CF₃O | 3-furyl | O | H | CH₂CH₂ | CH₃O | CH₃O |
| 2025 | CH₂FO | 2-(5-methyfuryl) | O | H | CH₂CH₂ | CH₃O | CH₃O |
| 2026 | CHF₂O | 2-(5-methyfuryl) | O | H | CH₂CH₂ | CH₃O | CH₃O |
| 2027 | CF₃O | 2-(5-methyfuryl) | O | H | CH₂CH₂ | CH₃O | CH₃O |
| 2028 | CH₂FO | 2-pyridyl | O | H | CH₂CH₂ | CH₃O | CH₃O |
| 2029 | CHF₂O | 2-pyridyl | O | H | CH₂CH₂ | CH₃O | CH₃O |
| 2030 | CF₃O | 2-pyridyl | O | H | CH₂CH₂ | CH₃O | CH₃O |
| 2031 | CH₂FO | 2-(5-methylpyridyl) | O | H | CH₂CH₂ | CH₃O | CH₃O |
| 2032 | CHF₂O | 2-(5-methylpyridyl) | O | H | CH₂CH₂ | CH₃O | CH₃O |
| 2033 | CF₃O | 2-(5-methylpyridyl) | O | H | CH₂CH₂ | CH₃O | CH₃O |
| 2034 | CH₂FO | 2-(5-trifluoromethyl pyridyl) | O | H | CH₂CH₂ | CH₃O | CH₃O |
| 2035 | CHF₂O | 2-(5-trifluoromethyl pyridyl) | O | H | CH₂CH₂ | CH₃O | CH₃O |
| 2036 | CF₃O | 2-(5-trifluoromethyl pyridyl) | O | H | CH₂CH₂ | CH₃O | CH₃O |
| 2037 | CH₂FO | 2-pyrimidinyl | O | H | CH₂CH₂ | CH₃O | CH₃O |
| 2038 | CHF₂O | 2-pyrimidinyl | O | H | CH₂CH₂ | CH₃O | CH₃O |
| 2039 | CF₃O | 2-pyrimidinyl | O | H | CH₂CH₂ | CH₃O | CH₃O |
| 2040 | CH₂FO | 4-pyrimidinyl | O | H | CH₂CH₂ | CH₃O | CH₃O |
| 2041 | CHF₂O | 4-pyrimidinyl | O | H | CH₂CH₂ | CH₃O | CH₃O |
| 2042 | CF₃O | 4-pyrimidinyl | O | H | CH₂CH₂ | CH₃O | CH₃O |
| 2043 | CH₂FO | 2-pyrazinyl | O | H | CH₂CH₂ | CH₃O | CH₃O |

-continued

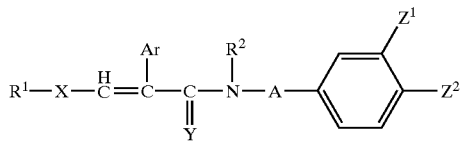

| Nos. | R¹X | Ar | Y | R² | A | Z¹ | Z² |
|---|---|---|---|---|---|---|---|
| 2044 | CH₂FO | 2-pyrazinyl | O | H | CH₂CH₂ | CH₃O | CH₃O |
| 2045 | CF₃O | 2-pyrazinyl | O | H | CH₂CH₂ | CH₃O | CH₃O |
| 2046 | CH₂FO | 2-thiazolyl | O | H | CH₂CH₂ | CH₃O | CH₃O |
| 2047 | CHF₂O | 2-thiazolyl | O | H | CH₂CH₂ | CH₃O | CH₃O |
| 2048 | CF₃O | 2-thiazolyl | O | H | CH₂CH₂ | CH₃O | CH₃O |
| 2049 | CH₂FO | 2-(5-methylthiazolyl) | O | H | CH₂CH₂ | CH₃O | CH₃O |
| 2050 | CHF₂O | 2-(5-methylthiazolyl) | O | H | CH₂CH₂ | CH₃O | CH₃O |
| 2051 | CF₃O | 2-(5-methylthiazolyl) | O | H | CH₂CH₂ | CH₃O | CH₃O |
| 2052 | CH₂FO | 2-(3-methylthiazolyl) | O | H | CH₂CH₂ | CH₃O | CH₃O |
| 2053 | CHF₂O | 2-(3-methylthiazolyl) | O | H | CH₂CH₂ | CH₃O | CH₃O |
| 2054 | CF₃O | 2-(3-methylthiazolyl) | O | H | CH₂CH₂ | CH₃O | CH₃O |
| 2055 | CH₂FO | 1-(4-methylpyrazolyl) | O | H | CH₂CH₂ | CH₃O | CH₃O |
| 2056 | CHF₂O | 1-(4-methylpyrazolyl) | O | H | CH₂CH₂ | CH₃O | CH₃O |
| 2057 | CF₃O | 1-(4-methylpyrazolyl) | O | H | CH₂CH₂ | CH₃O | CH₃O |
| 2058 | CH₂FO | 2-thienyl | O | H | CH₂CH₂ | CH₃CH₂O | CH₃O |
| 2059 | CHF₂O | 2-thienyl | O | H | CH₂CH₂ | CH₃CH₂O | CH₃O |
| 2060 | CF₃O | 2-thienyl | O | H | CH₂CH₂ | CH₃CH₂O | CH₃O |
| 2061 | CH₂FO | 3-thienyl | O | H | CH₂CH₂ | CH₃CH₂O | CH₃O |
| 2062 | CHF₂O | 3-thienyl | O | H | CH₂CH₂ | CH₃CH₂O | CH₃O |
| 2063 | CF₃O | 3-thienyl | O | H | CH₂CH₂ | CH₃CH₂O | CH₃O |
| 2064 | CH₂FO | 2-thienyl | S | H | CH₂CH₂ | CH₃O | CH₃O |
| 2065 | CHF₂O | 2-thienyl | S | H | CH₂CH₂ | CH₃O | CH₃O |
| 2066 | CF₃O | 2-thienyl | S | H | CH₂CH₂ | CH₃O | CH₃O |
| 2067 | CH₂FO | 3-thienyl | S | H | CH₂CH₂ | CH₃O | CH₃O |
| 2068 | CHF₂O | 3-thienyl | S | H | CH₂CH₂ | CH₃O | CH₃O |
| 2069 | CF₃O | 3-thienyl | S | H | CH₂CH₂ | CH₃O | CH₃O |
| 2070 | CH₂FO | 2-(5-methylpyridyl) | O | H | CH₂CH₂ | CH₃CH₂O | CH₃O |
| 2071 | CHF₂O | 2-(5-methylpyridyl) | O | H | CH₂CH₂ | CH₃CH₂O | CH₃O |
| 2072 | CF₃O | 2-(5methylpyridyl) | O | H | CH₂CH₂ | CH₃CH₂O | CH₃O |
| 2073 | CH₂FO | 1-naphthyl | O | H | CH₂CH₂ | CH₃O | CH₃O |
| 2074 | CHF₂O | 1-naphthyl | O | H | CH₂CH₂ | CH₃O | CH₃O |
| 2075 | CF₃O | 1-naphthyl | O | H | CH₂CH₂ | CH₃O | CH₃O |
| 2076 | CH₂FO | 2-naphthyl | O | H | CH₂CH₂ | CH₃O | CH₃O |
| 2077 | CHF₂O | 2-naphthyl | O | H | CH₂CH₂ | CH₃O | CH₃O |
| 2078 | CF₃O | 2-naphthyl | O | H | CH₂CH₂ | CH₃O | CH₃O |
| 2079 | CH₂FO | 2-naplithyl | S | H | CH₂CH₂ | CH₃O | CH₃O |
| 2080 | CHF₂O | 2-naphthyl | S | H | CH₂CH₂ | CH₃O | CH₃O |
| 2081 | CF₃O | 2-naphthyl | S | H | CH₂CH₂ | CH₃O | CH₃O |
| 2082 | CH₂FO | 5-benzofuryl | O | H | CH₂CH₂ | CH₃O | CH₃O |
| 2083 | CHF₂O | 5-benzofuryl | O | H | CH₂CH₂ | CH₃O | CH₃O |
| 2084 | CF₃O | 5-benzofuryl | O | H | CH₂CH₂ | CH₃O | CH₃O |
| 2085 | CH₂FO | 6-benzofuryl | O | H | CH₂CH₂ | CH₃O | CH₃O |
| 2086 | CHF₂O | 6-benzofuryl | O | H | CH₂CH₂ | CH₃O | CH₃O |
| 2087 | CF₃O | 6-benzofuryl | O | H | CH₂CH₂ | CH₃O | CH₃O |
| 2088 | CH₂FO | 5-benzothienyl | O | H | CH₂CH₂ | CH₃O | CH₃O |
| 2089 | CHF₂O | 5-benzothienyl | O | H | CH₂CH₂ | CH₃O | CH₃O |
| 2090 | CF₃O | 5-benzothienyl | O | H | CH₂CH₂ | CH₃O | CH₃O |
| 2091 | CH₂FO | 6-benzothienyl | O | H | CH₂CH₂ | CH₃O | CH₃O |
| 2092 | CHF₂O | 6-benzothienyl | O | H | CH₂CH₂ | CH₃O | CH₃O |
| 2093 | CF₃O | 6-benzothienyl | O | H | CH₂CH₂ | CH₃O | CH₃O |
| 2094 | CH₂FO | 5-benzothiazolyl | O | H | CH₂CH₂ | CH₃O | CH₃O |
| 2095 | CHF₂O | 5-benzothiazolyl | O | H | CH₂CH₂ | CH₃O | CH₃O |
| 2096 | CF₃O | 5-benzothiazolyl | O | H | CH₂CH₂ | CH₃O | CH₃O |
| 2097 | CH₂FO | 6-benzothiazolyl | O | H | CH₂CH₂ | CH₃O | CH₃O |
| 2098 | CHF₂O | 6-benzothiazolyl | O | H | CH₂CH₂ | CH₃O | CH₃O |
| 2099 | CF₃O | 6-benzothiazolyl | O | H | CH₂CH₂ | CH₃O | CH₃O |
| 2100 | CH₂FO | 2-benzothiazolyl | O | H | CH₂CH₂ | CH₃O | CH₃O |
| 2101 | CHF₂O | 2-benzothiazolyl | O | H | CH₂CH₂ | CH₃O | CH₃O |
| 2102 | CF₃O | 2-benzothiazolyl | O | H | CH₂CH₂ | CH₃O | CH₃O |
| 2103 | CH₂FO | 2-benzothienyl | O | H | CH₂CH₂ | CH₃O | CH₃O |
| 2104 | CHF₂O | 2-benzothienyl | O | H | CH₂CH₂ | CH₃O | CH₃O |
| 2105 | CF₃O | 2-benzothienyl | O | H | CH₂CH₂ | CH₃O | CH₃O |
| 2106 | CH₂FO | 2-benzofuryl | O | H | CH₂CH₂ | CH₃O | CH₃O |
| 2107 | CHF₂O | 2-benzofuryl | O | H | CH₂CH₂ | CH₃O | CH₃O |
| 2108 | CF₃O | 2-benzofuryl | O | H | CH₂CH₂ | CH₃O | CH₃O |
| 2109 | CH₂FO | 3-benzofuryl | O | H | CH₂CH₂ | CH₃O | CH₃O |
| 2110 | CHF₂O | 3-benzofuryl | O | H | CH₂CH₂ | CH₃O | CH₃O |
| 2111 | CF₃O | 3-benzofuryl | O | H | CH₂CH₂ | CH₃O | CH₃O |
| 2112 | CH₂FO | benzo-1,2,3-thiazol- | O | H | CH₂CH₂ | CH₃O | CH₃O |

-continued

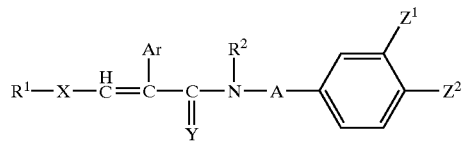

| Nos. | R¹X | Ar | Y | R² | A | Z¹ | Z² |
|---|---|---|---|---|---|---|---|
| 2113 | CHF$_2$O | benzo-1,2,3-thiazol-5-yl | O | H | CH$_2$CH$_2$ | CH$_3$O | CH$_3$O |
| 2114 | CF$_3$O | benzo-1,2,3-thiazol-5-yl | O | H | CH$_2$CH$_2$ | CH$_3$O | CH$_3$O |
| 2115 | CH$_2$FO | 2-benzimidazolyl | O | H | CH$_2$CH$_2$ | CH$_3$O | CH$_3$O |
| 2116 | CHF$_2$O | 2-benzimidazolyl | O | H | CH$_2$CH$_2$ | CH$_3$O | CH$_3$O |
| 2117 | CF$_3$O | 2-benzimidazolyl | O | H | CH$_2$CH$_2$ | CH$_3$O | CH$_3$O |
| 2118 | CH$_2$FO | 2-(1-methylbenzimidazolyl) | O | H | CH$_2$CH$_2$ | CH$_3$O | CH$_3$O |
| 2119 | CHF$_2$O | 2-(1-methylbenzimidazolyl) | O | H | CH$_2$CH$_2$ | CH$_3$O | CH$_3$O |
| 2120 | CF$_3$O | 2-(1-methylbenzimidazolyl) | O | H | CH$_2$CH$_2$ | CH$_3$O | CH$_3$O |
| 2121 | CH≡CCH$_2$O | 2-(5-methylthienyl) | O | H | CH$_2$CH$_2$ | CH$_3$O | CH$_3$O |
| 2122 | CH≡CCH$_2$O | 2-(5-trifluoromethylthienyl) | O | H | CH$_2$CH$_2$ | CH$_3$O | CH$_3$O |
| 2123 | CH≡CCH$_2$O | 2-(5-methylfuryl) | O | H | CH$_2$CH$_2$ | CH$_3$O | CH$_3$O |
| 2124 | CH≡CCH$_2$O | 2-(5-trifluoromethylpyridyl) | O | H | CH$_2$CH$_2$ | CH$_3$O | CH$_3$O |
| 2125 | CH≡CCH$_2$O | 2-naphthyl | O | H | CH$_2$CH$_2$ | CH$_3$O | CH$_3$O |
| 2126 | CH$_2$FO | 2-thienyl | O | H | CH$_2$CH$_2$ | CH$_3$O | CH≡CCH$_2$O |
| 2127 | CHF$_2$O | 2-thienyl | O | H | CH$_2$CH$_2$ | CH$_3$O | CH≡CCH$_2$O |
| 2128 | CF$_3$O | 2-thienyl | O | H | CH$_2$CH$_2$ | CH$_3$O | CH≡CCH$_2$O |
| 2129 | CH$_2$FO | 3-thienyl | O | H | CH$_2$CH$_2$ | CH$_3$O | CH≡CCH$_2$O |
| 2130 | CHF$_2$O | 3-thienyl | O | H | CH$_2$CH$_2$ | CH$_3$O | CH≡CCH$_2$O |
| 2131 | CF$_3$O | 3-thienyl | O | H | CH$_2$CH$_2$ | CH$_3$O | CH≡CCH$_2$O |
| 2132 | CH$_2$FO | 2-(4-methylthienyl) | O | H | CH$_2$CH$_2$ | CH$_3$O | CH≡CCH$_2$O |
| 2133 | CHF$_2$O | 2-(4-methylthienyl) | O | H | CH$_2$CH$_2$ | CH$_3$O | CH≡CCH$_2$O |
| 2134 | CF$_3$O | 2-(4-methylthienyl) | O | H | CH$_2$CH$_2$ | CH$_3$O | CH≡CCH$_2$O |
| 2135 | CH$_2$FO | 2-(5-methylthienyl) | O | H | CH$_2$CH$_2$ | CH$_3$O | CH≡CCH$_2$O |
| 2136 | CHF$_2$O | 2-(5-methylthienyl) | O | H | CH$_2$CH$_2$ | CH$_3$O | CH≡CCH$_2$O |
| 2137 | CF$_3$O | 2-(5-methylthienyl) | O | H | CH$_2$CH$_2$ | CH$_3$O | CH≡CCH$_2$O |
| 2138 | CH$_2$FO | 2-(5-chlorothienyl) | O | H | CH$_2$CH$_2$ | CH$_3$O | CH≡CCH$_2$O |
| 2139 | CHF$_2$O | 2-(5-chlorothienyl) | O | H | CH$_2$CH$_2$ | CH$_3$O | CH≡CCH$_2$O |
| 2140 | CF$_3$O | 2-(5-chlorothienyl) | O | H | CH$_2$CH$_2$ | CH$_3$O | CH≡CCH$_2$O |
| 2141 | CH$_2$FO | 2-(5-trifluoromethyl thienyl) | O | H | CH$_2$CH$_2$ | CH$_3$O | CH≡CCH$_2$O |
| 2142 | CHF$_2$O | 2-(5-trifluoromethyl thienyl) | O | H | CH$_2$CH$_2$ | CH$_3$O | CH≡CCH$_2$O |
| 2143 | CF$_3$O | 2-(5-trifluoromethyl thienyl) | O | H | CH$_2$CH$_2$ | CH$_3$O | CH≡CCH$_2$O |
| 2144 | CH$_2$FO | 2-furyl | O | H | CH$_2$CH$_2$ | CH$_3$O | CH≡CCH$_2$O |
| 2145 | CHF$_2$O | 2-furyl | O | H | CH$_2$CH$_2$ | CH$_3$O | CH≡CCH$_2$O |
| 2146 | CF$_3$O | 2-furyl | O | H | CH$_2$CH$_2$ | CH$_3$O | CH≡CCH$_2$O |
| 2147 | CH$_2$FO | 3-furyl | O | H | CH$_2$CH$_2$ | CH$_3$O | CH≡CCH$_2$O |
| 2148 | CHF$_2$O | 3-furyl | O | H | CH$_2$CH$_2$ | CH$_3$O | CH≡CCH$_2$O |
| 2149 | CF$_3$O | 3-furyl | O | H | CH$_2$CH$_2$ | CH$_3$O | CH≡CCH$_2$O |
| 2150 | CH$_2$FO | 2-(5-methylfuryl) | O | H | CH$_2$CH$_2$ | CH$_3$O | CH≡CCH$_2$O |
| 2151 | CHF$_2$O | 2-(5-methylfuryl) | O | H | CH$_2$CH$_2$ | CH$_3$O | CH≡CCH$_2$O |
| 2152 | CF$_3$O | 2-(5-methylfuryl) | O | H | CH$_2$CH$_2$ | CH$_3$O | CH≡CCH$_2$O |
| 2153 | CH$_2$FO | 2-pyridyl | O | H | CH$_2$CH$_2$ | CH$_3$O | CH≡CCH$_2$O |
| 2154 | CHF$_2$O | 2-pyridyl | O | H | CH$_2$CH$_2$ | CH$_3$O | CH≡CCH$_2$O |
| 2155 | CF$_3$O | 2-pyridyl | O | H | CH$_2$CH$_2$ | CH$_3$O | CH≡CCH$_2$O |
| 2156 | CH$_2$FO | 2-(5-methylpyridyl) | O | H | CH$_2$CH$_2$ | CH$_3$O | CH≡CCH$_2$O |
| 2157 | CHF$_2$O | 2-(5-methylpyridyl) | O | H | CH$_2$CH$_2$ | CH$_3$O | CH≡CCH$_2$O |
| 2158 | CF$_3$O | 2-(5-methylpyridyl) | O | H | CH$_2$CH$_2$ | CH$_3$O | CH≡CCH$_2$O |
| 2159 | CH$_2$FO | 2-(5-trifluoromethyl pyridyl) | O | H | CH$_2$CH$_2$ | CH$_3$O | CH≡CCH$_2$O |
| 2160 | CHF$_2$O | 2-(5-trifluoromethyl pyridyl) | O | H | CH$_2$CH$_2$ | CH$_3$O | CH≡CCH$_2$O |
| 2161 | CF$_3$O | 2-(5-trifluoromethyl pyridyl) | O | H | CH$_2$CH$_2$ | CH$_3$O | CH≡CCH$_2$O |
| 2162 | CH$_2$FO | 2-pyrimidinyl | O | H | CH$_2$CH$_2$ | CH$_3$O | CH≡CCH$_2$O |
| 2163 | CHF$_2$O | 2-pyrimidinyl | O | H | CH$_2$CH$_2$ | CH$_3$O | CH≡CCH$_2$O |
| 2164 | CF$_3$O | 2-pyrimidinyl | O | H | CH$_2$CH$_2$ | CH$_3$O | CH≡CCH$_2$O |
| 2165 | CH$_2$FO | 4-pyrimidinyl | O | H | CH$_2$CH$_2$ | CH$_3$O | CH≡CCH$_2$O |
| 2166 | CHF$_2$O | 4-pyrimidinyl | O | H | CH$_2$CH$_2$ | CH$_3$O | CH≡CCH$_2$O |
| 2167 | CF$_3$O | 4-pyrimidinyl | O | H | CH$_2$CH$_2$ | CH$_3$O | CH≡CCH$_2$O |

-continued

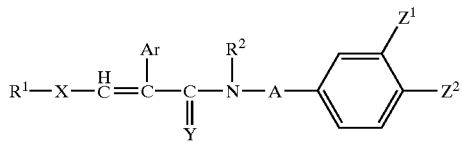

| Nos. | R¹X | Ar | Y | R² | A | Z¹ | Z² |
|---|---|---|---|---|---|---|---|
| 2168 | CH$_2$FO | 2-pyrazinyl | O | H | CH$_2$CH$_2$ | CH$_3$O | CH≡CCH$_2$O |
| 2169 | CHF$_2$O | 2-pyrazinyl | O | H | CH$_2$CH$_2$ | CH$_3$O | CH≡CCH$_2$O |
| 2170 | CF$_3$O | 2-pyrazinyl | O | H | CH$_2$CH$_2$ | CH$_3$O | CH≡CCH$_2$O |
| 2171 | CH$_2$FO | 2-thiazolyl | O | H | CH$_2$CH$_2$ | CH$_3$O | CH≡CCH$_2$O |
| 2172 | CHF$_2$O | 2-thiazolyl | O | H | CH$_2$CH$_2$ | CH$_3$O | CH≡CCH$_2$O |
| 2173 | CF$_3$O | 2-thiazolyl | O | H | CH$_2$CH$_2$ | CH$_3$O | CH≡CCH$_2$O |
| 2174 | CH$_2$FO | 2-(5-methylthiazolyl) | O | H | CH$_2$CH$_2$ | CH$_3$O | CH≡CCH$_2$O |
| 2175 | CHF$_2$O | 2-(5-methylthiazolyl) | O | H | CH$_2$CH$_2$ | CH$_3$O | CH≡CCH$_2$O |
| 2176 | CF$_3$O | 2-(5-methylthiazolyl) | O | H | CH$_2$CH$_2$ | CH$_3$O | CH≡CCH$_2$O |
| 2177 | CH$_2$FO | 3-(3-methylpyrazolyl) | O | H | CH$_2$CH$_2$ | CH$_3$O | CH≡CCH$_2$O |
| 2178 | CHF$_2$O | 3-(3-methylpyrazolyl) | O | H | CH$_2$CH$_2$ | CH$_3$O | CH≡CCH$_2$O |
| 2179 | CF$_3$O | 3-(3-methylpyrazolyl) | O | H | CH$_2$CH$_2$ | CH$_3$O | CH≡CCH$_2$O |
| 2180 | CH$_2$FO | 1-(4-methylpyrazolyl) | O | H | CH$_2$CH$_2$ | CH$_3$O | CH≡CCH$_2$O |
| 2181 | CHF$_2$O | 1-(4-methylpyrazolyl) | O | H | CH$_2$CH$_2$ | CH$_3$O | CH≡CCH$_2$O |
| 2182 | CF$_3$O | 1-(4-methylpyrazolyl) | O | H | CH$_2$CH$_2$ | CH$_3$O | CH≡CCH$_2$O |
| 2183 | CH$_2$FO | 2-thienyl | O | H | CH(CH$_3$)CH$_2$ | CH$_3$O | CH$_3$O |
| 2184 | CHF$_2$O | 2-thienyl | O | H | CH(CH$_3$)CH$_2$ | CH$_3$O | CH$_3$O |
| 2185 | CF$_3$O | 2-thienyl | O | H | CH(CH$_3$)CH$_2$ | CH$_3$O | CH$_3$O |
| 2186 | CH$_2$FO | 3-thienyl | O | H | CH(CH$_3$)CH$_2$ | CH$_3$O | CH$_3$O |
| 2187 | CHF$_2$O | 3-thienyl | O | H | CH(CH$_3$)CH$_2$ | CH$_3$O | CH$_3$O |
| 2188 | CF$_3$O | 3-thienyl | O | H | CH(CH$_3$)CH$_2$ | CH$_3$O | CH$_3$O |
| 2189 | CH$_2$FO | 2-naphthyl | O | H | CH(CH$_3$)CH$_2$ | CH$_3$O | CH$_3$O |
| 2190 | CHF$_2$O | 2-naphthyl | O | H | CH(CH$_3$)CH$_2$ | CH$_3$O | CH$_3$O |
| 2191 | CF$_3$O | 2-naphthyl | O | H | CH(CH$_3$)CH$_2$ | CH$_3$O | CH$_3$O |
| 2192 | CH$_2$FO | 2-naphthyl | O | CH$_3$ | CH$_2$CH$_2$ | CH$_3$O | CH$_3$O |
| 2193 | CHF$_2$O | 2-naphthyl | O | CH$_3$ | CH$_2$CH$_2$ | CH$_3$O | CH$_3$O |
| 2194 | CF$_3$O | 2-naphthyl | O | CH$_3$ | CH$_2$CH$_2$ | CH$_3$O | CH$_3$O |
| 2195 | CH$_2$FO | 2-thienyl | O | CH$_3$ | CH$_2$CH$_2$ | CH$_3$O | CH$_3$O |
| 2196 | CHF$_2$O | 2-thienyl | O | CH$_3$ | CH$_2$CH$_2$ | CH$_3$O | CH$_3$O |
| 2197 | CF$_3$O | 2-thienyl | O | CH$_3$ | CH$_2$CH$_2$ | CH$_3$O | CH$_3$O |
| 2198 | CH$_2$FO | 1-naphthyl | O | H | CH$_2$CH$_2$ | CH$_3$O | CH≡CCH$_2$O |
| 2199 | CHF$_2$O | 1-naphthyl | O | H | CH$_2$CH$_2$ | CH$_3$O | CH≡CCH$_2$O |
| 2200 | CF$_3$O | 1-naphthyl | O | H | CH$_2$CH$_2$ | CH$_3$O | CH≡CCH$_2$O |
| 2201 | CH$_2$FO | 2-naphthyl | O | H | CH$_2$CH$_2$ | CH$_3$O | CH≡CCH$_2$O |
| 2202 | CHF$_2$O | 2-naphthyl | O | H | CH$_2$CH$_2$ | CH$_3$O | CH≡CCH$_2$O |
| 2203 | CF$_3$O | 2-naphthyl | O | H | CH$_2$CH$_2$ | CH$_3$O | CH≡CCH$_2$O |
| 2204 | CH$_2$FO | 2-naphthyl | S | H | CH$_2$CH$_2$ | CH$_3$O | CH≡CCH$_2$O |
| 2205 | CHF$_2$O | 2-naphthyl | S | H | CH$_2$CH$_2$ | CH$_3$O | CH≡CCH$_2$O |
| 2206 | CF$_3$O | 2-naphthyl | S | H | CH$_2$CH$_2$ | CH$_3$O | CH≡CCH$_2$O |
| 2207 | CH$_2$FO | 5-benzofuryl | O | H | CH$_2$CH$_2$ | CH$_3$O | CH≡CCH$_2$O |
| 2208 | CHF$_2$O | 5-benzofuryl | O | H | CH$_2$CH$_2$ | CH$_3$O | CH≡CCH$_2$O |
| 2209 | CF$_3$O | 5-benzofuryl | O | H | CH$_2$CH$_2$ | CH$_3$O | CH≡CCH$_2$O |
| 2210 | CH$_2$FO | 6-benzofuryl | O | H | CH$_2$CH$_2$ | CH$_3$O | CH≡CCH$_2$O |
| 2211 | CHF$_2$O | 6-benzofuryl | O | H | CH$_2$CH$_2$ | CH$_3$O | CH≡CCH$_2$O |
| 2212 | CF$_3$O | 6-benzofuryl | O | H | CH$_2$CH$_2$ | CH$_3$O | CH≡CCH$_2$O |
| 2213 | CH$_2$FO | 5-benzothienyl | O | H | CH$_2$CH$_2$ | CH$_3$O | CH≡CCH$_2$O |
| 2214 | CHF$_2$O | 5-benzothienyl | O | H | CH$_2$CH$_2$ | CH$_3$O | CH≡CCH$_2$O |
| 2215 | CF$_3$O | 5-benzothienyl | O | H | CH$_2$CH$_2$ | CH$_3$O | CH≡CCH$_2$O |
| 2216 | CH$_2$FO | 6-benzothienyl | O | H | CH$_2$CH$_2$ | CH$_3$O | CH≡CCH$_2$O |
| 2217 | CHF$_2$O | 6-benzothienyl | O | H | CH$_2$CH$_2$ | CH$_3$O | CH≡CCH$_2$O |
| 2218 | CF$_3$O | 6-benzothienyl | O | H | CH$_2$CH$_2$ | CH$_3$O | CH≡CCH$_2$O |
| 2219 | CH$_2$FO | 5-benzothiazolyl | O | H | CH$_2$CH$_2$ | CH$_3$O | CH≡CCH$_2$O |
| 2220 | CHF$_2$O | 5-benzothiazolyl | O | H | CH$_2$CH$_2$ | CH$_3$O | CH≡CCH$_2$O |
| 2221 | CF$_3$O | 5-benzothiazolyl | O | H | CH$_2$CH$_2$ | CH$_3$O | CH≡CCH$_2$O |
| 2222 | CH$_2$FO | 6-benzothiazolyl | O | H | CH$_2$CH$_2$ | CH$_3$O | CH≡CCH$_2$O |
| 2223 | CHF$_2$O | 6-benzothiazolyl | O | H | CH$_2$CH$_2$ | CH$_3$O | CH≡CCH$_2$O |
| 2224 | CF$_3$O | 6-benzothiazolyl | O | H | CH$_2$CH$_2$ | CH$_3$O | CH≡CCH$_2$O |
| 2225 | CH$_2$FO | 2-benzothiazolyl | O | H | CH$_2$CH$_2$ | CH$_3$O | CH≡CCH$_2$O |
| 2226 | CHF$_2$O | 2-benzothiazolyl | O | H | CH$_2$CH$_2$ | CH$_3$O | CH≡CCH$_2$O |
| 2227 | CF$_3$O | 2-benzothiazolyl | O | H | CH$_2$CH$_2$ | CH$_3$O | CH≡CCH$_2$O |
| 2228 | CH$_2$FO | 2-benzothienyl | O | H | CH$_2$CH$_2$ | CH$_3$O | CH≡CCH$_2$O |
| 2229 | CHF$_2$O | 2-benzothienyl | O | H | CH$_2$CH$_2$ | CH$_3$O | CH≡CCH$_2$O |
| 2230 | CF$_3$O | 2-benzothienyl | O | H | CH$_2$CH$_2$ | CH$_3$O | CH≡CCH$_2$O |
| 2231 | CH$_2$FO | 3-benzothienyl | O | H | CH$_2$CH$_2$ | CH$_3$O | CH≡CCH$_2$O |
| 2232 | CHF$_2$O | 3-benzothienyl | O | H | CH$_2$CH$_2$ | CH$_3$O | CH≡CCH$_2$O |
| 2233 | CF$_3$O | 3-benzothienyl | O | H | CH$_2$CH$_2$ | CH$_3$O | CH≡CCH$_2$O |
| 2234 | CH$_2$FO | 2-benzofuryl | O | H | CH$_2$CH$_2$ | CH$_3$O | CH≡CCH$_2$O |
| 2235 | CHF$_2$O | 2-benzofuryl | O | H | CH$_2$CH$_2$ | CH$_3$O | CH≡CCH$_2$O |
| 2236 | CF$_3$O | 2-benzofuryl | O | H | CH$_2$CH$_2$ | CH$_3$O | CH≡CCH$_2$O |

-continued

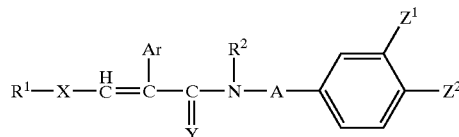

| Nos. | R¹X | Ar | Y | R² | A | Z¹ | Z² |
|---|---|---|---|---|---|---|---|
| 2237 | $CH_2FO$ | 3-benzofuryl | O | H | $CH_2CH_2$ | $CH_3O$ | $CH \equiv CCH_2O$ |
| 2238 | $CHF_2O$ | 3-benzofuryl | O | H | $CH_2CH_2$ | $CH_3O$ | $CH \equiv CCH_2O$ |
| 2239 | $CF_3O$ | 3-benzofuryl | O | H | $CH_2CH_2$ | $CH_3O$ | $CH \equiv CCH_2O$ |
| 2240 | $CH_2FO$ | benzo-1,2,3-thiazol-5-yl | O | H | $CH_2CH_2$ | $CH_3O$ | $CH \equiv CCH_2O$ |
| 2241 | $CHF_2O$ | benzo-1,2,3-thiazol-5-yl | O | H | $CH_2CH_2$ | $CH_3O$ | $CH \equiv CCH_2O$ |
| 2242 | $CF_3O$ | benzo-1,2,3-thiazol-5-yl | O | H | $CH_2CH_2$ | $CH_3O$ | $CH \equiv CCH_2O$ |
| 2243 | $CH_2FO$ | 2-benzimidazolyl | O | H | $CH_2CH_2$ | $CH_3O$ | $CH \equiv CCH_2O$ |
| 2244 | $CHF_2O$ | 2-benzimidazolyl | O | H | $CH_2CH_2$ | $CH_3O$ | $CH \equiv CCH_2O$ |
| 2245 | $CF_3O$ | 2-benzimidazolyl | O | H | $CH_2CH_2$ | $CH_3O$ | $CH \equiv CCH_2O$ |
| 2246 | $CF_3S$ | 2-thienyl | O | H | $CH_2CH_2$ | $CH_3O$ | $CH_3O$ |
| 2247 | $CH_2FO$ | 2-(1-methylbenzimidazolyl) | O | H | $CH_2CH_2$ | $CH_3O$ | $CH \equiv CCH_2O$ |
| 2248 | $CHF_2O$ | 2-(1-methylbenzimidazolyl) | O | H | $CH_2CH_2$ | $CH_3O$ | $CH \equiv CCH_2O$ |
| 2249 | $CF_3O$ | 2-(1-methylbenzimidazolyl) | O | H | $CH_2CH_2$ | $CH_3O$ | $CH \equiv CCH_2O$ |
| 2250 | $CH \equiv CCH_2O$ | 2-(5-methylthienyl) | O | H | $CH_2CH_2$ | $CH_3O$ | $CH \equiv CCH_2O$ |
| 2251 | $CH \equiv CCH_2O$ | 2-(5-trifluoromethyl thienyl) | O | H | $CH_2CH_2$ | $CH_3O$ | $CH_3O$ |
| 2252 | $CH \equiv CCH_2O$ | 2-(5-methylfuryl) | O | H | $CH_2CH_2$ | $CH_3O$ | $CH_3O$ |
| 2253 | $CH \equiv CCH_2O$ | 2-(5-trifluoromethyl pyridyl) | O | H | $CH_2CH_2$ | $CH_3O$ | $CH_3O$ |
| 2254 | $CH \equiv CCH_2O$ | 2-naphthyl | O | H | $CH_2CH_2$ | $CH_3O$ | $CH_3O$ |

Formulation examples are given below. Parts represent parts by weight. The numbers of the present compounds are represented by the above-mentioned numbers.

Formulation Example 1

Fifty parts of each of the present compounds 1001–1478 and 2001–2254, 3 parts of calcium ligninsulfonate, 2 parts of magnesium laurylsulfate and 45 parts of synthetic hydrated silica are pulverized and mixed well to give wettable powders of each compound.

Formulation Example 2

Twenty parts of each of the present compounds 1001–1478 and 2001–2254 and 1.5 parts of sorbitan trioleate are mixed with 28.5 parts of an aqueous solution containing 2 parts of polyvinyl alcohol, and wet-pulverized finely. To the obtained mixture, 40 parts of an aqueous solution containing 0.05 part of xanthan gum and 0.1 part of aluminium magnesium silicate is added and further 10 parts of propylene glycol are added to give a flowable of each compound.

Formulation Example 3

Two parts of each of the present compounds 1001–1478 and 2001–2254, 88 parts of kaolin clay and 10 parts of talc are pulverized and mixed well to give dusts of each compound.

Formulation Example 4

Five parts of each of the present compounds 1001–1478 and 2001–2254, 14 parts of polyoxyethylenestyryl phenyl ether, 6 parts of calcium dodecylbenzenesulfonate and 75 parts of xylene are mixed well to give emulsifiable concentrates of each compound.

Formulation Example 5

Two parts of each of the present compounds 1001–1478 and 2001–2254, 1 part of synthetic hydrated silica, 2 parts of calcium ligninsulfonate, 30 parts of bentonite and 65 parts of kaolin clay are pulverized and mixed well, and water is added thereto and kneaded, granulated and dried to give granules of each compound.

Formulation Example 6

Ten parts of each of the present compounds 1001–1478 and 2001–2254, 35 parts of white carbon (calsium silicate) containing 50% of ammonium polyoxyethylenealkyl ether sulfate and 55 parts of water are mixed and wet pulverized finely to give a flowable of each compound.

Next, usefulness of the present compounds for controlling plant diseases is shown by test examples. The present compounds are represented by the numbers referred to in the above table.

The control effect of the present compounds was evaluated by visually observing the area of a lesion on a sample plant in investigation and comparing the area of a lesion in a non-treatment district and the area of a lesion in a district treated with the present compound.

Test Example 1

Sand loam was compacted in a plastic pot, a grape (variety: Berry A) was seeded and grown in a green house for 40 days. The present compounds 1004, 1005, 1006, 1016, 1017, 1020, 1023, 1026, 1029, 1065, 1103, 1104, 1143, 1160, 1182, 1196, 1197, 1223, 1232, 1241, 1251, 1258, 1266, 1268, 1271, 1274, 1281, 1282, 1305, 1320, 1371, 2077 and 2133 were formulated into flowables according to formulation example 6, then, diluted with water to provide given concentration (200 ppm), and these were sprayed onto stems and leaves so as to give sufficient adhesion on the surface of grape leaves. After spraying, the plant was air-dried, and a suspension of zoosporangiua of *Plasmopara viticola* was inoculated by spraying. After inoculation, the plant was first left for one day at 23° C. under high humidity, then further left for 6 days in the green house, then the control effect was checked. As a result, the lesion areas on plants in the treatment districts using the present compounds were not more than 10% of the lesion area of a non-treatment district.

Test Example 2

Sand loam was compacted in a plastic pot, a grape (variety: Berry A) was seeded and grown in a green house for 40 days. The present compounds 1259, 1284, 1353, 1355, 1360, 1367, 1445, 1447 and 1450 were formulated into flowables according to formulation example 6, then, diluted with water to provide given concentration (50 ppm), and these were sprayed onto stems and leaves so as to give sufficient adhesion on the surface of grape leaves. After spraying, the plant was air-dried, and a suspension of zoosporangiua of *Plasmopara viticola* was inoculated by spraying. After inoculation, the plant was first left for one day at 23° C. under high humidity, then further left for 6 days in the green house, then the control effect was checked. As a result, the lesion areas on plants in the treatment districts using the present compounds were not more than 10% of the lesion area of a non-treatment district.

Test Example 3

Sand loam was compacted in a plastic pot, a grape (variety: Berry A) was seeded and grown in a green house for 40 days. The present compounds 1354, 1357, 1358, 1364, 1388, 1392, 1429 and 2202 were formulated into flowables according to formulation example 6, then, diluted with water to provide given concentration (12.5 ppm), and these were sprayed onto stems and leaves so as to give sufficient adhesion on the surface of grape leaves. After spraying, the plant was air-dried, and a suspension of zoosporangiua of *Plasmopara viticola* was inoculated by spraying. After inoculation, the plant was first left for one day at 23° C. under high humidity, then further left for 6 days in the green house, then the control effect was checked. As a result, the lesion areas on plants in the treatment districts using the present compounds were not more than 10% of the lesion area of a non-treatment district.

Test Example 4

Sand loam was compacted in a plastic pot, a tomato (variety: Ponterosa) was seeded and grown in a green house for 20 days. The present compounds 1004, 1005, 1006, 1016, 1017, 1020, 1023, 1026, 1029, 1034, 1065, 1103, 1104, 1122, 1143, 1160, 1182, 1185, 1196, 1197, 1223, 1124, 1127, 1232, 1241, 1251, 1258, 1259, 1268, 1269, 1274, 1281, 1282, 1284, 1299, 1320, 1353, 1354, 1358, 1360, 1388, 1367, 1392, 1429, 1445, 1448, 1450, 1465, 1476, 2077 and 2133 were formulated into flowables according to formulation example 6, then, diluted with water to provide given concentration (500 ppm), and these were sprayed onto stems and leaves so as to give sufficient adhesion on the surface of tomato leaves. After spraying, the plant was air-dried, and a suspension of zoosporangiua of *Phytophthora infestans* was inoculated by spraying. After inoculation, the plant was first left for one day at 23° C. under high humidity, then further left for 4 days in the green house, then the control effect was checked. As a result, the lesion areas on plants in the treatment districts using the present compounds were not more than 10% of the lesion area of a non-treatment district.

Industrial Applicability

The present compound has an excellent efficacy for controlling plant diseases and is useful as an active ingredient of fungicide, especially agricultural and horticultural fungicide.

What is claimed is:

1. An amide compound given by formula [I]:

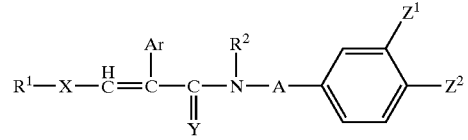

wherein $R^1$ represents a C1–C10 haloalkyl group, C2–C10 haloalkenyl group, C3–C10 haloalkynyl group, C3–C8 halocycloalkyl group or C3–C10 alkynyl group;

$R^2$ represents a hydrogen atom or C1–C3 alkyl group; X represents an oxygen atom or sulfur atom; Y represents an oxygen atom or sulfur atom; Ar represents a non heterocyclic, an aromatic group; A represents an ethylene group or trimethylene group, said ethylene group and trimethylene group may be substituted by one or more selected from halogen atom, amino group, hydroxy group, cyano group, nitro group, C1–C6 alkyl group, C3–C6 cycloalkyl group, C3–C6 cycloalkenyl group, C1–C6 alkoxy group, C1–C6 haloalkoxy group, C1–C6 alkylthio group, C1–C6 haloalkylthio group, C2–C6 (alkoxycarbonyl) group and tri(C1–C6 alkyl) silyl group; $Z^1$ and $Z^2$ are the same or different and represents a halogen atom, C1–C6 alkyl group, C1–C6 haloalkyl group, C2–C6 alkenyl group, C2–C6 alkynyl group, C3–C6 cycloalkyl group, C1–C6 alkoxy group, C1–C6 haloalkoxy group, C2–C6 (alkoxyalkoxy) group, C4–C6 (cycloalkylalkoxy) group, C3–C6 alkenyloxy group, C3–C6 haloalkenyloxy group, C3–C6 alkynyloxy group, C3–C6 haloalkynyloxy group, C3–C6 cycloalkoxy group, C3–C6 cycloalkenyloxy group, cyano C1–C5 alkoxy group, C1–C6 alkylthio group, C1–C6 haloalkylthio group, (C1–C5 alkoxy) carbonyl group, phenoxy group, benzyloxy group, hydroxy group or cyano group, the benzene ring of said phenyl group and benzyloxy group may be substituted by one or more selected from halogen atom, C1–C6 alkyl group, C1–C6 alkoxy group, trfluoromethyl group, amino group and nitro group; and $Z^1$ and $Z^2$ may represents C2–C6 alkylenedioxy group together.

2. An amide compound according to claim 1, wherein Ar is an aromatic hydrocarbyl group which may be substituted by at least one selected from halogen, amino, hydroxy, cyano, nitro, C1–C10 alkyl, C1–C10 haloalkyl, cyano C1–C9 alkyl, C2–C10 alkenyl, C2–C10 haloalkenyl, C2–C10 alkynyl, C2–C10 haloalkynyl, C3–C6 cycloalkyl, C3–C6 cycloalkenyl, C1–C10 alkoxy, C1–C10 haloalkoxy, C3–C10 alkenyloxy, C3–C10 haloalkenyloxy, C3–C10 alkynyloxy, C3–C10 haloalkynyloxy, C3–C10 cycloalkoxy, cyano C1–C9 alkoxy, C1–C10 alkylthio, C1–C10 haloalkylthio, C2–C10 (alkoxycarbonyl) and tri(C1–C6 alkyl)silyl.

3. An amide compound according to claim 2, wherein Ar is phenyl, or naphthyl, which may be substituted by at least one selected from halogen, amino, hydroxy, cyano, nitro, C1–C10 alkyl, C1–C10 haloalkyl, cyano C1–C9 alkyl, C2–C10 alkenyl, C2–C10 haloalkenyl, C2–C10 alkynyl, C2–C10 haloalkynyl, C3–C6 cycloalkyl, C3–C6 cycloalkenyl, C1–C10 alkoxy, C1–C10 haloalkoxy, C3–C10 alkenyloxy, C3–C10 haloalkenyloxy, C3–C10 alkynyloxy, C3–C10 haloalkynyloxy, C3–C10 cycloalkoxy, cyano C1–C9 alkoxy, C1–C10 alkylthio, C1–C10 haloalkylthio, C2–C10 (alkoxycarbonyl) and tri(C1–C6 alkyl)silyl.

4. An amide compound according to claim 2, wherein Ar is phenyl or naphthyl which may be substituted by at least one selected from halogen, amino, hydroxy, cyano, nitro, C1–C10 alkyl, C1–C10 haloalkyl, cyano C1–C9 alkyl, C2–C10 alkenyl, C2–C10 haloalkenyl, C2–C10 alkynyl, C2–C10 haloalkynyl, C3–C6 cycloalkyl, C3–C6 cycloalkenyl, C1–C10 alkoxy, C1–C10 haloalkoxy, C3–C10 alkenyloxy, C3–C10 haloalkenyloxy, C3–C10 alkynyloxy, C3–C10 haloalkynyloxy, C3–C10 cycloalkoxy, cyano C1–C9 alkoxy, C1–C10 alkylthio, C1–C10 haloalkylthio, C2–C10 (alkoxycarbonyl) and tri(C1–C6 alkyl)silyl.

5. An amide compound according to claim 2, wherein Ar is phenyl, 4-methylphenyl, 3-methylphenyl, 4-ethylphenyl, 4-methoxyphenyl, 3-methoxyphenyl, 4-chlorophenyl, 4-trifluoromethylphenyl, 3,4-tetramethylenephenyl, 3,4-trimethylenephenyl, 3,4-dichlorophenyl, 3,4-dimethoxyphenyl or 2-naphthyl.

6. An amide compound according to claim 1, wherein A is an ethylene group.

7. An amide compound according to claim 1, wherein $R^2$ is a hydrogen atom.

8. An amide compound according to claim 1, wherein both of X and Y are oxygen atoms.

9. An amide compound according to claim 1, wherein both of $Z^1$ and $Z^2$ are methoxy.

10. An amide compound according to claim 1, wherein $Z^1$ is methoxy and $Z^2$ is 2-propynyloxy.

11. An amide compound according to claim 1, wherein $R^1$ is a fluoromethyl, difluoromethyl, trifluoromethyl or 2-propynyl.

12. An amide compound according to claim 1, which is N-[2-(3,4-dimethoxyphenyl) ethyl]-3-difluoromethoxy-2-(4-methylphenyl)acrylamide, N-[2-(3,4-dimethoxyphenyl) ethyl]-3-difluoromethoxy-2-[2-(5,6,7,8-tetrahydronaphthalen-2-yl)]acrylamide, N-[2-{3-methoxy-4-(2-propynyloxy)phenyl}ethyl]-3-difluoromethoxy-2-(5,6,7,8-tetrahydronaphthalen-2-yl)acrylamide, N-[2-{3-methoxy-4-(2-propynyloxy)phenyl}ethyl]-3-difluoromethoxy-2-(4-methyphenyl) acrylamide, N-[2-(3,4-dimethoxyphenyl)ethyl]-3-difluoromethoxy-2-(4-chlorophenyl)acrylamide or N-[2-{3-methoxy-4-(2-propynyloxy)phenyl}ethyl]-3-difluoromethoxy-2-(4-chlorophenyl)acrylamide.

13. A fungicide which is characterized by comprising an amide compound described in claim 1 as an active ingredient, and a carrier.

14. A method for controlling plant diseases which is characterized by applying an effective amount of an amide compound described in claim 1 to plants.

* * * * *